US009856283B2

(12) United States Patent
Oscarson et al.

(10) Patent No.: US 9,856,283 B2
(45) Date of Patent: Jan. 2, 2018

(54) THIOSACCHARIDE MUCOLYTIC AGENTS

(71) Applicants: The Regents of The University of California, Oakland, CA (US); University College Dublin, Dublin (IE)

(72) Inventors: Stefan Oscarson, Blackrock (IE); John Vincent Fahy, San Francisco, CA (US); Shaopeng Yuan, San Francisco, CA (US); Stephen Carrington, Roundwood (IE)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 12 days.

(21) Appl. No.: 14/847,439

(22) Filed: Sep. 8, 2015

(65) Prior Publication Data

US 2016/0060284 A1 Mar. 3, 2016

Related U.S. Application Data

(63) Continuation of application No. PCT/US2014/028656, filed on Mar. 14, 2014.

(60) Provisional application No. 61/784,856, filed on Mar. 14, 2013.

(51) Int. Cl.
*C07H 15/04* (2006.01)
*C07H 5/04* (2006.01)
*A61K 31/7028* (2006.01)
*A61K 31/70* (2006.01)
*A61K 31/7016* (2006.01)
*A61K 31/702* (2006.01)
*C07D 309/10* (2006.01)
*C07H 13/04* (2006.01)

(52) U.S. Cl.
CPC ............ *C07H 15/04* (2013.01); *A61K 31/70* (2013.01); *A61K 31/702* (2013.01); *A61K 31/7016* (2013.01); *A61K 31/7028* (2013.01); *C07D 309/10* (2013.01); *C07H 5/04* (2013.01); *C07H 13/04* (2013.01)

(58) Field of Classification Search
None
See application file for complete search history.

(56) References Cited

U.S. PATENT DOCUMENTS

| | | |
|---|---|---|
| 4,861,760 A | 8/1989 | Mazuel et al. |
| 4,911,920 A | 3/1990 | Jani et al. |
| 5,212,162 A | 5/1993 | Missel et al. |
| 5,403,841 A | 4/1995 | Lang et al. |
| 6,624,190 B2 | 9/2003 | Khoury et al. |
| 9,346,753 B2 | 5/2016 | Johnson et al. |
| 2004/0037780 A1 | 2/2004 | Parsons et al. |
| 2005/0130240 A1* | 6/2005 | Lin .................... B82Y 5/00 435/7.32 |
| 2007/0232836 A1 | 10/2007 | Steenkamp |
| 2008/0269163 A1 | 10/2008 | Sostaric et al. |
| 2010/0172845 A1 | 7/2010 | Stoops et al. |
| 2015/0056305 A1 | 2/2015 | Johnson et al. |
| 2015/0307530 A1 | 10/2015 | Johnson et al. |
| 2016/0060284 A1 | 3/2016 | Oscarson et al. |
| 2016/0222023 A1 | 8/2016 | Johnson et al. |

FOREIGN PATENT DOCUMENTS

| | | | |
|---|---|---|---|
| EP | 0 552 551 A1 | 7/1993 | |
| WO | WO-96/05309 A2 | 2/1996 | |
| WO | WO-96/05309 A3 | 2/1996 | |
| WO | WO 0064485 A2 * | 11/2000 | ....... A61K 47/48007 |
| WO | WO-2007/091040 A2 | 8/2007 | |
| WO | WO-2007/091040 A3 | 8/2007 | |

OTHER PUBLICATIONS

Agaki, Chem Pharm Bull (Tokyo). Jul. 1962;10:562-6.*
Priebe, Tetrahedron Letters, vol. 32, No. 28, pp. 3313-3316, 1991.*
Otterson, Clin Cancer Res. 2007;13(4) Feb. 15, 2007.*
Machell, Journal of the Chemical Society (1961) 3308-12.*
Houseman, Langmuir (2003), 19(5), 1522-1531.*
Pei (Bioorganic & Medicinal Chemistry Letters 15 (2005) 2707-2710).*
Al-Muhammed, J. et al. (May-Jun. 1996). "In-vivo studies on dexamethasone sodium phosphate liposomes," *J Microencapsul* 13(3):293-306.
Berge, S.M. et al. (Jan. 1977). "Pharmaceutical salts," *J Pharm Sci* 66(1):1-19.
Chonn, A. et al. (Dec. 1995). "Recent advances in liposomal drug-delivery systems," *Curr Opin Biotechnol* 6(6):698-708.
Eyles, J.E. et al. (Jul. 1997). "Oral delivery and fate of poly(lactic acid) microsphere-encapsulated interferon in rats," *J Pharm Pharmacol* 49(7):669-674.
Gao, Z.H. et al. (Jun. 1995). "Controlled release of a contraceptive steroid from biodegradable and injectable gel formulations: in vitro evaluation," *Pharm Res* 12(6):857-863.
International Search Report dated Sep. 26, 2014, for PCT Application No. PCT/US2014/028656, filed Mar. 14, 2014, 5 pages.
Konstantinovic, S. et al. (2005). "$SnCl_4$ Induced Formation of $C_3$-$C_{11}$ Alkenyl Galactopyranosides as Precursors for Unsaturated Neutral Bolaforms," *J. Serbian Chem. Soc.* 70(7):925-929.
Leitner, V.M. et al. (Sep. 2003). "Thiolated polymers: evidence for the formation of disulphide bonds with mucus glycoproteins," *Eur J Pharm Biopharm* 56(2):207-214.

(Continued)

*Primary Examiner* — Layla D Berry
(74) *Attorney, Agent, or Firm* — Mintz Levin Cohn Ferris Glovsky and Popeo, P.C.

(57) ABSTRACT

There are provided, inter alia, methods for decreasing mucus elasticity or decreasing mucus viscosity in a subject in need thereof, the methods including administering to the subject an effective amount of a thiosaccharide mucolytic agent, and compounds and pharmaceutical compositions useful for the methods.

31 Claims, 6 Drawing Sheets

(56) References Cited

OTHER PUBLICATIONS

Ostro, M.J. et al. (Aug. 1989). "Use of liposomes as injectable-drug delivery systems," *Am J Hosp Pharm* 46(8):1576-1587.
Rao, K.P. et al. (1995). "Recent developments of collagen-based materials for medical applications and drug delivery systems," *J Biomater Sci Polym Ed* 7(7):623-645.
Written Opinion dated Sep. 26, 2014, for PCT Application No. PCT/US2014/028656, filed Mar. 14, 2014, 7 pages.
CAS Registry No. 10593-29-0, 1-thio-β-D-Glucose (sodium salt), 1 page, accessed May 12, 2017.

\* cited by examiner

THIOSACCHARIDE MUCOLYTIC AGENTS

CROSS-REFERENCES TO RELATED APPLICATIONS

This application in a continuation of International Application No. PCT/US2014/028656, filed Mar. 14, 2014, which claims the benefit of U.S. Provisional Application No. 61/784,856, filed Mar. 14, 2013, the contents of each of which are incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with Government support under Grant Nos. RO1 HL080414 and P50 HL107191 awarded by the National Institutes of Health. The Government has certain rights in the invention.

BACKGROUND OF THE INVENTION

Increased mucus elasticity is a major cause of morbidity in patients with chronic airway diseases such as asthma, cystic fibrosis (CF), chronic bronchitis, and patients on mechanical ventilators. Reducing conditions prevail in normal lung secretions, but airway inflammation and administration of supplemental oxygen can shift the airway redox balance. In recent studies, we have shown that oxidation of airway mucus generates disulfide crosslinkages between mucin polymers that increase the elasticity of airway mucus gels. We believe that this mechanism of pathologic mucus formation operates broadly in the upper and lower respiratory tract, because inflammation is invariably associated with alterations in redox balance. In addition, we think the mechanism is relevant in patients who need supplemental oxygen treatment, including those on mechanical ventilators, because we have shown that oxygen increases mucus elasticity. Taken together, our recent results suggest that the oxidative stress that occurs commonly in upper and lower respiratory tract diseases, including during treatment with oxygen, plays an unexpected role in the formation of mucus with pathologically high elasticity. These findings provide a strong rationale for treatment of pathologic mucus in multiple clinical situations with reducing agents. Importantly, such mucolytic therapy will be helpful not just as a reliever of symptoms of upper or lower airway congestion. Experience with rhDNAse and other mucoactive drugs such as hypertonic saline has shown that effective mucolysis is also associated with improvements in other clinical outcomes, such as exacerbation and hospitalization rates.

"N-Acetylcysteine (NAC, "MUCOMYST®") is a currently available reducing agent that has been used as a mucolytic since the 1960s. The problem is that it has several limitations, including its unstable/volatile nature, which probably contributes to its relatively low potency. In addition, its $pK_a$ of 2.2 has disadvantages, particularly for topical or aerosol administration. Further, NAC has a "rotten egg" smell when nebulized and can be irritating when inhaled. For all of these reasons, NAC has not be a particularly successful mucolytic and does not satisfy a large unmet need for novel mucolytic therapies for a wide range of acute and chronic airway disease.

To fill an unmet need, we have synthesized and tested novel reducing agents built on a carbohydrate scaffold. We have evaluated the relative effects of these compounds on the elasticity of airway mucus from human subjects with and without airway disease. To measure elasticity, we have optimized methods using a cone and plate rheometer, including methods to increase signal to noise ratios. To collect airway mucus, we have recruited human subjects who can provide spontaneously expectorated or induced sputum (using hypertonic saline). Disease groups of interest include, inter alia, patients with cystic fibrosis, asthma, chronic bronchitis, bronchiectasis, bronchiolitis, acute and chronic sinusitis, as well as patients who develop "thick" (highly elastic) mucus while being treated with positive pressure mechanical ventilation.

BRIEF SUMMARY OF THE INVENTION

In a first aspect, there is provided a method of decreasing mucus elasticity or decreasing mucus viscosity in a subject in need thereof. The method includes administering to the subject an effective amount of a thiosaccharide mucolytic agent.

In another aspect, there is provided a compound with structure of Formula (I), wherein $R^1$, $R^2$, $R^3$, $R^4$, $R^5$ and $R^{5'}$ are as defined herein:

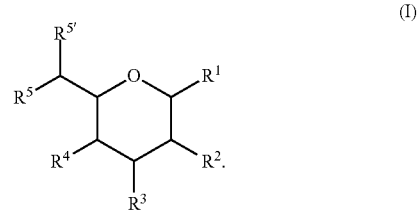

(I)

In another aspect, there is provided a compound with structure of Formula (III), wherein $R^1$, $R^2$, $R^3$, $R^4$, $R^5$, $R^7$, $R^8$, $R^9$ and $R^{10}$ are as defined herein:

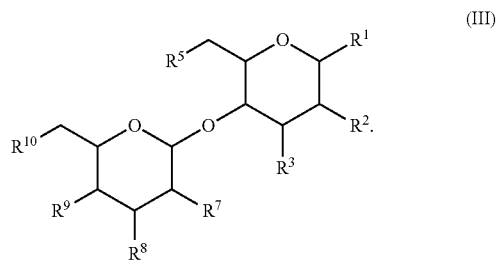

(III)

In another aspect, there is provided a compound with structure of Formula (IV), wherein $R^1$, $R^2$, $R^3$, $R^4$, $R^5$, $R^7$, $R^8$, $R^{10}$, $R^{12}$, $R^{13}$, $R^{14}$ and $R^{15}$ are as defined herein:

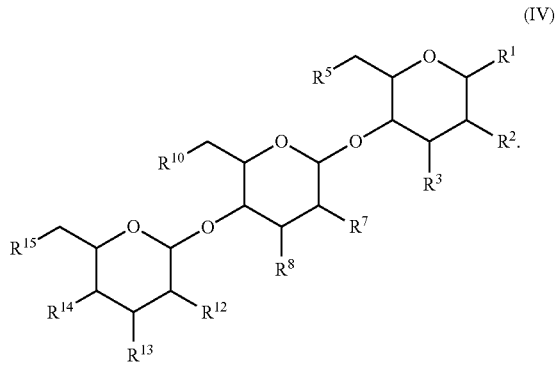

(IV)

In another aspect, there is provided a compound with structure of Formula (V), wherein $R^1, R^2, R^3, R^4, R^5, R^7, R^8, R^{10}, R^{12}, R^{13}, R^{14}$ and $R^{15}$ are as defined herein:

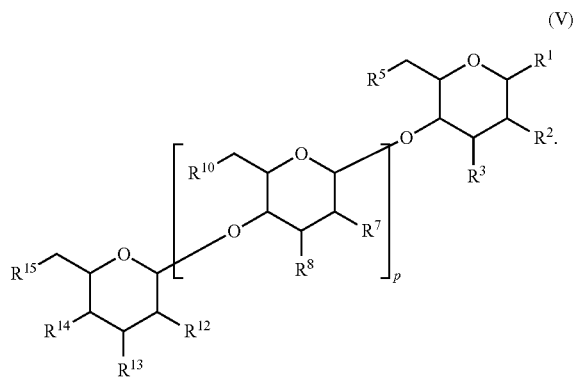

(V)

In another aspect, there is provided a pulmonary pharmaceutical composition including a pulmonary pharmaceutical carrier and a thiosaccharide mucolytic agent, as disclosed herein.

BRIEF DESCRIPTION OF THE DRAWINGS

FIGS. 5B-5C depict histograms of the average mucolytic effect of Cmpd 1 at two minutes (FIG. 5B) which is significantly larger than observed for NAC. The mucolytic effects of Cmpd 1 and NAC at 12 minutes (FIG. 5C) are similar. Data in FIGS. 5B-5C are mean±SEM (Standard Error of the Mean). Legend: MDG (box); NAC (circle); Cmpd 1 (triangle). *Indicates $p<0.05$;  Indicates $p<0.01$; * Indicates $p<0.001$.

FIG. 7A: Low concentrations (10 mM) of Cmpd 1, Cmpd 2, NAC, glutathione (GSH) and parent sugar have differing effects on the elastic modulus (G') of CF sputum (n=5 donors) over a 12-minute test period. Cmpd 2 has the largest effect. Legend: MDG (solid square); Glutathione (GSH) (solid triangle); NAC (solid diamond); Cmpd 1 (open circle); Cmpd 2 (solid circle). FIGS. 7B-7C depict histograms of the mucolytic effects of compounds at 2-minutes (FIG. 7B) and 12-minutes (FIG. 7C). The mucolytic effects of Cmpd 2 at 12-minutes are significantly greater than observed for NAC. The mucolytic effects of Cmpd 2 at 12 minutes is significantly greater than for Cmpd 1. Glutathione and MDG are ineffective as mucolytics at this concentration. Data in FIGS. 7B-7C are mean±SEM. *Indicates $p<0.05$;  Indicates $p<0.01$; * Indicates $p<0.001$.

DETAILED DESCRIPTION OF THE INVENTION

I. Definitions

Figure 1:
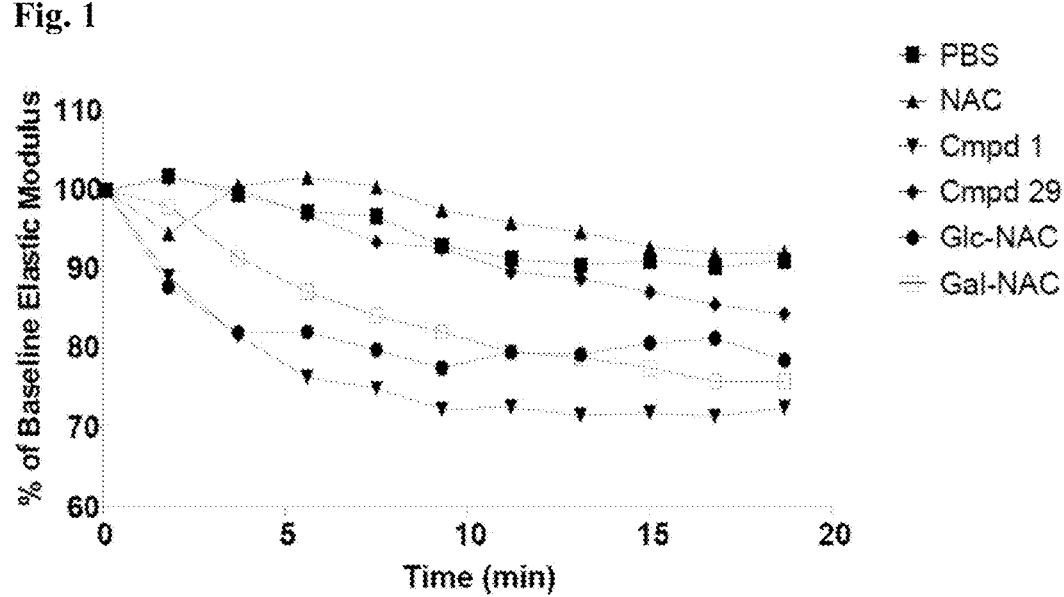
FIG. 1 depicts the effect of thiosaccharides disclosed herein (1 mM) on the elastic modulus (G') of pooled induced sputum from five healthy subjects. The data are shown compared to the effect of PBS and NAC. Legend: Phosphate buffered saline (PBS) (closed box); N-acetylcysteine (NAC) (triangle tip up); Cmpd 1 (triangle tip down); Cmpd 29 (diamond); Glc-NAC (circle); Gal-NAC (open circle).

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched chain, or combination thereof, which may be fully saturated, mono- or polyunsaturated and can include di- and multivalent radicals, having the number of carbon atoms designated (i.e., $C_1$-$C_{10}$ means one to ten carbons). Alkyl is an uncyclized chain. Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. An alkoxy is an alkyl attached to the remainder of the molecule via an oxygen linker (—O—).

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene) group will have from 1 to 24 carbon atoms, with those groups having 10 or fewer carbon atoms being preferred in the present invention. A "lower alkyl" or "lower alkylene" is a $C_1$-$C_8$ alkyl or alkylene group.

The term "heteroalkyl," by itself or in combination with another term, means, unless otherwise stated, a stable straight or branched chain, or combinations thereof, consisting of at least one carbon atom and at least one heteroatom selected from the group consisting of O, N, P, Si, and S, and wherein the nitrogen and sulfur atoms may optionally be oxidized, and the nitrogen heteroatom may optionally be quaternized. The heteroatom(s) O, N, P, S, and Si may be placed at any interior position of the heteroalkyl group or at the position at which the alkyl group is attached to the remainder of the molecule. Heteroalkyl is an uncyclized chain. Examples include, but are not limited to: —CH$_2$—CH$_2$—O—CH$_3$, —CH$_2$—CH$_2$—NH—CH$_3$, —CH$_2$—CH$_2$—N(CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —Si(CH$_3$)$_3$, —CH$_2$—CH=N—OCH$_3$, —CH=CH—N(CH$_3$)—CH$_3$, —O—CH$_3$, —O—CH$_2$—CH$_3$, and —CN. Up to two heteroatoms may be consecutive, such as, for example, —CH$_2$—NH—OCH$_3$. A "thiol-alkyl" (e.g., $C_1$-$C_{10}$ thiol-alkyl) is an alkyl having a thiol substituent. A "thiol-heteroalkyl" (e.g., 2 to 10 membered thiol-heteroalkyl) is a heteroalkyl having a thiol substituent. A "thiol-unsaturated alkyl" (e.g., $C_1$-$C_{10}$ thiol-unsaturated alkyl) is an alkyl having a thiol substituent and having a double bond or a triple bond.

Similarly, the term "heteroalkylene," by itself or as part of another substituent, means, unless otherwise stated, a divalent radical derived from heteroalkyl, as exemplified, but not limited by, —CH$_2$—CH$_2$—S—CH$_2$—CH$_2$— and —CH$_2$—S—CH$_2$—CH$_2$—NH—CH$_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, cyclic versions of "alkyl" and "heteroalkyl," respectively. Cycloalkyl and heteroalkyl are not aromatic. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively.

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$)alkyl" includes, but is not limited to, fluoromethyl, difluoromethyl, trifluoromethyl, 2,2,2-trifluoroethyl, 4-chlorobutyl, 3-bromopropyl, and the like.

The term "acyl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl, and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

The term "oxo," as used herein, means an oxygen that is double bonded to a carbon atom.

The term "alkylsulfonyl," as used herein, means a moiety having the formula —S(O$_2$)—R', where R' is an alkyl group as defined above. R' may have a specified number of carbons (e.g., "C$_1$-C$_4$ alkylsulfonyl").

Each of the above terms (e.g., "alkyl," "heteroalkyl," "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, and —NO$_2$ in a number ranging from zero to (2m'+1), where m' is the total number of carbon atoms in such radical. R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN, —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In embodiments, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'—, or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R'")$_d$—, where s and d are independently integers of from 0 to 3, and X' is —O—, —NR'—, —S—, —S(O)—, —S(O)$_2$—, or —S(O)$_2$NR'—. The substituents R, R', R", and R'" are preferably independently selected from hydrogen, substituted or unsubstituted alkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include oxygen (O), nitrogen (N), sulfur (S), phosphorus (P), and silicon (Si).

A "substituent group," as used herein, means a group selected from the following moieties:

(A) —OH, —NH$_2$, —SH, —CN, —CF$_3$, —NO$_2$, oxo, halogen, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, and heteroaryl, substituted with at least one substituent selected from:

(i) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, and heteroaryl, substituted with at least one substituent selected from:

(a) oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, or heteroaryl, substituted with at least one substituent selected from:

oxo, —OH, —NH$_2$, —SH, —CN, —CF$_3$, —NO$_2$, halogen, unsubstituted alkyl, unsubstituted heteroalkyl, unsubstituted cycloalkyl, unsubstituted heterocycloalkyl, unsubstituted aryl, and unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_4$-$C_8$ cycloalkyl, and each substituted or unsubstituted heterocycloalkyl is a substituted or unsubstituted 4 to 8 membered heterocycloalkyl.

A "lower substituent" or "lower substituent group," as used herein, means a group selected from all of the substituents described above for a "substituent group," wherein each substituted or unsubstituted alkyl is a substituted or unsubstituted $C_1$-$C_5$alkyl, each substituted or unsubstituted heteroalkyl is a substituted or unsubstituted 2 to 8 membered heteroalkyl, each substituted or unsubstituted cycloalkyl is a substituted or unsubstituted $C_5$-$C_7$ cycloalkyl, and each substituted or unsubstituted heterocycloalkyl is a substituted or unsubstituted 5 to 7 membered heterocycloalkyl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_5$alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth herein.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

In addition to salt forms, the present invention provides compounds in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, tautomers, geometric isomers, and individual isomers are encompassed within the scope of the present invention. The compounds of the present invention do not include those that are known in the art to be too unstable to synthesize and/or isolate.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

The symbol "∼∼" denotes the point of attachment of a chemical moiety to the remainder of a molecule or chemical formula.

The term "thiosaccharide" as used herein refers to a compound containing at least one tetrahydropyrane ring substituted with at least one thiol (—SH) containing moiety or at least one thioacetyl (—SAc) moiety (and optionally further substituted for example, with hydroxyl moieties or additional tetrahydropyrane rings tetrahydropyrane rings or tetrahydrofuran rings via ether linkers) or at least one tetrahydrofuran ring substituted with at least one thiol containing moiety (and optionally further substituted for example, with hydroxyl moieties or additional tetrahydropyranee rings or tetrahydrofuran rings via ether linkers). Thus, the term "thiol saccharide" refers to a thiosaccharide with at least one thiol (—SH) moiety, and the term "thioacetyl saccharide" refers to a thiosaccharide with at least one thioacetyl (—SAc) moiety. The tetrahydropyrane ring may be a pyranose ring or pyranoside ring in which one or more hydroxyl groups are replaced with a thiol containing moiety (referred to herein as a "thiol pyranose" or "thiol pyranoside", respectively). The tetrahydropyrane ring may be a pyranose ring or pyranoside ring in which one or more hydroxyl groups are replaced with a thioacetyl containing moiety (referred to herein as a "thioacetyl pyranose" or "thioacetyl pyranoside", respectively). The tetrahydrofuran ring may be a furanose ring or furanoside ring in which one or more hydroxyl groups are replaced with a thiol containing moiety (referred to herein as a "thiol pyranose" or "thiol pyranoside", respectively). The tetrahydrofuran ring may be a furanose ring or furanoside ring in which one or more hydroxyl groups are replaced with a thioacetyl containing moiety (referred to herein as a "thioacetyl pyranose" or "thioacetyl pyranoside", respectively). A "thiol monosaccharide" (e.g., thiol monopyranose, thiol monopyranoside, thiol monofuranose, thiol monofuranoside) as used herein refers to compound containing one tetrahydropyrane ring substituted with at least one thiol (—SH) containing moiety or one tetreahydrofuran ring substituted with at least one thiol (—SH) containing moiety. A "thioacetyl monosaccharide" (e.g., thioacetyl monopyranose, thioacetyl monopyranoside, thioacetyl monofuranose, thioacetyl monofuranoside) as used herein refers to compound containing one tetrahydropyrane ring substituted with at least one thioacetyl (—SAc) containing moiety or one tetrahydrofuran ring substituted with at least one thioacetyl (—SAc) containing moiety. A "thiol disaccharide" (e.g. thiol dipyranoside, thiol dipyranoside, thiol difuranose, thiol difuranoside) as used herein refers to a compound containing two tetrahydropyrane rings substituted with at least one thiol (—SH) containing moiety. A "thioacetyl disaccharide" (e.g., thioacetyl dipyranoside, thioacetyl dipyranoside, thioacetyl difuranose, thioacetyl difuranoside) as used herein refers to compound containing two tetrahydropyrane rings substituted with at least one thioacetyl (—SAc) containing moiety. A "thiol trisaccharide" (e.g., thiol tripyranoside, thiol tripyranoside, thiol trifuranose, thiol trifuranoside) as used herein refers to a compound containing three tetrahydropyrane rings substituted with at least one thiol (—SH) containing moiety. A "thioacetyl trisaccharide" (e.g., thioacetyl tripyranoside, thioacetyl tripyranoside, thioacetyl trifuranose, thioacetyl trifuranoside) as used herein refers to compound containing three tetrahydropyrane rings substituted with at least one thioacetyl (—SAc) containing moiety. A "thiol oligosaccharide" (e.g., thiol oligopyranoside, thiol oligopyranoside, thiol oligofuranose, thiol oligofuranoside) as used herein refers to a compound containing more than three tetrahydropyrane rings substituted with at least one thiol (—SH) containing moiety. A "thioacetyl oligosaccharide" (e.g., thioacetyl oligopyranoside, thioacetyl oligopyranoside, thioacetyl oligofuranose, thioacetyl oligofuranoside) as used herein refers to a compound containing more than three tetrahydropyrane rings substituted with at least one thioacetyl (—SAc) containing moiety.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat excess mucus in the airway by decreasing mucus elasticity or decreasing mucus viscosity in a subject in need thereof. The term "treating," and conjugations thereof, include prevention of an injury, pathology, condition, or disease.

An "effective amount" is an amount sufficient to accomplish a stated purpose (e.g., achieve the effect for which it is administered, treat a disease, reduce mucus at a target organ, reduce one or more symptoms of a disease or condition, and the like). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of a compound disclosed herein required to decrease mucus elasticity or decrease mucus viscosity in a subject in need thereof. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"Subject," "patient," "subject in need thereof" and the like refer to a living organism suffering from or prone to a disease or condition that can be treated by administration of a compound or pharmaceutical composition, as provided herein. Non-limiting examples include humans, other mammals, bovines, rats, mice, dogs, monkeys, goat, sheep, cows, deer, and other non-mammalian animals. In embodiments, a subject is human.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Unless indicated to the contrary, the terms "active agent," "active ingredient," "therapeutically active agent," "therapeutic agent" and like are used synonymously. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, polyethylene glycol, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

As used herein, the term "administering" means oral administration, administration as an inhaled aerosol or as an inhaled dry powder, suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example bronchodilators (beta agonists, anticholinergics), corticosteroids, antibiotics, cancer therapies such as chemotherapy, hormonal therapy, radiotherapy, or immunotherapy. The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g., to reduce metabolic degradation, or to promote the penetration of tissues, mucus, or pathologic biofilms by the active substance). The preparations may also be combined with other mucolytic drug classes (e.g., rhDNase, as known in the art) or with inhaled bronchodilators (short or long acting beta agonists, short or long acting anticholinergics), inhaled corticosteroids, or inhaled antibiotics to improve the efficacy of these drugs by providing additive or synergistic effects. The compositions of the present invention can be delivered transdermally, by a topical route, formulated as applicator sticks, solutions, suspensions, emulsions, gels, creams, ointments, nanoparticles, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.*

49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Pharmaceutical compositions provided by the present invention include compositions wherein the active ingredient (e.g., compounds described herein, including embodiments or examples) is contained in a therapeutically effective amount, i.e., in an amount effective to achieve its intended purpose. The actual amount effective for a particular application will depend, inter alia, on the condition being treated. Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

II. Methods of Use

In one aspect, there is provided a method of decreasing mucus elasticity or decreasing mucus viscosity in a subject in need thereof. For example, the method can be use of a thiosaccharide mucolytic agent for decreasing mucus elasticity or decreasing mucus viscosity in a subject in need thereof. The method includes administering to the subject an effective amount of a thiosaccharide mucolytic agent. The terms "elastic," "elasticity" and the like refer herein, in the usual and customary sense, to the ability of a material to return to an original shape after experiencing a deformation due to an external force (e.g., solid behavior). Thus, the term "mucus elasticity" refers herein to the ability of mucus to return to an original shape after experiencing a deformation in shape. The terms "viscous," "viscosity" and the like refer herein, in the usual and customary sense, to a measure of the resistance of a material to deformation (e.g., liquid behavior) upon application of a force (e.g., shear stress or tensile stress). Thus, the term "mucus viscosity" refers herein to a measure of the resistance of mucus to deformation upon application of an external force, whereby higher mucus viscosity means that the mucus is less deformable.

Without wishing to be bound by any theory, it is believed that elasticity represents mainly intermolecular cross-links, and viscosity mainly represents molecule/particle sizes. Moreover, in some embodiments, the thiosaccharide mucolytic agents disclosed herein function by breaking disulfide bonds cross-links in the mucus gel. Accordingly, in some embodiments, the reduction of elasticity is a direct effect of breaking disulfide bond crosslinkages. In considering the mucus network as a whole, by breaking down cross-links the average size of molecule/particles forming the mucus gel may be reduced. In some embodiments, the reduction of molecular/particle size and cross linking within mucus gels will increase the mean pore size of the gel. This in turn can increase the penetrability of the gel. Indeed, in some embodiments, administration to mucus gel of thiosaccharide mucolytic agents disclosed herein will decrease the elastic modulus of the mucus gel. Thus, the thiosaccharide mucolytic agents may have the effect of increasing gel pore size. In embodiments, the increase in gel pore size improves the penetration of a variety of additional agents including e.g., natural mucolytics like proteases or co-administered drugs (e.g., aerosol bronchodilators (e.g., beta agonists, anticholinergics), anti-inflammatory drugs and aerosol antibiotics) and other classes of mucolytic agents (e.g., rhDNase).

In embodiments, the method includes decreasing mucus elasticity in the subject. In embodiments, the method includes decreasing mucus viscosity in the subject. In embodiments, the method includes decreasing mucus viscoelasticity in the subject. The term "viscoelasticity" refers herein, in the usual and customary sense, to the property of materials that exhibit both viscous and elastic characteristics in response to a deformation. Thus, the term "mucus viscoelasticity" refers herein to a characteristic of mucus which exhibits both viscous and elastic characteristics when undergoing deformation.

Without wishing to be bound by any theory, it is believed that decreasing mucus elasticity, decreasing mucus viscosity, or decreasing mucus viscoelasticity is useful for a variety of medical, dental and veterinary indications. For example, in embodiments administration of compounds disclosed herein is useful for relief of upper and lower airway congestion by the physiological mechanisms of mucociliary clearance, as known in the art. Specifically, a decrease in mucus elasticity, viscosity or viscoelasticity is known to facilitate mucociliary clearance. In embodiments, administration of compounds disclosed herein is useful for veterinary (e.g., equine) intervention in strangle or guttural pouch infections (e.g., mycotic or bacterial infections) as a primary treatment for mucus accumulation. In embodiments, administration of compounds disclosed herein is useful to enhance penetration of another therapeutic agent. In embodiments, administration of compounds disclosed herein is useful for veterinary (e.g., equine) intervention in recurrent airway obstruction. In embodiments, the recurrent airway obstruction is caused by fungal allergy, mucus accumulation, or both.

In embodiments, the method is useful for targeted removal of mucus from a mucosal surface. The terms "mucosal surface" and the like refer, in the usual and customary sense, to a layer of cells (e.g., an epithelial layer) having mucus disposed thereon. Exemplary mucosal surfaces include skin, lungs, nostrils, sinuses, gastrointestinal tract, reproductive tract, urinary tract, eye, and the like. In embodiments, the method is useful for targeted removal of mucus from a mucosal surface, wherein the mucus provides a barrier to mucosal or transmucosal drug delivery. In embodiments, the method provides enhanced drug delivery by targeted removal of mucus from a mucosal surface. In embodiments, the mucosal surface includes the gastrointestinal tract, and the drug delivery is oral drug delivery.

In embodiments, the method is useful for removal of accumulated mucus at any mucosal surface. In embodiments, the accumulated mucus contributes directly or indirectly to the existence, symptomatology, or progression of disease.

In embodiments, the method is useful for removal of accumulated mucus at any mucosal surface, wherein the mucus is a component of a microbial biofilm. The terms "microbial biofilm" and the like refer, in the usual and customary sense, to an aggregation of microorganisms in which the component cells adhere to each other on a surface. The aggregation of microorganisms can be embedded within a matrix which can include mucus. Thus, removal of accumulated mucus in a microbial biofilm can facilitate exposure of the microorganisms to antibiotic treatment with an antimicrobial agent. In embodiments, administration of a compound disclosed herein facilitates penetration of an antimicrobial agent into the microbial biofilm. In embodiments, administration of a compound disclosed herein in combination with an antimicrobial agent provides synergistic treatment for the microorganisms within the microbial biofilm. The terms "synergistic" and the like in the context of administration of a compound disclosed herein in combination with another therapeutic agent (e.g., antimicrobial agent) refer, in the usual and customary sense, to a resulting effect (e.g., antibiotic efficacy) for the combination which is greater than the summed effects of the administration of either a compound disclosed herein or an antimicrobial agent alone.

In embodiments, the lung is specifically contemplated as the target organ. In embodiments, the method include administration of the thiosaccharide mucolytic agent to the lung of a subject in need thereof. Thus, in embodiments, the subject suffers a condition of the lung including chronic obstructive pulmonary disease (COPD), cystic fibrosis (CF), chronic asthma with airflow obstruction, chronic asthma in which mucus obstruction is found, acute asthma in which mucus plugs are life threatening, bronchiectasis, bronchiolitis, allergic bronchopulmonary aspergillosis, pneumonia, and mechanical ventilator-associated lung injury where mucus pathology is prominent. In embodiments, the method is useful to prevent oxidative cross-linking of lung mucins in subjects undergoing inhaled oxygen therapy.

In embodiments, the method is useful for amelioration of recurrent airway obstruction. In embodiments, the subject is human. In embodiments, the subject is a non-human animal. In embodiments, the subject is a horse.

In embodiments, the upper respiratory tract is specifically contemplated as the target organ. In embodiments, the subject suffers chronic rhinitis, acaute sinusitis, chronic sinusitis, chronic sinusitis with mucocele, and post-nasal drip.

In embodiments, the subject in need is in immediate need, presenting symptoms of acute airflow obstruction, acute shortness of breadth, acute asphyxia, acute symptoms of obstructive pulmonary disease (COPD), acute symptoms of cystic fibrosis (CF), acute asthma symptoms with airflow obstruction, acute asthma symptoms in which mucus obstruction is found, acute asthma in which mucus plugs are life threatening, acute symptoms of bronchiectasis, acute symptoms of bronchiolitis, acute symptoms of allergic bronchopulmonary aspergillosis, acute symptoms of pneumonia, or acute symptoms of mechanical ventilator-associated lung injury where mucus pathology is prominent, as known in the art. The term "acute" and the like refer, in the usual and customary sense, to a disease or disorder with rapid onset, often life threatening. Without wishing to be bound by any theory, it is believed that compliance of a subject to a treatment regimen increases with speed of onset of the effects of an administered compound disclosed herein. As discussed herein, compounds disclosed herein provide significantly faster onset of action relative to compounds routinely employed in treatment situations.

In embodiments, the rapid onset of action of compounds disclosed herein provides for less diffusion from the site of action, e.g., the lung. Accordingly, less material is required to achieve a beneficial result, e.g., reduction in acute airflow obstruction, thus implicating smaller dosage requirements relative to compounds routinely employed in treatment situations.

In embodiments, the ear is specifically contemplated as the target organ. Thus, in embodiments, the subject suffers from otitis media with mucus accumulation.

In embodiments, the eye is specifically contemplated as the target organ. Thus, in embodiments, the subject suffers from filamentary keratitis, keratitis sicca, dry eye syndrome, blepharitis, conjunctivitis, or any eye disease acute or chronic in which excess mucus forms on the eye.

In another aspect, there is provided a method for treatment in a subject in need thereof. The method includes administering an effective amount of a compound disclosed herein in combination with another therapeutic agent, wherein the therapeutic action of the therapeutic agent is enhanced by decreasing mucus elasticity or decreasing mucus viscosity.

In embodiments, penetration of the therapeutic agent is augmented through abnormal mucus by decreasing mucus elasticity or decreasing mucus viscosity of the abnormal mucus. In embodiments, the subject suffers from CF, and penetration of the therapeutic agent into the lung is facilitated by decreasing mucus elasticity or decreasing mucus viscosity of the mucus of the subject suffering CF. In embodiments, penetration of the therapeutic agent is augmented through normal mucus by decreasing mucus elasticity or decreasing mucus viscosity of the normal mucus. In embodiments, the method is useful for oral drug delivery, nasal drug delivery or inhalation drug delivery. In embodiments, administration of a compound disclosed herein in combination with another therapeutic agent provides synergistic treatment for the subject. In embodiments, the other therapeutic agent is a mucolytic (e.g., recombinant human DNAse) or a steroid (e.g., fluticasone, budesonide, beclomethasone, mometasone). In embodiments, as a result of the decrease in mucus elasticity or decrease in mucus viscosity in a subject in need thereof upon administration of a compound disclosed herein, the dosage requirements for the other therapeutic agent are reduced.

In another aspect, there is provided a method for treatment in a subject in need thereof, the method including administering an effective amount of a compound disclosed herein in combination with another therapeutic agent. In embodiments, the "another therapeutic agent" is a beta agonist, an anticholinergic, a corticosteroid, an antibiotic, or a rhDNAse. In embodiments, administration of a compound disclosed herein in combination with another therapeutic agent provides additive or synergistic treatment for the subject and does so with the ease of use of a combination product containing a thiosaccharide and a singularity or plurality (e.g., 1, 2, 3, 4 or even 5) additional active ingredients (i.e., therapeutic agents).

Further to any embodiment disclosed herein, in embodiments, the thiosaccharide mucolytic agent is a thiol monosaccharide mucolytic agent, a thiol disaccharide mucolytic agent, or a thiol trisaccharide mucolytic agent. In embodiments, the thiosaccharide mucolytic agent is a thiol monosaccharide mucolytic agent. In embodiments, the thiosaccharide mucolytic agent is a thiol disaccharide mucolytic agent. In embodiments, the thiosaccharide mucolytic agent is a thiol trisaccharide mucolytic agent.

In embodiments, the thiosaccharide mucolytic agent includes D-glucopyranose, D-galactopyranose, D-mannopyranose, D-glucopyranoside, D-galactopyranoside, or D-mannopyranoside moieties. In embodiments, the thiosaccharide mucolytic agent includes D-galactopyranose. In embodiments, the specific stereochemical structure of the sugar component of the thiosaccharide mucolytic agent can determine the activity in decreasing mucus elasticity or decreasing mucus viscosity in a subject in need thereof.

Further to any embodiment disclosed herein for the method of decreasing mucus elasticity or decreasing mucus viscosity in a subject in need thereof, in embodiments the thiosaccharide mucolytic agent has the formula:

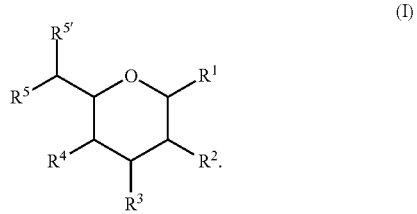

(I)

In embodiments for Formula (I), R is —$SR^{1A}$, —$OR^{1A}$, —$NR^{1B}$ or —$R^{1D}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; $R^{1C}$ is substituted or unsubstituted $C_1$-$C_{10}$ thiol-alkyl or substituted or unsubstituted 2 to 10 membered thiol-heteroalkyl; and $R^{1D}$ is substituted or unsubstituted $C_1$-$C_{10}$ thiol-alkyl or substituted or unsubstituted 2 to 10 membered thiol-heteroalkyl. $R^2$ is —$SR^{2A}$, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^3$ is —$SR^{3A}$, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl. $R^4$ is —$SR^{4A}$, —SAc, —$OR^{4A}$ or —$NR^{4B}$, wherein $R^{4A}$ is H, substituted or unsubstituted $C_1$-$C_{10}$ thiol-alkyl or substituted or unsubstituted 2 to 10 membered thiol-heteroalkyl; $R^{4B}$ is —$C(O)R^{4C}$, substituted or unsubstituted $C_1$-$C_{10}$ thiol-alkyl or substituted or unsubstituted 2 to 10 membered thiol-heteroalkyl; and $R^{4C}$ is substituted or unsubstituted $C_1$-$C_{10}$ thiol-alkyl or substituted or unsubstituted 2 to 10 membered thiol-heteroalkyl. $R^5$ is H, —$SR^{5A}$, —SAc, —$OR^{5A}$, —$NR^{5B}$, or —$R^{5D}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —$C(O)R^{5C}$, substituted or unsubstituted $C_1$-$C_{10}$ thiol-alkyl or substituted or unsubstituted 2 to 10 membered thiol-heteroalkyl; $R^{5C}$ is substituted or unsubstituted $C_1$-$C_{10}$ thiol-alkyl or substituted or unsubstituted 2 to 10 membered thiol-heteroalkyl; $R^{5D}$ is substituted or unsubstituted $C_1$-$C_{10}$ thiol-alkyl; and $R^{5'}$ is H or —OH.

In embodiments for Formula (I), R is —$SR^{1A}$, —$OR^{1A}$, —$NR^{1B}$ or —$R^{1D}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; $R^{1C}$ is substituted or unsubstituted $C_1$-$C_{10}$ thiol-alkyl or substituted or unsubstituted 2 to 10 membered thiol-heteroalkyl; and $R^{1D}$ is substituted or unsubstituted $C_1$-$C_{10}$ thiol-alkyl or substituted or unsubstituted 2 to 10 membered thiol-heteroalkyl. $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^3$ is —SH, —$OR^{3A}$ or —$NR^{3B}$, wherein $R^{3A}$ is H, substituted or unsubstituted $C_1$-$C_{10}$ thiol-alkyl or substituted or unsubsti- In embodiments for Formula (I), $R^1$ is —SH, —$OR^{1A}$, —$NR^{1B}$ or —$R^{1D}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; $R^{1C}$ is substituted or unsubstituted $C_1$-$C_{10}$ thiol-alkyl or substituted or unsubstituted 2 to 10 membered thiol-heteroalkyl; and $R^{1D}$ is substituted or unsubstituted $C_1$-$C_{10}$ thiol-alkyl or substituted or unsubstituted 2 to 10 membered thiol-heteroalkyl. $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^3$ is —SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —C(O)$R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl. $R^4$ is —SH, —SAc, —$OR^{4A}$ or —$NR^{4B}$ wherein $R^{4A}$ is H, substituted or unsubstituted $C_1$-$C_{10}$ thiol-alkyl or substituted or unsubstituted 2 to 10 membered thiol-heteroalkyl; $R^{4B}$ is —C(O)$R^{4C}$, substituted or unsubstituted $C_1$-$C_{10}$ thiol-alkyl or substituted or unsubstituted 2 to 10 membered thiol-heteroalkyl; and $R^{4C}$ is substituted or unsubstituted $C_1$-$C_{10}$ thiol-alkyl or substituted or unsubstituted 2 to 10 membered thiol-heteroalkyl. $R^5$ is H, —SH, —SAc, —$OR^{5A}$, —$NR^{5B}$ or —$R^{5D}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —C(O)$R^{5C}$, substituted or unsubstituted $C_1$-$C_{10}$ thiol-alkyl or substituted or unsubstituted 2 to 10 membered thiol-heteroalkyl; $R^{5C}$ is substituted or unsubstituted $C_1$-$C_{10}$ thiol-alkyl or substituted or unsubstituted 2 to 10 membered thiol-heteroalkyl; $R^{5D}$ is substituted or unsubstituted $C_1$-$C_{10}$ thiol-alkyl; and $R^{5'}$ is H or —OH.

In embodiments, $R^1$, $R^3$, $R^4$ and $R^5$ are —OH, and $R^{5'}$ is H. In embodiments, the thiosaccharide mucolytic agent has the structure of Formula (Ia):

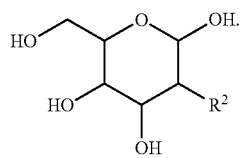

(Ia)

In embodiments, the compound has the structure following:

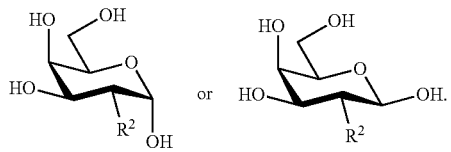

For Formula (Ia), $R^{2A}$ is an unsubstituted $C_1$-$C_{10}$ thiol-alkyl or unsubstituted 2 to 10 membered thiol-heteroalkyl; $R^{2B}$ is —C(O)$R^{2C}$, unsubstituted $C_1$-$C_{10}$ thiol-alkyl or unsubstituted thiol-heteroalkyl; and $R^{2C}$ is substituted or unsubstituted $C_1$-$C_{10}$ thiol-alkyl or substituted or unsubstituted 2 to 10 membered thiol-heteroalkyl.

In embodiments, $R^2$ is —$NR^{2B}$. In embodiments, $R^{2B}$ is —C(O)$R^{2C}$. In embodiments, $R^{2C}$ is $R^{2C1}$-substituted $C_1$-$C_{10}$ thiol-alkyl or $R^{2C1}$-substituted 2 to 10 membered thiol-heteroalkyl, wherein $R^{2C1}$ is —N(H)C(O)$R^{2C2}$, wherein $R^{2C2}$ is unsubstituted $C_1$-$C_{10}$ alkyl. In embodiments, $R^{2C2}$ is methyl. In embodiments, $R^{2A}$ is —N(H)—C(O)—CH(NHAc)—CH$_2$—SH.

In embodiments of Formula (I), $R^2$, $R^3$, $R^4$ are —OH. In embodiments, the thiosaccharide mucolytic agent has the structure of Formula (Ib):

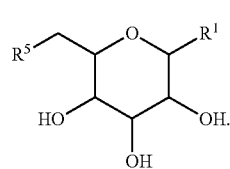

(Ib)

For Formula (Ib), $R^5$ is —SH, —$OR^{5A}$ or —$NR^{5B}$, wherein $R^{5A}$ is unsubstituted $C_1$-$C_{10}$ thiol-alkyl or unsubstituted 2 to 10 membered thiol-heteroalkyl; and $R^{5B}$ is —C(O)$R^{5C}$, unsubstituted $C_1$-$C_{10}$ thiol-alkyl or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl. In embodiments, $R^5$ is —SH. In embodiments, $R^1$ is $OR^{1A}$. In embodiments, $R^{1A}$ is unsubstituted $C_1$-$C_5$ alkyl. In embodiments, $R^{1A}$ is methyl.

Further to Formula (Ib), in embodiments $R^1$ is —$OR^{1A}$, $R^{1A}$ is substituted or unsubstituted $C_1$-$C_{10}$ alkyl, $R^5$ is —$OR^{5A}$, and $R^{5A}$ is substituted or unsubstituted $C_1$-$C_{10}$ thiol-alkyl or substituted or unsubstituted 2 to 10 membered thiol-heteroalkyl. In embodiments, $R^{5A}$ is substituted or unsubstituted $C_1$-$C_{10}$ thiol-alkyl, i.e., —(CH$_2$)$_z$SH, z: 1-10. In embodiments, $R^{5A}$ is unsubstituted $C_1$-$C_{10}$ thiol-alkyl. In embodiments, $R^{5A}$ is thiomethyl (—CH$_2$SH), thioethyl [—(CH$_2$)$_2$SH], thiopropyl [—(CH$_2$)$_3$SH], thiobutyl [—(CH$_2$)$_4$SH], thiopentyl [—(CH$_2$)$_5$SH], thiohexyl [—(CH$_2$)$_6$SH], thioheptyl [—(CH$_2$)$_7$SH], thiooctyl [—(CH$_2$)$_8$SH], thiononyl [—(CH$_2$)$_9$SH] or thiodecyl [—(CH$_2$)$_{10}$SH].

In embodiments of Formula (I), $R^5$ is —OH, $R^1$ is —$OR^{1A}$, and $R^{1A}$ is substituted or unsubstituted $C_1$-$C_{10}$ thiol-alkyl, In embodiments, the thiosaccharide mucolytic agent has the structure of Formula (Ib') following:

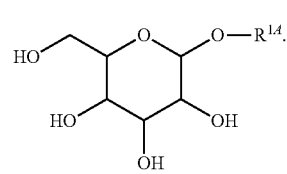

(Ib')

In embodiments, $R^{1A}$ is as defined above. In embodiments, $R^{1A}$ is thiomethyl, thioethyl, thiopropyl, thiobutyl, thiopentyl, thiohexyl, thioheptyl, thiooctyl, thiononyl or thiodecyl. In embodiments, $R^{1A}$ is thioethyl. In embodiments, $R^{1A}$ is thiopentyl.

In embodiments of Formula (I), $R^5$ is —OH, $R^1$ is —$SR^{1A}$, and $R^{1A}$ is substituted or unsubstituted $C_1$-$C_{10}$ thiol-alkyl, In embodiments, the thiosaccharide mucolytic agent has the structure of Formula (Ib") following:

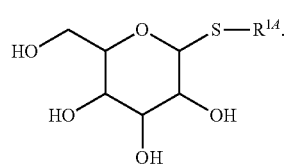

(Ib")

In embodiments, $R^{1A}$ is as defined above. In embodiments, $R^{1A}$ is thiomethyl, thioethyl, thiopropyl, thiobutyl, thiopentyl, thiohexyl, thioheptyl, thiooctyl, thiononyl or thiodecyl. In embodiments, $R^{1A}$ is thioethyl. In embodiments, $R^{1A}$ is thiopentyl.

In embodiments, the compound of Formula (Ib) or Formula (Ib') has the structure following:

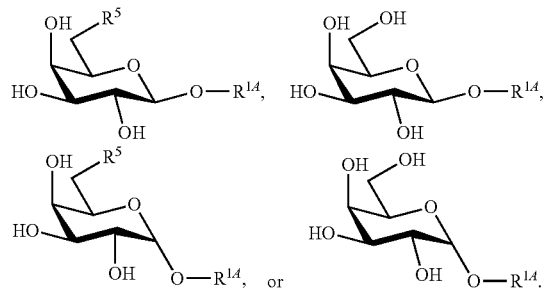

In embodiments of Formula (Ib'), the compound has the structure following:

(2)

(43)

(44)

(45)

In embodiments of Formula (Ib'), $R^{1A}$ is substituted or unsubstituted $C_1$-$C_{10}$ thiol-alkyl, wherein the $C_1$-$C_{10}$ thiol-alkyl contains a double bond or a triple bond (e.g., a $C_1$-$C_{10}$ thiol-unsaturated alkyl. In embodiments, $R^{1A}$ is unsubstituted $C_1$-$C_{10}$ thiol-alkyl, wherein the $C_1$-$C_{10}$ thiol-alkyl contains a double bond or a triple bond. In embodiments, the compound has the structure following:

(49)

Further to Formula (Ib), in embodiments $R^1$ is —$OR^{1A}$, $R^{1A}$ is H, or substituted or unsubstituted $C_1$-$C_{10}$ alkyl, $R^5$ is —$OR^{5A}$, and $R^{5A}$ is substituted or unsubstituted $C_1$-$C_{10}$ thiol-alkyl or substituted or unsubstituted 2 to 10 membered thiol-heteroalkyl. In embodiments, $R^{5A}$ is substituted or unsubstituted $C_1$-$C_{10}$ thiol-alkyl. In embodiments, $R^{5A}$ is unsubstituted $C_1$-$C_{10}$ thiol-alkyl. In embodiments, $R^{5A}$ is thiomethyl, thioethyl, thiopropyl, thiobutyl, thiopentyl, thiohexyl, thioheptyl, thiooctyl, thiononyl or thiodecyl. In embodiments, the compound has the structure following:

(46)

Further to Formula (Ib), in embodiments $R^5$ is —OH, and $R^1$ is $R^{1D}$. $R^{1D}$ is substituted or unsubstituted $C_1$-$C_{10}$ thiol-alkyl or substituted or unsubstituted 2 to 10 membered thiol-heteroalkyl. In embodiments, $R^{1D}$ is substituted or unsubstituted $C_1$-$C_{10}$ thiol-alkyl. In embodiments, $R^{1D}$ is unsubstituted $C_1$-$C_{10}$ thiol-alkyl. In embodiments, $R^{1D}$ is thiomethyl, thioethyl, thiopropyl, thiobutyl, thiopentyl, thiohexyl, thioheptyl, thiooctyl, thiononyl or thiodecyl.

In embodiments, the compound has the structure following:

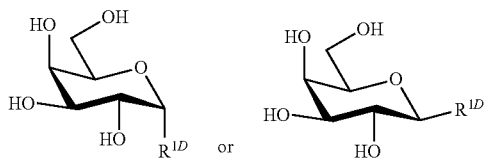

In embodiments, the compound has the structure following:

(47)

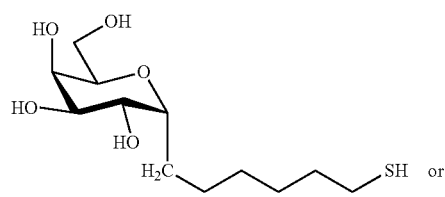

In embodiments of Formula (I), $R^3$, $R^4$, $R^5$ are —OH, $R^{5'}$ is H, and the thiosaccharide mucolytic agent has the structure of Formula (Ic):

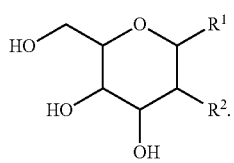

(Ic)

In embodiments of Formula (Ic), the compound has the structure following:

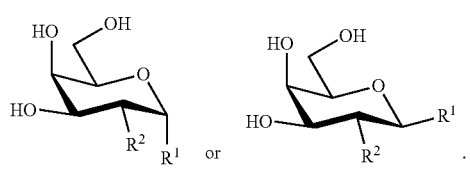

In embodiments, $R^2$ is —OH. In embodiments, $R^1$ is —SH, —OR$^{1A}$ or —NR$^{1B}$, wherein $R^{1A}$ is unsubstituted $C_1$-$C_{10}$ thiol-alkyl or unsubstituted 2 to 10 membered thiol-heteroalkyl; $R^{1B}$ is —C(O)R$^{1C}$, unsubstituted $C_1$-$C_{10}$ thiol-alkyl or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl. In embodiments, R is —OR$^{1A}$ and $R^{1A}$ is unsubstituted $C_1$-$C_{10}$ thiol-alkyl.

In embodiments, R is —OH. In embodiments, $R^2$ is —SH, —OR$^{2A}$ or —NR$^{2B}$, wherein $R^{2A}$ is unsubstituted $C_1$-$C_{10}$ thiol-alkyl or unsubstituted 2 to 10 membered thiol-heteroalkyl; $R^{2B}$ is —C(O)R$^{2C}$, unsubstituted $C_1$-$C_{10}$ thiol-alkyl or unsubstituted 2 to 10 membered thiol-heteroalkyl; and $R^{2C}$ is substituted or unsubstituted $C_1$-$C_{10}$ thiol-alkyl or substituted or unsubstituted 2 to 10 membered thiol-heteroalkyl. In embodiments, $R^2$ is —NR$^{2B}$, and $R^{2B}$ is —C(O)R$^{2C}$. In embodiments, $R^{2C}$ is unsubstituted $C_1$-$C_{10}$ thiol-alkyl.

In embodiments, $R^4$ is —SH, and the thiosaccharide mucolytic agent has the structure of Formula (Id):

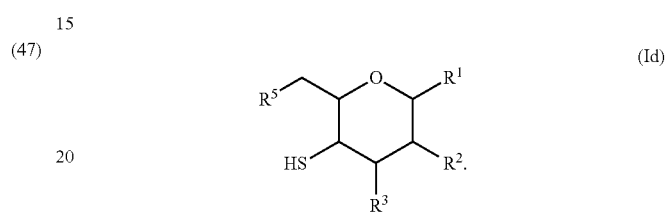

(Id)

In embodiments of Formula (Id), the compound has the structure following:

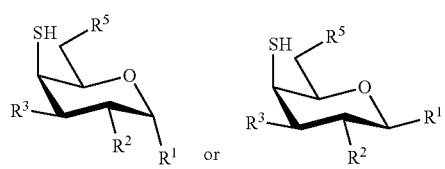

Further to Formula (Id), in embodiments $R^1$ is —OR$^{1A}$, and $R^2$, $R^3$, and $R^5$ are —OH. In embodiments, $R^{1A}$ is unsubstituted $C_1$-$C_{10}$ alkyl. In embodiments, $R^{1A}$ is methyl.

In embodiments of Formula (I), $R^5$ is —SH, and $R^{5'}$ is H, and the thiosaccharide mucolytic agent has the structure of Formula (Ie):

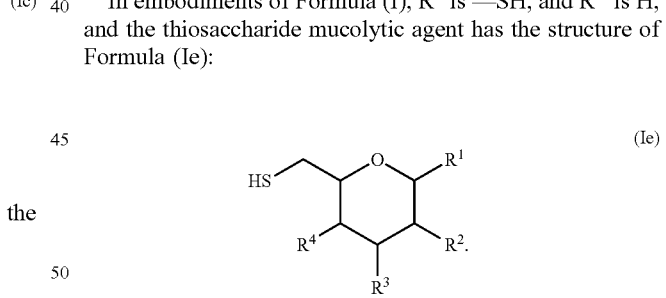

(Ie)

In embodiments of Formula (Ie), the compound has the structure following:

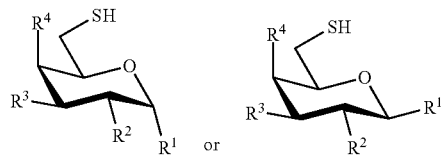

Further to Formula (Ie), in embodiments $R^1$ is —OR$^{1A}$, and $R^2$, $R^3$, and $R^4$ are —OH, and the compound has the structure of Formula (Ie'):

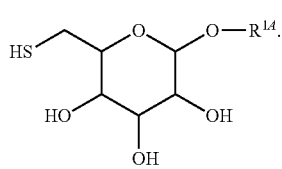

(Ie')

In embodiments of Formula (Ie'), the compound has the structure following:

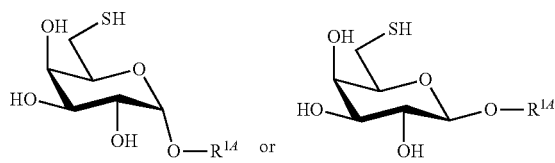

In embodiments for Formula (Ie'), $R^{1A}$ is unsubstituted $C_1$-$C_{10}$ alkyl. In embodiments, $R^{1A}$ is methyl. In embodiments, the compound has the structure following:

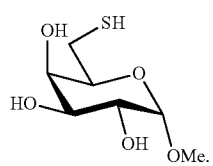

(1)

Yet further to Formula (Ie), in embodiments $R^1$ is —$OR^{1A}$, $R^2$, $R^3$, and $R^4$ are —OH, and $R^{1A}$ is substituted or unsubstituted $C_1$-$C_{10}$ thiol-alkyl or substituted or unsubstituted 2 to 10 membered thiol-heteroalkyl. In embodiments, $R^{1A}$ is substituted or unsubstituted $C_1$-$C_{10}$ thiol-alkyl. In embodiments, $R^{1A}$ is unsubstituted $C_1$-$C_{10}$ thiol-alkyl. In embodiments, $R^{1A}$ is thiomethyl, thioethyl, thiopropyl, thiobutyl, thiopentyl, thiohexyl, thioheptyl, thiooctyl, thiononyl or thiodecyl. In embodiments, $R^{1A}$ is thiopentyl.

In embodiments, the compound has the structure following:

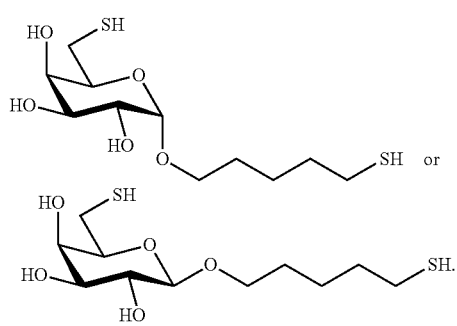

(42)

In embodiments of Formula (I), $R^1$ is —$OR^{1A}$, $R^2$, $R^3$, and $R^4$ are —OH, $R^5$ is H or —$OR^{5A}$, $R^{5'}$ is H, and the thiosaccharide mucolytic agent has the structure of Formula (If):

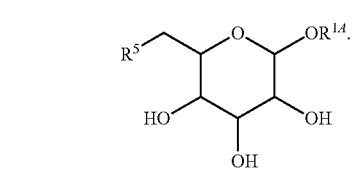

(If)

In embodiments of Formula (If), the compound has the structure following:

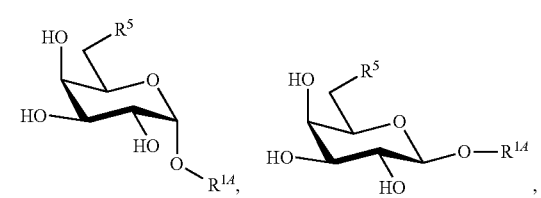

Further to Formula (If), in embodiments, $R^5$ is H. In embodiments, $R^{1A}$ is substituted or unsubstituted $C_1$-$C_{10}$ thiol-alkyl or substituted or unsubstituted 2 to 10 membered thiol-heteroalkyl. In embodiments, $R^{1A}$ is unsubstituted $C_1$-$C_{10}$ thiol-alkyl. In embodiments, $R^{1A}$ is thiopropyl.

Yet further to Formula (If), in embodiments, $R^5$ is —$OR^{5A}$. In embodiments, $R^5$ is —OH. In embodiments, $R^{1A}$ is unsubstituted $C_1$-$C_{10}$ thiol-alkyl. In embodiments, $R^{1A}$ is thiopropyl.

Yet even further to Formula (If), in embodiments, $R^{1A}$ is substituted or unsubstituted $C_1$-$C_{10}$ thiol-alkyl or substituted or unsubstituted 2 to 10 membered thiol-heteroalkyl. In embodiments, $R^5$ is —OH, and $R^{1A}$ is or unsubstituted $C_1$-$C_{10}$ thiol-alkyl or unsubstituted 2 to 10 membered thiol-heteroalkyl. In embodiments, $R^{1A}$ is unsubstituted $C_1$-$C_{10}$ thiol-alkyl. In embodiments, $R^{1A}$ is thioethyl, thiopropyl, thiobutyl, or thiopentyl. In embodiments, $R^{1A}$ is unsubstituted 2 to 10 membered thiol-heteroalkyl. In embodiments, $R^{1A}$ is thioethyloxyethyl.

In embodiments, R is —$OR^{1A}$, $R^2$, $R^3$, and $R^4$ are —OH, $R^{5'}$ is H, $R^5$ is —SH, and the thiosaccharide mucolytic agent has the structure of Formula (Ig):

(Ig)

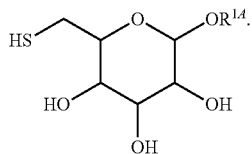

In embodiments, the compound has the structure following:

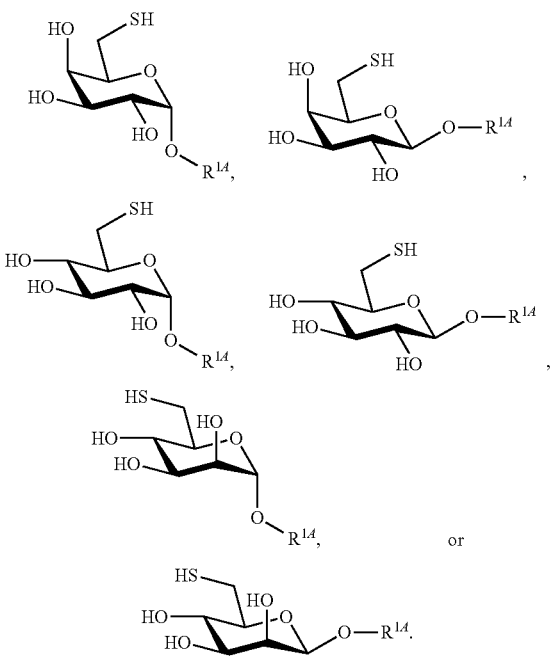

In embodiments, $R^1$ is $-OR^{1A}$, $R^2$, $R^3$, and $R^4$ are $-OH$, $R^5$ is $-SAc$, $R^{5'}$ is H, and the thiosaccharide mucolytic agent has the structure of Formula (Ih):

(Ih)

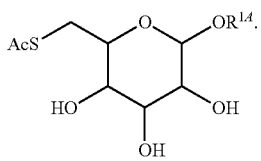

In embodiments, the compound has the structure following:

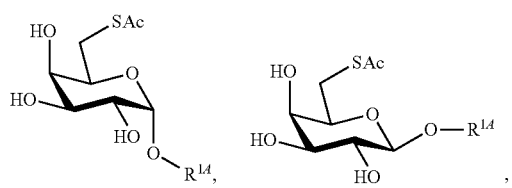

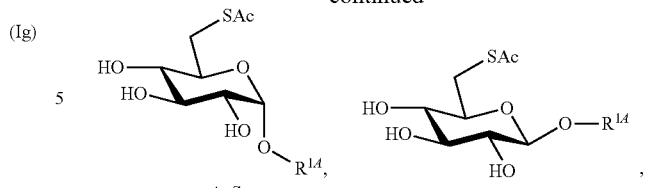

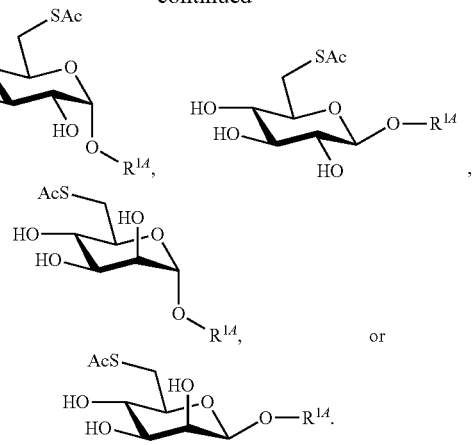

Further to Formula (Ih), in embodiments, wherein $R^{1A}$ is methyl.

In embodiments, the compound has the structure following:

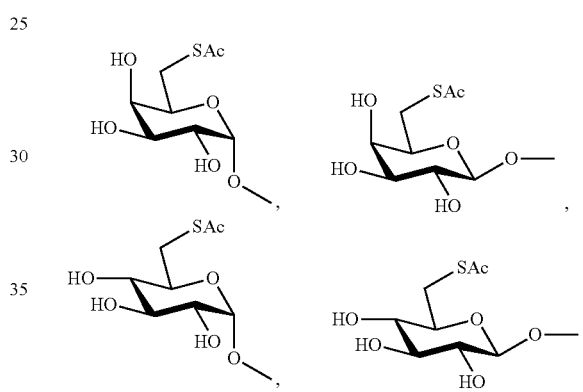

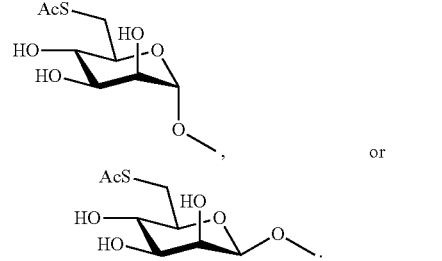

In embodiments of Formula (I), $R^1$ is $-OR^{1A}$ or $-R^{1D}$, $R^2$ is $-OH$ or $-NR^{2B}$, $R^{2B}$ is $-C(O)R^{2C}$, $R^{2C}$ is substituted or unsubstituted $C_1$-$C_{10}$ alkyl, $R^3$ and $R^4$ are $-OH$, $R^5$ is $-OR^{5A}$ or $-R^{5D}$, and the thiosaccharide mucolytic agent has the structure of Formula (Ii):

(Ii)

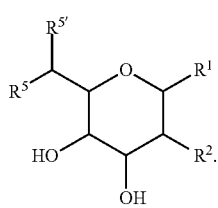

In embodiments, the compound has the structure following:

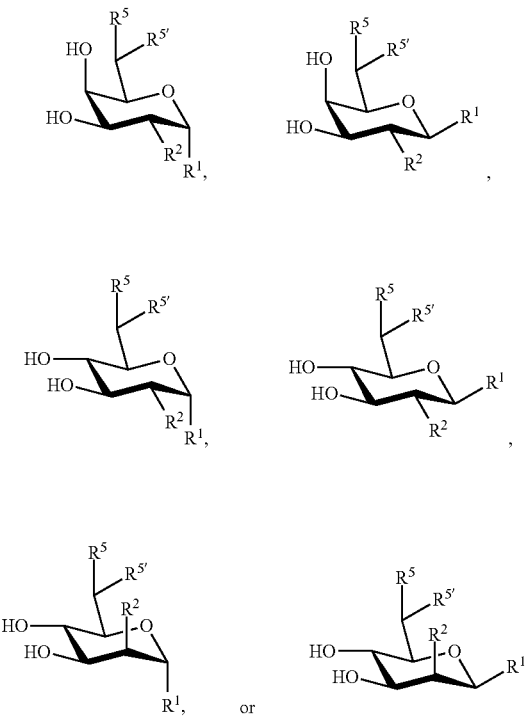

Yet further to Formula (i), in embodiments $R^2$ is —OH. In embodiments, $R^2$ is —$NR^{2B}$. In embodiments, $R^2$ is —NHAc.

Further to any embodiment disclosed herein for the method of decreasing mucus elasticity or decreasing mucus viscosity in a subject in need thereof, in embodiments the thiosaccharide mucolytic agent has the formula following, wherein $R^1$, $R^2$, $R^3$ and $R^4$ are as defined for Formula (I):

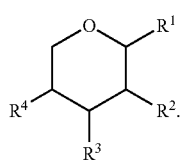
(VI)

In embodiments of Formula (VI), $R^1$ is —$OR^{1A}$, $R^2$ and $R^3$ are —OH, $R^4$ is —SH, and the compound has the structure of Formula (VIa):

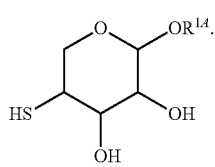
(VIa)

In embodiments, the compound has the structure following:

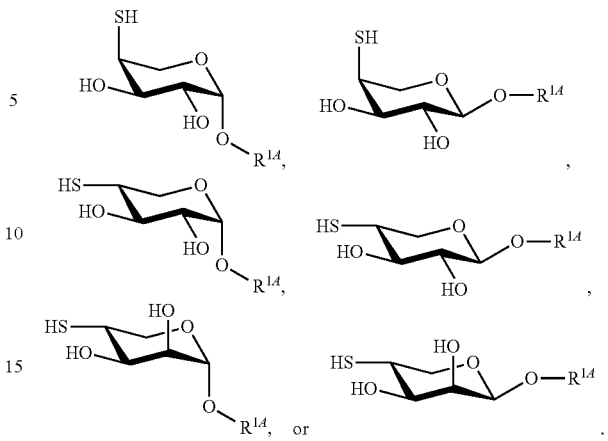

In embodiments of Formula (VIa), $R^{1A}$ is unsubstituted $C_1$-$C_5$ alkyl. In embodiments, $R^{1A}$ is methyl.

In embodiments for Formula (VI), $R^1$ is —$OR^{1A}$, and $R^2$, $R^3$ and $R^4$ are —OH. In embodiments, $R^{1A}$ is or unsubstituted $C_1$-$C_{10}$ thiol-alkyl or unsubstituted 2 to 10 membered thiol-heteroalkyl. In embodiments, $R^{1A}$ is unsubstituted $C_1$-$C_{10}$ thiol-alkyl. In embodiments, $R^{1A}$ is thioethyl, thiopropyl, thiobutyl, or thiopentyl.

In embodiments, $R^1$ is —$OR^{1A}$, $R^2$ and $R^3$ are —OH, $R^4$ is —SAc, and the compound has the structure of Formula (VIb):

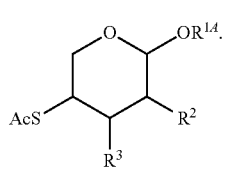
(VIb)

In embodiments, the compound has the structure following:

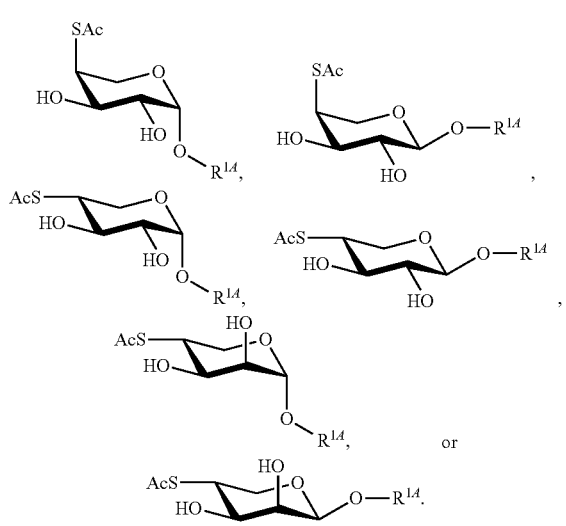

Further to the method of decreasing mucus elasticity or decreasing mucus viscosity in a subject in need thereof, wherein the method includes administering to the subject a thiosaccharide mucolytic agent, in embodiments the thiosaccharide mucolytic agent has the structure of Formula (VII) following, wherein $R^1$, $R^2$, $R^3$ and $R^4$ are as defined for Formula (I).

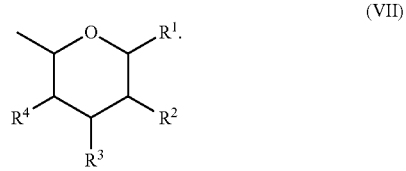

(VII)

In embodiments, the compound has the structure following:

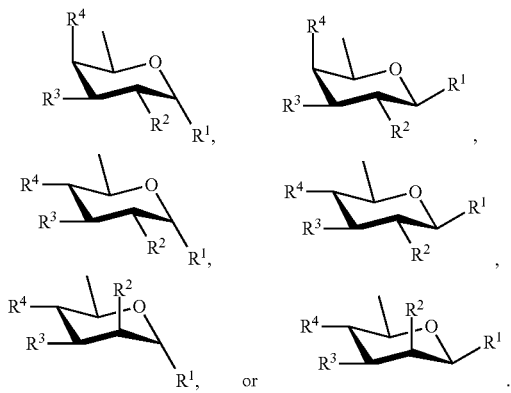

Regarding Formula (VII), in embodiments $R^1$ is —$OR^{1A}$, $R^2$, $R^3$ and $R^4$ are —OH, and the compound as the structure following:

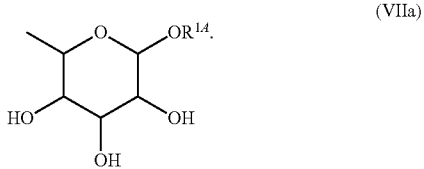

(VIIa)

In embodiments, the compound of Formula (VIIa) has the structure following:

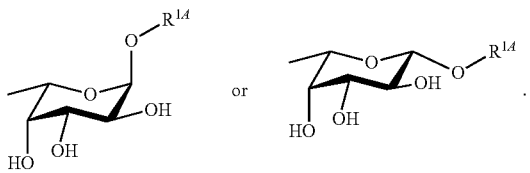

In embodiments of the compound of Formula (VIIa), $R^{1A}$ is substituted or unsubstituted $C_1$-$C_{10}$ thiol-alkyl. In embodiments, $R^{1A}$ is unsubstituted $C_1$-$C_{10}$ thiol-alkyl. In embodiments, $R^{1A}$ is thiomethyl, thioethyl, thiopropyl, thiobutyl, thiopentyl, thiohexyl, thioheptyl, thiooctyl, thiononyl or thiodecyl. In embodiments, $R^{1A}$ is thioethyl. In embodiments, $R^{1A}$ is thiopentyl.

In embodiments, the compound has the structure following:

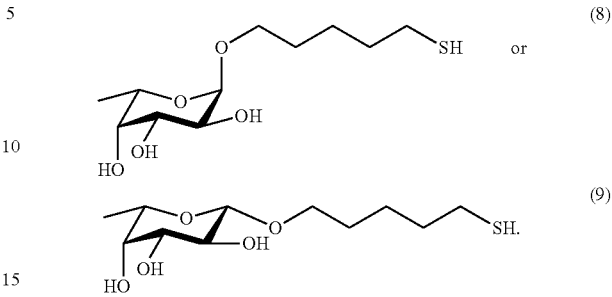

(8)

or (9)

Further to the method of decreasing mucus elasticity or decreasing mucus viscosity in a subject in need thereof, wherein the method includes administering to the subject a thiosaccharide mucolytic agent, in embodiments the thiosaccharide mucolytic agent has the formula:

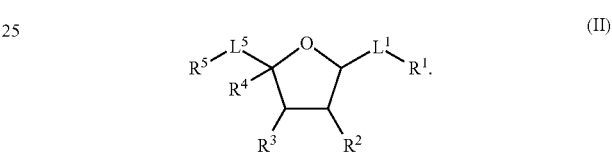

(II)

Regarding Formula (II), $L^1$ and $L^5$ are independently a bond or methylene. $R^1$ is —SH, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl, $R^{1B}$ is —$C(O)R^{1C}$, substituted or unsubstituted $C_1$-$C_{10}$ thiol-alkyl or substituted or unsubstituted 2 to 10 membered thiol-heteroalkyl, and $R^{1C}$ is substituted or unsubstituted $C_1$-$C_{10}$ thiol-alkyl or substituted or unsubstituted 2 to 10 membered thiol-heteroalkyl. $R^2$—SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl, $R^{2B}$ is —$C(O)R^{2C}$, substituted or unsubstituted $C_1$-$C_{10}$ thiol-alkyl or substituted or unsubstituted 2 to 10 membered thiol-heteroalkyl, and $R^{2C}$ is substituted or unsubstituted $C_1$-$C_{10}$ thiol-alkyl or substituted or unsubstituted 2 to 10 membered thiol-heteroalkyl. $R^3$—SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl, $R^{3B}$ is —$C(O)R^{3C}$, substituted or unsubstituted $C_1$-$C_{10}$ thiol-alkyl or substituted or unsubstituted 2 to 10 membered thiol-heteroalkyl, and $R^{3C}$ is substituted or unsubstituted $C_1$-$C_{10}$ thiol-alkyl or substituted or unsubstituted 2 to 10 membered thiol-heteroalkyl. $R^4$—SH, —$OR^{4A}$ or —$NR^{4B}$, wherein $R^{4A}$ is H, substituted or unsubstituted $C_1$-$C_{10}$ thiol-alkyl or substituted or unsubstituted 2 to 10 membered thiol-heteroalkyl, $R^{4B}$ is —$C(O)R^{4C}$, substituted or unsubstituted $C_1$-$C_{10}$ thiol-alkyl or substituted or unsubstituted 2 to 10 membered thiol-heteroalkyl, and $R^{4C}$ is substituted or unsubstituted $C_1$-$C_{10}$ thiol-alkyl or substituted or unsubstituted 2 to 10 membered thiol-heteroalkyl. $R^5$ is H, —SH, —$OR^{5A}$ or —$NR^{5B}$, wherein $R^{5A}$ is H, substituted or unsubstituted $C_1$-$C_{10}$ thiol-alkyl or substituted or unsubstituted 2 to 10 membered thiol-heteroalkyl, $R^{5B}$ is —$C(O)R^{5C}$, substituted or unsubstituted $C_1$-$C_{10}$ thiol-alkyl or substituted or unsubstituted 2 to 10 membered thiol-heteroalkyl, and $R^{5C}$ is substituted or unsubstituted $C_1$-$C_{10}$ thiol-alkyl or substituted or unsubstituted 2 to 10 membered thiol-heteroalkyl.

In yet another embodiment of the method, the thiosaccharide mucolytic agent has the formula:

$$\text{(III)}$$

In embodiments of Formula (III), $R^1$ is —$SR^{1A}$, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl, $R^{1B}$ is —$C(O)R^{1C}$, substituted or unsubstituted $C_1$-$C_{10}$ thiol-alkyl or substituted or unsubstituted 2 to 10 membered thiol-heteroalkyl, and $R^{1C}$ is substituted or unsubstituted $C_1$-$C_{10}$ thiol-alkyl or substituted or unsubstituted 2 to 10 membered thiol-heteroalkyl. $R^2$ is —$SR^{2A}$, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl, $R^{2B}$ is —$C(O)R^{2C}$, substituted or unsubstituted $C_1$-$C_{10}$ thiol-alkyl or substituted or unsubstituted 2 to 10 membered thiol-heteroalkyl, and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^3$ is —$SR^{3A}$, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl, $R^{3B}$ is —$C(O)R^{3C}$, substituted or unsubstituted $C_1$-$C_{10}$ thiol-alkyl or substituted or unsubstituted 2 to 10 membered thiol-heteroalkyl, and $R^{3C}$ is substituted or unsubstituted $C_1$-$C_{10}$ thiol-alkyl or substituted or unsubstituted 2 to 10 membered thiol-heteroalkyl. $R^5$ is H, —$SR^{5A}$, —SAc, —$OR^{5A}$ or —$NR^{5B}$, wherein $R^{5A}$ is H, substituted or unsubstituted $C_1$-$C_{10}$ thiol-alkyl or substituted or unsubstituted 2 to 10 membered thiol-heteroalkyl, $R^{5B}$ is —$C(O)R^{5C}$, substituted or unsubstituted $C_1$-$C_{10}$ thiol-alkyl or substituted or unsubstituted 2 to 10 membered thiol-heteroalkyl, and $R^{5C}$ is substituted or unsubstituted $C_1$-$C_{10}$ thiol-alkyl or substituted or unsubstituted 2 to 10 membered thiol-heteroalkyl. $R^7$ is —$SR^{7A}$, —$OR^{7A}$ or —$NR^{7B}$, wherein $R^{7A}$ is H, substituted or unsubstituted $C_1$-$C_{10}$ thiol-alkyl or substituted or unsubstituted 2 to 10 membered thiol-heteroalkyl, $R^{7B}$ is —$C(O)R^{7C}$, substituted or unsubstituted $C_1$-$C_{10}$ thiol-alkyl or substituted or unsubstituted 2 to 10 membered thiol-heteroalkyl, and $R^{7C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^8$ is —$SR^{8A}$, —$OR^{8A}$ or —$NR^{8B}$, wherein $R^{8A}$ is H, substituted or unsubstituted $C_1$-$C_{10}$ thiol-alkyl or substituted or unsubstituted 2 to 10 membered thiol-heteroalkyl, $R^{8B}$ is —$C(O)R^{8C}$, substituted or unsubstituted $C_1$-$C_{10}$ thiol-alkyl or substituted or unsubstituted 2 to 10 membered thiol-heteroalkyl, and $R^{8C}$ is substituted or unsubstituted $C_1$-$C_{10}$ thiol-alkyl or substituted or unsubstituted 2 to 10 membered thiol-heteroalkyl. $R^9$ is —$SR^{9A}$, —$OR^{9A}$ or —$NR^{9B}$, wherein $R^{9A}$ is H, substituted or unsubstituted $C_1$-$C_{10}$ thiol-alkyl or substituted or unsubstituted 2 to 10 membered thiol-heteroalkyl, $R^{9B}$ is —$C(O)R^{9C}$, substituted or unsubstituted $C_1$-$C_{10}$ thiol-alkyl or substituted or unsubstituted 2 to 10 membered thiol-heteroalkyl, and $R^{9C}$ is substituted or unsubstituted $C_1$-$C_{10}$ thiol-alkyl or substituted or unsubstituted 2 to 10 membered thiol-heteroalkyl. $R^{10}$ is H, —$SR^{10A}$, —SAc, —$OR^{10A}$ or —$NR^{10B}$, wherein $R^{10A}$ is H, substituted or unsubstituted $C_1$-$C_{10}$ thiol-alkyl or substituted or unsubstituted 2 to 10 membered thiol-heteroalkyl, $R^{10B}$ is —$C(O)R^{10C}$, substituted or unsubstituted $C_1$-$C_{10}$ thiol-alkyl or substituted or unsubstituted 2 to 10 membered thiol-heteroalkyl, and $R^{10C}$ is substituted or unsubstituted $C_1$-$C_{10}$ thiol-alkyl or substituted or unsubstituted 2 to 10 membered thiol-heteroalkyl.

In embodiments of Formula (III), $R^1$ is —$SR^{1A}$, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl, $R^{1B}$ is —$C(O)R^{1C}$, substituted or unsubstituted $C_1$-$C_{10}$ thiol-alkyl or substituted or unsubstituted 2 to 10 membered thiol-heteroalkyl, and $R^{1C}$ is substituted or unsubstituted $C_1$-$C_{10}$ thiol-alkyl or substituted or unsubstituted 2 to 10 membered thiol-heteroalkyl. $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl, $R^{2B}$ is —$C(O)R^{2C}$, substituted or unsubstituted $C_1$-$C_{10}$ thiol-alkyl or substituted or unsubstituted 2 to 10 membered thiol-heteroalkyl, and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^3$ is —SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl, $R^{3B}$ is —$C(O)R^{3C}$, substituted or unsubstituted $C_1$-$C_{10}$ thiol-alkyl or substituted or unsubstituted 2 to 10 membered thiol-heteroalkyl, and $R^{3C}$ is substituted or unsubstituted $C_1$-$C_{10}$ thiol-alkyl or substituted or unsubstituted 2 to 10 membered thiol-heteroalkyl. $R^5$ is H, —SH, —SAc, —$OR^{5A}$ or —$NR^{5B}$, wherein $R^{5A}$ is H, substituted or unsubstituted $C_1$-$C_{10}$ thiol-alkyl or substituted or unsubstituted 2 to 10 membered thiol-heteroalkyl, $R^{5B}$ is —$C(O)R^{5C}$, substituted or unsubstituted $C_1$-$C_{10}$ thiol-alkyl or substituted or unsubstituted 2 to 10 membered thiol-heteroalkyl, and $R^{5C}$ is substituted or unsubstituted $C_1$-$C_{10}$ thiol-alkyl or substituted or unsubstituted 2 to 10 membered thiol-heteroalkyl. $R^7$ is —SH, —$OR^{7A}$ or —$NR^{7B}$, wherein $R^{7A}$ is H, substituted or unsubstituted $C_1$-$C_{10}$ thiol-alkyl or substituted or unsubstituted 2 to 10 membered thiol-heteroalkyl, $R^{7B}$ is —$C(O)R^{7C}$, substituted or unsubstituted $C_1$-$C_{10}$ thiol-alkyl or substituted or unsubstituted 2 to 10 membered thiol-heteroalkyl, and $R^{7C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^8$ is —SH, —$OR^{8A}$ or —$NR^{8B}$, wherein $R^{8A}$ is H, substituted or unsubstituted $C_1$-$C_{10}$ thiol-alkyl or substituted or unsubstituted 2 to 10 membered thiol-heteroalkyl, $R^{8B}$ is —$C(O)R^{8C}$, substituted or unsubstituted $C_1$-$C_{10}$ thiol-alkyl or substituted or unsubstituted 2 to 10 membered thiol-heteroalkyl, and $R^{8C}$ is substituted or unsubstituted $C_1$-$C_{10}$ thiol-alkyl or substituted or unsubstituted 2 to 10 membered thiol-heteroalkyl. $R^9$ is —SH, —$OR^{9A}$ or —$NR^{9B}$, wherein $R^{9A}$ is H, substituted or unsubstituted $C_1$-$C_{10}$ thiol-alkyl or substituted or unsubstituted 2 to 10 membered thiol-heteroalkyl, $R^{9B}$ is —$C(O)R^{9C}$, substituted or unsubstituted $C_1$-$C_{10}$ thiol-alkyl or substituted or unsubstituted 2 to 10 membered thiol-heteroalkyl, and $R^{9C}$ is substituted or unsubstituted $C_1$-$C_{10}$ thiol-alkyl or substituted or unsubstituted 2 to 10 membered thiol-heteroalkyl. $R^{10}$ is H, —SH, —SAc, —OR$^{10A}$ or —NR$^{10B}$, wherein $R^{10A}$ is H, substituted or unsubstituted $C_1$-$C_{10}$ thiol-alkyl or substituted or unsubstituted 2 to 10 membered thiol-heteroalkyl, $R^{10B}$ is —C(O)R$^{10C}$, substituted or unsubstituted $C_1$-$C_{10}$ thiol-alkyl or substituted or unsubstituted 2 to 10 membered thiol-heteroalkyl, and Roc is substituted or unsubstituted $C_1$-$C_{10}$ thiol-alkyl or substituted or unsubstituted 2 to 10 membered thiol-heteroalkyl.

In embodiments of Formula (III), $R^1$ is —SH, —OR$^{1A}$ or —NR$^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl, $R^{1B}$ is —C(O)R$^{1C}$, substituted or unsubstituted $C_1$-$C_{10}$ thiol-alkyl or substituted or unsubstituted 2 to 10 membered thiol-heteroalkyl, and $R^{1C}$ is substituted or unsubstituted $C_1$-$C_{10}$ thiol-alkyl or substituted or unsubstituted 2 to 10 membered thiol-heteroalkyl. $R^2$ is —SH, —OR$^{2A}$ or —NR$^{2B}$, wherein $R^{2A}$ is H, substituted or unsubstituted $C_1$-$C_{10}$ thiol-alkyl or substituted or unsubstituted 2 to 10 membered thiol-heteroalkyl, $R^{2B}$ is —C(O)R$^{2C}$, substituted or unsubstituted $C_1$-$C_{10}$ thiol-alkyl or substituted or unsubstituted 2 to 10 membered thiol-heteroalkyl, and $R^{2C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl. $R^3$ is —SH, —OR$^{3A}$ or —NR$^{3B}$, wherein $R^{3A}$ is H, substituted or unsubstituted $C_1$-$C_{10}$ thiol-alkyl or substituted or unsubstituted 2 to 10 membered thiol-heteroalkyl, $R^{3B}$ is —C(O)R$^{3C}$, substituted or unsubstituted $C_1$-$C_{10}$ thiol-alkyl or substituted or unsubstituted 2 to 10 membered thiol-heteroalkyl, and $R^{3C}$ is substituted or unsubstituted $C_1$-$C_{10}$ thiol-alkyl or substituted or unsubstituted 2 to 10 membered thiol-heteroalkyl. $R^5$ is H, —SH, —SAc, —OR$^{5A}$ or —NR$^{5B}$, wherein $R^{5A}$ is H, substituted or unsubstituted $C_1$-$C_{10}$ thiol-alkyl or substituted or unsubstituted 2 to 10 membered thiol-heteroalkyl, $R^{5B}$ is —C(O)R$^{5C}$, substituted or unsubstituted $C_1$-$C_{10}$ thiol-alkyl or substituted or unsubstituted 2 to 10 membered thiol-heteroalkyl, and $R^{5C}$ is substituted or unsubstituted $C_1$-$C_{10}$ thiol-alkyl or substituted or unsubstituted 2 to 10 membered thiol-heteroalkyl. $R^7$ is —SH, —OR$^{7A}$ or —NR$^{7B}$, wherein $R^{7A}$ is H, substituted or unsubstituted $C_1$-$C_{10}$ thiol-alkyl or substituted or unsubstituted 2 to 10 membered thiol-heteroalkyl, $R^{7B}$ is —C(O)R$^{7C}$, substituted or unsubstituted $C_1$-$C_{10}$ thiol-alkyl or substituted or unsubstituted 2 to 10 membered thiol-heteroalkyl, and $R^{7C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^8$ is —SH, —OR$^{7A}$ or —NR$^{7B}$, wherein $R^{8A}$ is H, substituted or unsubstituted $C_1$-$C_{10}$ thiol-alkyl or substituted or unsubstituted 2 to 10 membered thiol-heteroalkyl, $R^{8B}$ is —C(O)R$^{8C}$, substituted or unsubstituted $C_1$-$C_{10}$ thiol-alkyl or substituted or unsubstituted 2 to 10 membered thiol-heteroalkyl, and $R^{8C}$ is substituted or unsubstituted $C_1$-$C_{10}$ thiol-alkyl or substituted or unsubstituted 2 to 10 membered thiol-heteroalkyl. $R^9$ is —SH, —OR$^{9A}$ or —NR$^{9B}$, wherein $R^{9A}$ is H, substituted or unsubstituted $C_1$-$C_{10}$ thiol-alkyl or substituted or unsubstituted 2 to 10 membered thiol-heteroalkyl, $R^{9B}$ is —C(O)R$^{9C}$, substituted or unsubstituted $C_1$-$C_{10}$ thiol-alkyl or substituted or unsubstituted 2 to 10 membered thiol-heteroalkyl, and $R^{9C}$ is substituted or unsubstituted $C_1$-$C_{10}$ thiol-alkyl or substituted or unsubstituted 2 to 10 membered thiol-heteroalkyl. $R^{10}$ is H, —SH, —SAc, —OR$^{9A}$ or —NR$^{9B}$, wherein $R^{10A}$ is H, substituted or unsubstituted $C_1$-$C_{10}$ thiol-alkyl or substituted or unsubstituted 2 to 10 membered thiol-heteroalkyl, $R^{10B}$ is —C(O)R$^{10C}$, substituted or unsubstituted $C_1$-$C_{10}$ thiol-alkyl or substituted or unsubstituted 2 to 10 membered thiol-heteroalkyl, and $R^{10C}$ is substituted or unsubstituted $C_1$-$C_{10}$ thiol-alkyl or substituted or unsubstituted 2 to 10 membered thiol-heteroalkyl.

In embodiments of Formula (III), $R^1$ is —OR$^{14}$, $R^2$, $R^3$, $R^5$, $R^7$, $R^8$, and $R^9$ are —OH, $R^{10}$ is —SH or —OR$^{10A}$, and the thiosaccharide mucolytic agent has Formula (IIIa):

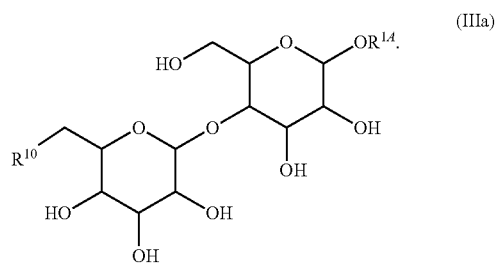

In embodiments of Formula (IIIa), the compound has the structure following:

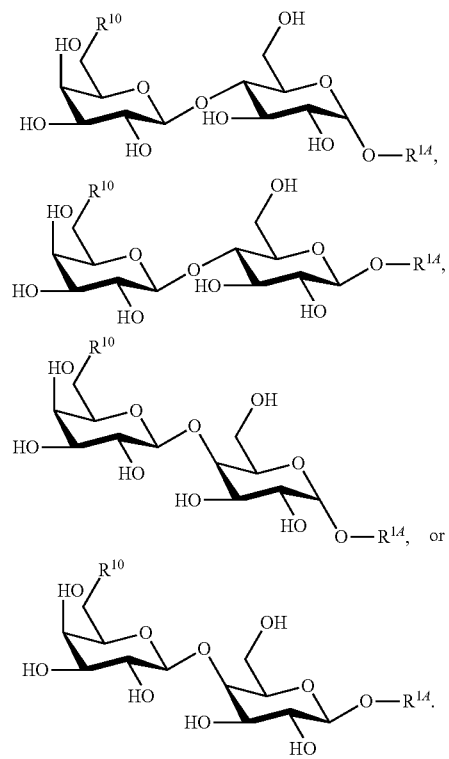

In embodiments of Formula (IIIa), $R^{10}$ is —SH. In embodiments, the compound has the structure

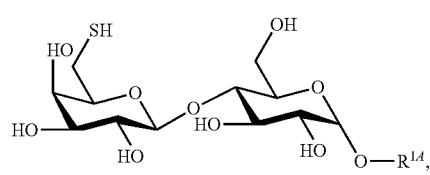

-continued

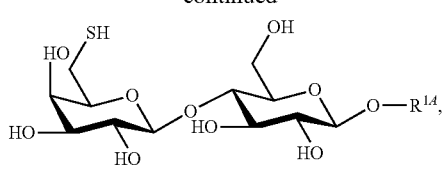

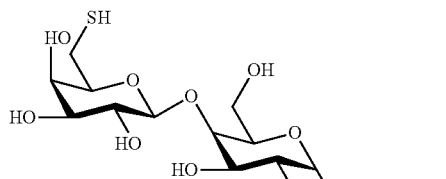

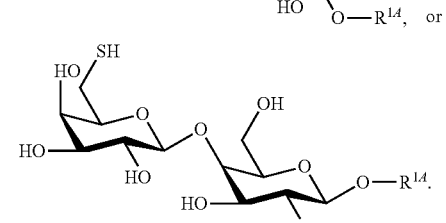

In embodiments of Formula (IIIa), $R^1$ is —OH, and $R^{10}$ is —SH. In embodiments, the compound has the structure following:

(38)

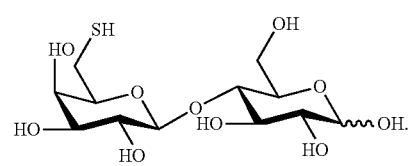

In further embodiments of Formula (IIIa), the compound has the structure following:

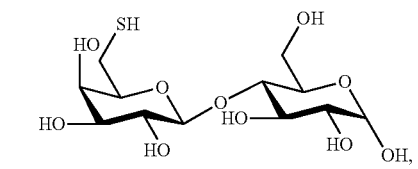

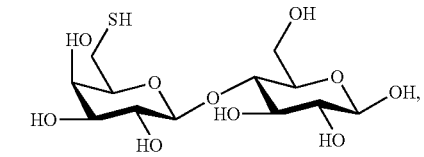

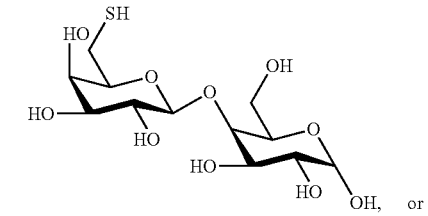

-continued

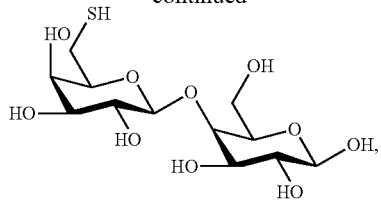

In embodiments of Formula (IIIa), $R^{14}$ is substituted or unsubstituted $C_1$-$C_{10}$ thiol-alkyl or substituted or unsubstituted 2 to 10 membered thiol-heteroalkyl. In embodiments, $R^{14}$ is substituted or unsubstituted $C_1$-$C_{10}$ thiol-alkyl. In embodiments, $R^{14}$ is unsubstituted $C_1$-$C_{10}$ thiol-alkyl. In embodiments, $R^{14}$ is thiomethyl, thioethyl, thiopropyl, thiobutyl, thiopentyl, thiohexyl, thioheptyl, thiooctyl, thiononyl or thiodecyl. In embodiments, the compound has the structure (39)

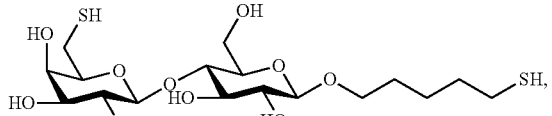

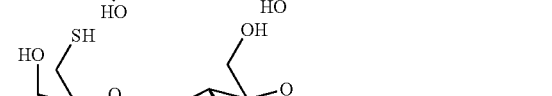

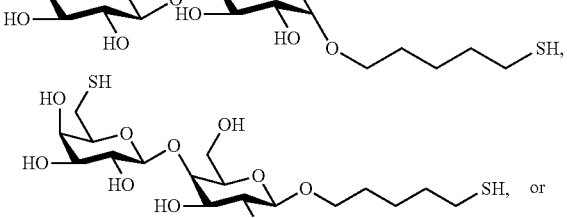

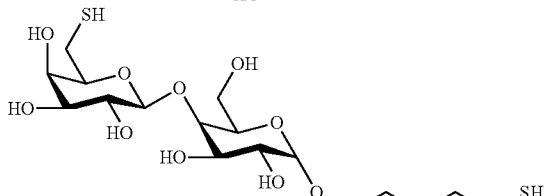

In embodiments of Formula (IIIa), $R^{14}$ is substituted or unsubstituted $C_1$-$C_{10}$ thiol-alkyl or substituted or unsubstituted 2 to 10 membered thiol-heteroalkyl. In embodiments, $R^{14}$ is unsubstituted $C_1$-$C_{10}$ thiol-alkyl, and $R^{10}$ is —OH. In embodiments, the compound has the structure following:

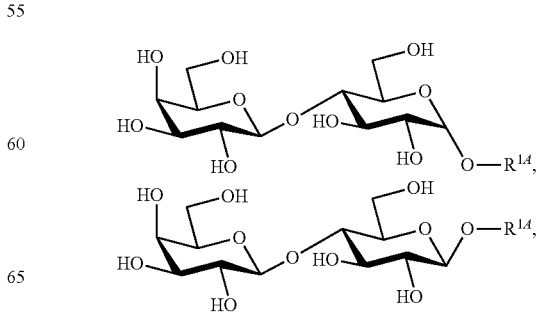

-continued

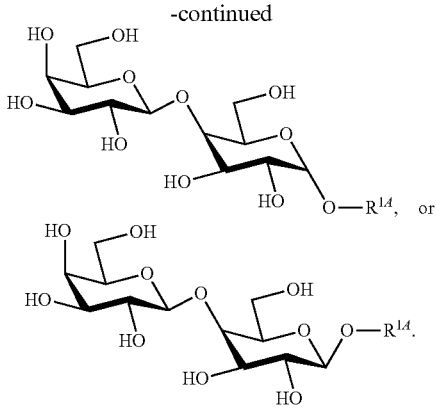

In embodiments, $R^{1A}$ is thiomethyl, thioethyl, thiopropyl, thiobutyl, thiopentyl, thiohexyl, thioheptyl, thiooctyl, thiononyl or thiodecyl. In embodiments, $R^{1A}$ is thioethyl. $R^{1A}$ is thiopentyl. In embodiments, $R^{1A}$ is H, and $R^{10}$ is —SH.

In embodiments of Formula (IIIa), $R^{1A}$ is substituted or unsubstituted $C_1$-$C_{10}$ thiol-alkyl, and $R^{10}$ is —OH. In embodiments, $R^{1A}$ is thiomethyl, thioethyl, thiopropyl, thiobutyl, thiopentyl, thiohexyl, thioheptyl, thiooctyl, thiononyl or thiodecyl. In embodiments, $R^{1A}$ is thiopentyl. In embodiments, the compound has the structure

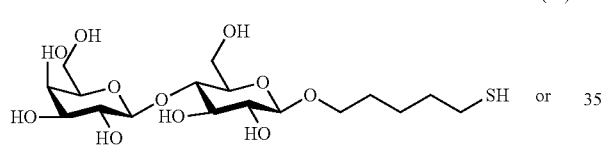
(40)

(41)

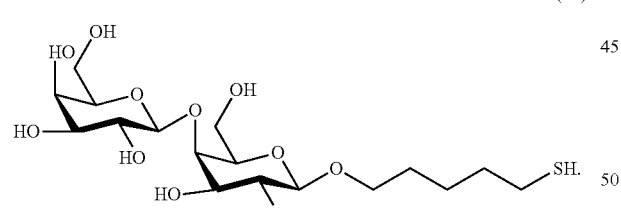

In embodiments, $R^{1A}$ is substituted or unsubstituted $C_1$-$C_{10}$ thiol-alkyl or substituted or unsubstituted 2 to 10 membered thiol-heteroalkyl, $R^2$, $R^3$, $R^5$, $R^7$, $R^8$, and $R^9$ are —OH, and $R^{10}$ is —SH. In embodiments, $R^{1A}$ is unsubstituted $C_1$-$C_{10}$ thiol-alkyl. In embodiments, $R^{1A}$ is thiomethyl, thioethyl, thiopropyl, thiobutyl, thiopentyl, thiohexyl, thioheptyl, thiooctyl, thiononyl or thiodecyl. In embodiments, $R^{1A}$ is thiopentyl.

In embodiments, $R^1$, $R^3$, $R^5$, $R^8$, $R^9$, and $R^{10}$ are —OH, $R^2$ is —OH or —NR$^{2B}$, $R^{2C}$ is substituted or unsubstituted $C_1$-$C_{10}$ thiol-alkyl, $R^7$ is —OH or —NR$^{7B}$, $R^{7C}$ is substituted or unsubstituted $C_1$-$C_{10}$ thiol-alkyl, and the thiosaccharide mucolytic agent has Formula (IIIb):

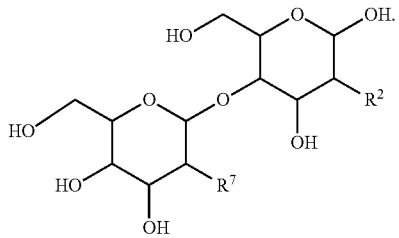
(IIIb)

In embodiments, the compound has the structure following:

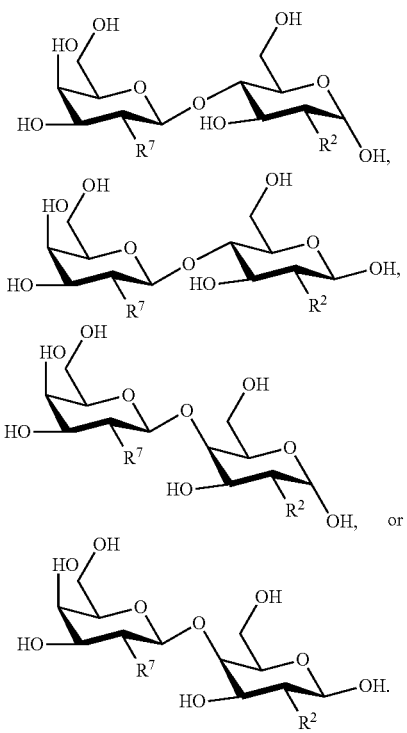

In embodiments, $R^1$ is —OR$^{1A}$, $R^{1A}$ is substituted or unsubstituted $C_1$-$C_{10}$ thiol-alkyl or substituted or unsubstituted 2 to 10 membered thiol-heteroalkyl, $R^3$, $R^5$, $R^8$, $R^9$, and $R^{10}$ are —OH, $R^2$ is —OH or —NR$^{2B}$, $R^{2C}$ is substituted or unsubstituted $C_1$-$C_{10}$ alkyl, $R^7$ is —OH or —NR$^{7B}$, $R^{7C}$ is substituted or unsubstituted $C_1$-$C_{10}$ alkyl, and the thiosaccharide mucolytic agent

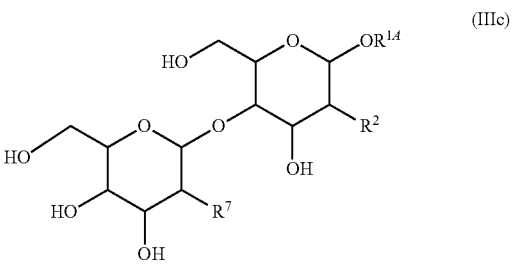
(IIIc)

In embodiments, the compound has the structure following:

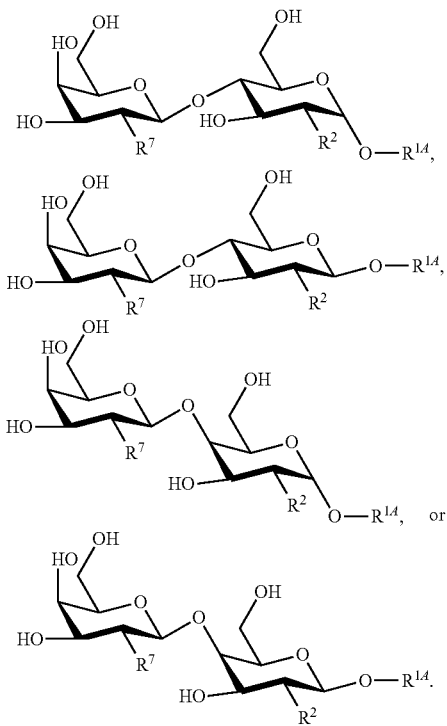

Further to Formula (IIc), in embodiments, $R^{1A}$ is substituted or unsubstituted $C_1$-$C_{10}$ thiol-alkyl. In embodiments, $R^{1A}$ is substituted or unsubstituted 2 to 10 membered thiol-heteroalkyl. In embodiments $R^2$ is —NHAc, and $R^7$ is —NHAc.

In embodiments, the thiosaccharide mucolytic agent has the formula:

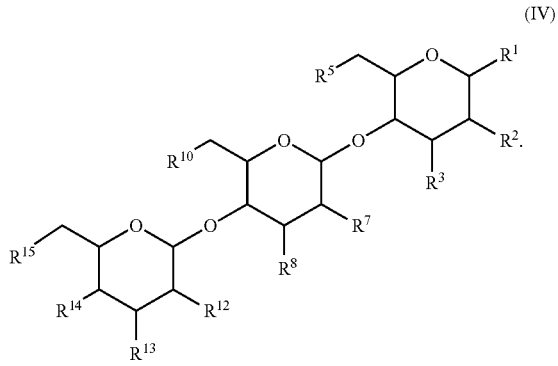

(IV)

In embodiments of Formula (IV), R is —$SR^{1A}$, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl, $R^{1B}$ is —$C(O)R^{1C}$, substituted or unsubstituted $C_1$-$C_{10}$ thiol-alkyl or substituted or unsubstituted 2 to 10 membered thiol-heteroalkyl, and $R^{1C}$ is substituted or unsubstituted $C_1$-$C_{10}$ thiol-alkyl or substituted or unsubstituted 2 to 10 membered thiol-heteroalkyl. $R^2$ is —$SR^{2A}$, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl, $R^{2B}$ is —$C(O)R^{2C}$, substituted or unsubstituted $C_1$-$C_{10}$ thiol-alkyl or substituted or unsubstituted 2 to 10 membered thiol-heteroalkyl, and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^3$ is —$SR^{3A}$, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl, $R^{3B}$ is —$C(O)R^{3C}$, substituted or unsubstituted $C_1$-$C_{10}$ thiol-alkyl or substituted or unsubstituted 2 to 10 membered thiol-heteroalkyl, and $R^{3C}$ is substituted or unsubstituted $C_1$-$C_{10}$ thiol-alkyl or substituted or unsubstituted 2 to 10 membered thiol-heteroalkyl. $R^5$ is H, —$SR^{5A}$, —SAc, —$OR^{5A}$ or —$NR^{5B}$, wherein $R^{5A}$ is H, substituted or unsubstituted $C_1$-$C_{10}$ thiol-alkyl or substituted or unsubstituted 2 to 10 membered thiol-heteroalkyl, $R^{5B}$ is —$C(O)R^{5C}$, substituted or unsubstituted $C_1$-$C_{10}$ thiol-alkyl or substituted or unsubstituted 2 to 10 membered thiol-heteroalkyl, and $R^{5C}$ is substituted or unsubstituted $C_1$-$C_{10}$ thiol-alkyl or substituted or unsubstituted 2 to 10 membered thiol-heteroalkyl. $R^7$ is —$SR^{7A}$, —$OR^{7A}$ or —$NR^{7B}$, wherein $R^{7A}$ is H, substituted or unsubstituted $C_1$-$C_{10}$ thiol-alkyl or substituted or unsubstituted 2 to 10 membered thiol-heteroalkyl, $R^{7B}$ is —$C(O)R^{7C}$, substituted or unsubstituted $C_1$-$C_{10}$ thiol-alkyl or substituted or unsubstituted 2 to 10 membered thiol-heteroalkyl, and $R^{7C}$ is substituted or unsubstituted $C_1$-$C_{10}$ thiol-alkyl or substituted or unsubstituted 2 to 10 membered thiol-heteroalkyl. $R^8$ is —$SR^{8A}$, —$OR^{8A}$ or —$NR^{8B}$, wherein $R^{8A}$ is H, substituted or unsubstituted $C_1$-$C_{10}$ thiol-alkyl or substituted or unsubstituted 2 to 10 membered thiol-heteroalkyl, $R^{8B}$ is —$C(O)R^{8C}$, substituted or unsubstituted $C_1$-$C_{10}$ thiol-alkyl or substituted or unsubstituted 2 to 10 membered thiol-heteroalkyl, and $R^{8C}$ is substituted or unsubstituted $C_1$-$C_{10}$ thiol-alkyl or substituted or unsubstituted 2 to 10 membered thiol-heteroalkyl. $R^{10}$ is H, —$SR^{10A}$, —SAc, —$OR^{10A}$ or —$NR^{10B}$, wherein $R^{10A}$ is H, substituted or unsubstituted $C_1$-$C_{10}$ thiol-alkyl or substituted or unsubstituted 2 to 10 membered thiol-heteroalkyl, $R^{10B}$ is —$C(O)R^{10C}$, substituted or unsubstituted $C_1$-$C_{10}$ thiol-alkyl or substituted or unsubstituted 2 to 10 membered thiol-heteroalkyl, $R^{10C}$ is substituted or unsubstituted $C_1$-$C_{10}$ thiol-alkyl or substituted or unsubstituted 2 to 10 membered thiol-heteroalkyl. $R^{12}$ is —$SR^{12A}$, —$OR^{12A}$ or —$NR^{2B}$, wherein $R^{12A}$ is H, substituted or unsubstituted $C_1$-$C_{10}$ thiol-alkyl or substituted or unsubstituted 2 to 10 membered thiol-heteroalkyl, $R^{2B}$ is —$C(O)R^{2C}$, substituted or unsubstituted $C_1$-$C_{10}$ thiol-alkyl or substituted or unsubstituted 2 to 10 membered thiol-heteroalkyl, and $R^{2C}$ is substituted or unsubstituted $C_1$-$C_{10}$ thiol-alkyl or substituted or unsubstituted 2 to 10 membered thiol-heteroalkyl. $R^{13}$—$SR^{13A}$, —$OR^{13A}$ or —$NR^{13B}$, wherein $R^{13A}$ is H, substituted or unsubstituted $C_1$-$C_{10}$ thiol-alkyl or substituted or unsubstituted 2 to 10 membered thiol-heteroalkyl, $R^{13B}$ is —$C(O)R^{3C}$, substituted or unsubstituted $C_1$-$C_{10}$ thiol-alkyl or substituted or unsubstituted 2 to 10 membered thiol-heteroalkyl, and $R^{13C}$ is substituted or unsubstituted $C_1$-$C_{10}$ thiol-alkyl or substituted or unsubstituted 2 to 10 membered thiol-heteroalkyl. $R^{14}$ is —$SR^{14A}$, —$OR^{14A}$ or —$NR^{14B}$, wherein $R^{14A}$ is H, substituted or unsubstituted $C_1$-$C_{10}$ thiol-alkyl or substituted or unsubstituted 2 to 10 membered thiol-heteroalkyl, $R^{14B}$ is —$C(O)R^{14C}$, substituted or unsubstituted $C_1$-$C_{10}$ thiol-alkyl or substituted or unsubstituted 2 to 10 membered thiol-heteroalkyl, and $R^{14C}$ is substituted or unsubstituted $C_1$-$C_{10}$ thiol-alkyl or substituted or unsubstituted 2 to 10 membered thiol-heteroalkyl. $R^{15}$ is H, —$SR^{15A}$, —SAc, —$OR^{15A}$ or —NR$^{15B}$, wherein R$^{15A}$ is H, substituted or unsubstituted C$_1$-C$_{10}$ thiol-alkyl or substituted or unsubstituted 2 to 10 membered thiol-heteroalkyl, R$^{15B}$ is —C(O)R$^{5C}$, substituted or unsubstituted C$_1$-C$_{10}$ thiol-alkyl or substituted or unsubstituted 2 to 10 membered thiol-heteroalkyl, and R$^{5C}$ is substituted or unsubstituted C$_1$-C$_{10}$ thiol-alkyl or substituted or unsubstituted 2 to 10 membered thiol-heteroalkyl.

In embodiments of Formula (IV), R$^1$ is —SR$^{1A}$, —OR$^{1A}$ or —NR$^{1B}$, wherein R$^{1A}$ is H, substituted or unsubstituted C$_1$-C$_{10}$alkyl, substituted or unsubstituted C$_1$-C$_{10}$ thiol-alkyl or substituted or unsubstituted 2 to 10 membered thiol-heteroalkyl, R$^{1B}$ is —C(O)R$^{1C}$, substituted or unsubstituted C$_1$-C$_{10}$ thiol-alkyl or substituted or unsubstituted 2 to 10 membered thiol-heteroalkyl, and R$^{1C}$ is substituted or unsubstituted C$_1$-C$_{10}$ thiol-alkyl or substituted or unsubstituted 2 to 10 membered thiol-heteroalkyl. R$^2$ is —SH, —OR$^{2A}$ or —NR$^{2B}$, wherein R$^{2A}$ is H, substituted or unsubstituted C$_1$-C$_{10}$ thiol-alkyl or substituted or unsubstituted 2 to 10 membered thiol-heteroalkyl, R$^{2B}$ is —C(O)R$^{2C}$, substituted or unsubstituted C$_1$-C$_{10}$ thiol-alkyl or substituted or unsubstituted 2 to 10 membered thiol-heteroalkyl, and R$^{2C}$ is substituted or unsubstituted C$_1$-C$_{10}$alkyl, substituted or unsubstituted C$_1$-C$_{10}$ thiol-alkyl or substituted or unsubstituted 2 to 10 membered thiol-heteroalkyl. R$^3$ is —SH, —OR$^{3A}$ or —NR$^{3B}$, wherein R$^{3A}$ is H, substituted or unsubstituted C$_1$-C$_{10}$ thiol-alkyl or substituted or unsubstituted 2 to 10 membered thiol-heteroalkyl, R$^{3B}$ is —C(O)R$^{3C}$, substituted or unsubstituted C$_1$-C$_{10}$ thiol-alkyl or substituted or unsubstituted 2 to 10 membered thiol-heteroalkyl, and R$^{3C}$ is substituted or unsubstituted C$_1$-C$_{10}$ thiol-alkyl or substituted or unsubstituted 2 to 10 membered thiol-heteroalkyl. R$^5$ is H, —SH, —SAc, —OR$^{5A}$ or —NR$^{5B}$, wherein R$^{5A}$ is H, substituted or unsubstituted C$_1$-C$_{10}$ thiol-alkyl or substituted or unsubstituted 2 to 10 membered thiol-heteroalkyl, R$^{5B}$ is —C(O)R$^{5C}$, substituted or unsubstituted C$_1$-C$_{10}$ thiol-alkyl or substituted or unsubstituted 2 to 10 membered thiol-heteroalkyl, and R$^{5C}$ is substituted or unsubstituted C$_1$-C$_{10}$ thiol-alkyl or substituted or unsubstituted 2 to 10 membered thiol-heteroalkyl. R$^7$ is —SH, —OR$^{7A}$ or —NR$^{7B}$, wherein R$^{7A}$ is H, substituted or unsubstituted C$_1$-C$_{10}$ thiol-alkyl or substituted or unsubstituted 2 to 10 membered thiol-heteroalkyl, R$^{7B}$ is —C(O)R$^{7C}$, substituted or unsubstituted C$_1$-C$_{10}$ thiol-alkyl or substituted or unsubstituted 2 to 10 membered thiol-heteroalkyl, and R$^{7C}$ is substituted or unsubstituted C$_1$-C$_{10}$ thiol-alkyl or substituted or unsubstituted 2 to 10 membered thiol-heteroalkyl. R$^8$ is —SH, —OR$^{8A}$ or —NR$^{8B}$, wherein R$^{8A}$ is H, substituted or unsubstituted C$_1$-C$_{10}$ thiol-alkyl or substituted or unsubstituted 2 to 10 membered thiol-heteroalkyl, R$^{8B}$ is —C(O)R$^{8C}$, substituted or unsubstituted C$_1$-C$_{10}$ thiol-alkyl or substituted or unsubstituted 2 to 10 membered thiol-heteroalkyl, and R$^{8C}$ is substituted or unsubstituted C$_1$-C$_{10}$ thiol-alkyl or substituted or unsubstituted 2 to 10 membered thiol-heteroalkyl. R$^{10}$ is H, —SH, —SAc, —OR$^{10A}$ or —NR$^{10B}$, wherein R$^{10A}$ is H, substituted or unsubstituted C$_1$-C$_{10}$ thiol-alkyl or substituted or unsubstituted 2 to 10 membered thiol-heteroalkyl, R$^{10B}$ is —C(O)R$^{10C}$, substituted or unsubstituted C$_1$-C$_{10}$ thiol-alkyl or substituted or unsubstituted 2 to 10 membered thiol-heteroalkyl, R$^{10C}$ is substituted or unsubstituted C$_1$-C$_{10}$ thiol-alkyl or substituted or unsubstituted 2 to 10 membered thiol-heteroalkyl. R$^{12}$—SH, —OR$^{12A}$ or —NR$^{12B}$, wherein R$^{12A}$ is H, substituted or unsubstituted C$_1$-C$_{10}$ thiol-alkyl or substituted or unsubstituted 2 to 10 membered thiol-heteroalkyl, R$^{12B}$ is —C(O)R$^{12C}$, substituted or unsubstituted C$_1$-C$_{10}$ thiol-alkyl or substituted or unsubstituted 2 to 10 membered thiol-heteroalkyl, and R$^{12C}$ is substituted or unsubstituted C$_1$-C$_{10}$ thiol-alkyl or substituted or unsubstituted 2 to 10 membered thiol-heteroalkyl. R$^{13}$—SH, —OR$^{13A}$ or —NR$^{13B}$, wherein R$^{13A}$ is H, substituted or unsubstituted C$_1$-C$_{10}$ thiol-alkyl or substituted or unsubstituted 2 to 10 membered thiol-heteroalkyl, R$^{3B}$ is —C(O)R$^{13C}$, substituted or unsubstituted C$_1$-C$_{10}$ thiol-alkyl or substituted or unsubstituted 2 to 10 membered thiol-heteroalkyl, and R$^{13C}$ is substituted or unsubstituted C$_1$-C$_{10}$ thiol-alkyl or substituted or unsubstituted 2 to 10 membered thiol-heteroalkyl. R$^{14}$ is —SH, —OR$^{14}$ or —NR$^{14B}$, wherein R$^{14A}$ is H, substituted or unsubstituted C$_1$-C$_{10}$ thiol-alkyl or substituted or unsubstituted 2 to 10 membered thiol-heteroalkyl, R$^{14B}$ is —C(O)R$^{14C}$, substituted or unsubstituted C$_1$-C$_{10}$ thiol-alkyl or substituted or unsubstituted 2 to 10 membered thiol-heteroalkyl, and R$^{14C}$ is substituted or unsubstituted C$_1$-C$_{10}$ thiol-alkyl or substituted or unsubstituted 2 to 10 membered thiol-heteroalkyl. R$^{15}$ is H, —SH, —SAc, —OR$^{15A}$ or —NR$^{15B}$, wherein R$^{15A}$ is H, substituted or unsubstituted C$_1$-C$_{10}$ thiol-alkyl or substituted or unsubstituted 2 to 10 membered thiol-heteroalkyl, R$^{15B}$ is —C(O)R$^{15C}$, substituted or unsubstituted C$_1$-C$_{10}$ thiol-alkyl or substituted or unsubstituted 2 to 10 membered thiol-heteroalkyl, and R$^{15C}$ is substituted or unsubstituted C$_1$-C$_{10}$ thiol-alkyl or substituted or unsubstituted 2 to 10 membered thiol-heteroalkyl.

In embodiments of Formula (IV), R$^1$ is —SH, —OR$^{1A}$ or —NR$^{1B}$, wherein R$^{1A}$ is H, substituted or unsubstituted C$_1$-C$_{10}$alkyl, substituted or unsubstituted C$_1$-C$_{10}$ thiol-alkyl or substituted or unsubstituted 2 to 10 membered thiol-heteroalkyl, R$^{1B}$ is —C(O)R$^{1C}$, substituted or unsubstituted C$_1$-C$_{10}$ thiol-alkyl or substituted or unsubstituted 2 to 10 membered thiol-heteroalkyl, and R$^{1C}$ is substituted or unsubstituted C$_1$-C$_{10}$ thiol-alkyl or substituted or unsubstituted 2 to 10 membered thiol-heteroalkyl. R$^2$ is —SH, —OR$^{2A}$ or —NR$^{2B}$, wherein R$^{2A}$ is H, substituted or unsubstituted C$_1$-C$_{10}$ thiol-alkyl or substituted or unsubstituted 2 to 10 membered thiol-heteroalkyl, R$^{2B}$ is —C(O)R$^{2C}$, substituted or unsubstituted C$_1$-C$_{10}$ thiol-alkyl or substituted or unsubstituted 2 to 10 membered thiol-heteroalkyl, and R$^{2C}$ is substituted or unsubstituted C$_1$-C$_{10}$alkyl, substituted or unsubstituted C$_1$-C$_{10}$ thiol-alkyl or substituted or unsubstituted 2 to 10 membered thiol-heteroalkyl. R$^3$ is —SH, —OR$^{3A}$ or —NR$^{3B}$, wherein R$^{3A}$ is H, substituted or unsubstituted C$_1$-C$_{10}$ thiol-alkyl or substituted or unsubstituted 2 to 10 membered thiol-heteroalkyl, R$^{3B}$ is —C(O)R$^{3C}$, substituted or unsubstituted C$_1$-C$_{10}$ thiol-alkyl or substituted or unsubstituted 2 to 10 membered thiol-heteroalkyl, and R$^{3C}$ is substituted or unsubstituted C$_1$-C$_{10}$ thiol-alkyl or substituted or unsubstituted 2 to 10 membered thiol-heteroalkyl. R$^5$ is H, —SH, —SAc, —OR$^{5A}$ or —NR$^{5B}$, wherein R$^{5A}$ is H, substituted or unsubstituted C$_1$-C$_{10}$ thiol-alkyl or substituted or unsubstituted 2 to 10 membered thiol-heteroalkyl, R$^{5B}$ is —C(O)R$^{5C}$, substituted or unsubstituted C$_1$-C$_{10}$ thiol-alkyl or substituted or unsubstituted 2 to 10 membered thiol-heteroalkyl, and R$^{5C}$ is substituted or unsubstituted C$_1$-C$_{10}$ thiol-alkyl or substituted or unsubstituted 2 to 10 membered thiol-heteroalkyl. R$^7$ is —SH, —OR$^{7A}$ or —NR$^{7B}$, wherein R$^{7A}$ is H, substituted or unsubstituted C$_1$-C$_{10}$ thiol-alkyl or substituted or unsubstituted 2 to 10 membered thiol-heteroalkyl, R$^{7B}$ is —C(O)R$^{7C}$, substituted or unsubstituted C$_1$-C$_{10}$ thiol-alkyl or substituted or unsubstituted 2 to 10 membered thiol-heteroalkyl, and R$^{7C}$ is substituted or unsubstituted C$_1$-C$_{10}$ thiol-alkyl or substituted or unsubstituted 2 to 10 membered thiol-heteroalkyl. R$^8$ is —SH, —OR$^{8A}$ or —NR$^{8B}$, wherein R$^{8A}$ is H, substituted or unsubstituted C$_1$-C$_{10}$ thiol-alkyl or substituted or unsubstituted 2 to 10 membered thiol-heteroalkyl, R$^{8B}$ is —C(O)R$^{8C}$, substituted or unsubstituted C$_1$-C$_{10}$ thiol-alkyl or substituted or unsubstituted 2 to 10 membered thiol-heteroalkyl, and $R^{8C}$ is substituted or unsubstituted $C_1$-$C_{10}$ thiol-alkyl or substituted or unsubstituted 2 to 10 membered thiol-heteroalkyl. $R^{10}$ is H, —SH, —SAc, —$OR^{10A}$ or —$NR^{10B}$, wherein $R^{10A}$ is H, substituted or unsubstituted $C_1$-$C_{10}$ thiol-alkyl or substituted or unsubstituted 2 to 10 membered thiol-heteroalkyl, $R^{10B}$ is —$C(O)R^{10C}$, substituted or unsubstituted $C_1$-$C_{10}$ thiol-alkyl or substituted or unsubstituted 2 to 10 membered thiol-heteroalkyl, $R^{10C}$ is substituted or unsubstituted $C_1$-$C_{10}$ thiol-alkyl or substituted or unsubstituted 2 to 10 membered thiol-heteroalkyl. $R^2$—SH, —$OR^{12A}$ or —$NR^{12B}$, wherein $R^{12A}$ is H, substituted or unsubstituted $C_1$-$C_{10}$ thiol-alkyl or substituted or unsubstituted 2 to 10 membered thiol-heteroalkyl, $R^{12B}$ is —$C(O)R^{12C}$, substituted or unsubstituted $C_1$-$C_{10}$ thiol-alkyl or substituted or unsubstituted 2 to 10 membered thiol-heteroalkyl, and $R^{12C}$ is substituted or unsubstituted $C_1$-$C_{10}$ thiol-alkyl or substituted or unsubstituted 2 to 10 membered thiol-heteroalkyl. $R^{13}$—SH, —$OR^{13A}$ or —$NR^{13B}$, wherein $R^{13A}$ is H, substituted or unsubstituted $C_1$-$C_{10}$ thiol-alkyl or substituted or unsubstituted 2 to 10 membered thiol-heteroalkyl, $R^{13B}$ is —$C(O)R^{13C}$, substituted or unsubstituted $C_1$-$C_{10}$ thiol-alkyl or substituted or unsubstituted 2 to 10 membered thiol-heteroalkyl, and $R^{13C}$ is substituted or unsubstituted $C_1$-$C_{10}$ thiol-alkyl or substituted or unsubstituted 2 to 10 membered thiol-heteroalkyl. $R^{14}$ is —SH, —$OR^{14A}$ or —$NR^{14B}$, wherein $R^{14A}$ is H, substituted or unsubstituted $C_1$-$C_{10}$ thiol-alkyl or substituted or unsubstituted 2 to 10 membered thiol-heteroalkyl, $R^{14B}$ is —$C(O)R^{14C}$, substituted or unsubstituted $C_1$-$C_{10}$ thiol-alkyl or substituted or unsubstituted 2 to 10 membered thiol-heteroalkyl, and $R^{14C}$ is substituted or unsubstituted $C_1$-$C_{10}$ thiol-alkyl or substituted or unsubstituted 2 to 10 membered thiol-heteroalkyl. $R^{15}$ is H, —SH, —SAc, —$OR^{15A}$ or —$NR^{15B}$, wherein $R^{15A}$ is H, substituted or unsubstituted $C_1$-$C_{10}$ thiol-alkyl or substituted or unsubstituted 2 to 10 membered thiol-heteroalkyl, $R^{15B}$ is —$C(O)R^{15C}$, substituted or unsubstituted $C_1$-$C_{10}$ thiol-alkyl or substituted or unsubstituted 2 to 10 membered thiol-heteroalkyl, and $R^{15C}$ is substituted or unsubstituted $C_1$-$C_{10}$ thiol-alkyl or substituted or unsubstituted 2 to 10 membered thiol-heteroalkyl.

Further to Formula (IV), in embodiments $R^1$, $R^3$, $R^5$, $R^8$, $R^{10}$, $R^{13}$, $R^{14}$ and $R^{15}$ are —OH, $R^2$ is —OH or —$NR^{2B}$, $R^{2B}$ is —$C(O)R^{2C}$, $R^{2C}$ is substituted or unsubstituted $C_1$-$C_{10}$ thiol-alkyl or substituted or unsubstituted 2 to 10 membered thiol-heteroalkyl, $R^7$ is —OH or —$NH^{7B}$, $R^{7B}$ is —$C(O)R^{7C}$, $R^{7C}$ is substituted or unsubstituted $C_1$-$C_{10}$ thiol-alkyl or substituted or unsubstituted 2 to 10 membered thiol-heteroalkyl, $R^{12}$ is —OH or —$NH^{12B}$, $R^{12B}$ is —$C(O)R^{12C}$, $R^{12C}$ is substituted or unsubstituted $C_1$-$C_{10}$ thiol-alkyl or substituted or unsubstituted 2 to 10 membered thiol-heteroalkyl, and the thiosaccharide mucolytic agent has Formula (IVa):

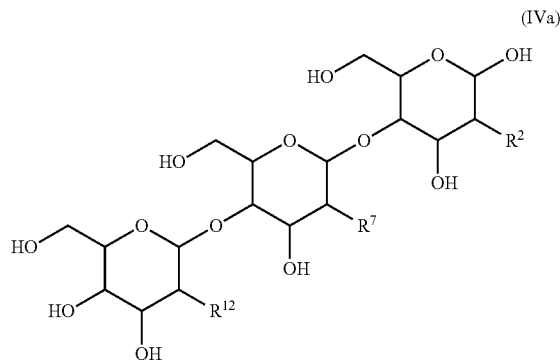

(IVa)

Further to Formula (IV), in embodiments $R^2$, $R^3$, $R^7$, $R^8$, $R^{12}$, $R^{13}$ and $R^{14}$ are —OH, $R^1$ is —SH or —$OR^{1A}$, $R^5$ is —SH or —$OR^{5A}$, $R^{10}$ is —SH or —$OR^{10A}$, and $R^{15}$ is —SH or —$OR^{15A}$, $R^{1A}$ is substituted or unsubstituted $C_1$-$C_{10}$alkyl, $R^{5A}$ is substituted or unsubstituted $C_1$-$C_{10}$ alkyl, $R^{10A}$ is substituted or unsubstituted $C_1$-$C_{10}$alkyl, and $R^{15A}$ is substituted or unsubstituted $C_1$-$C_{10}$alkyl:

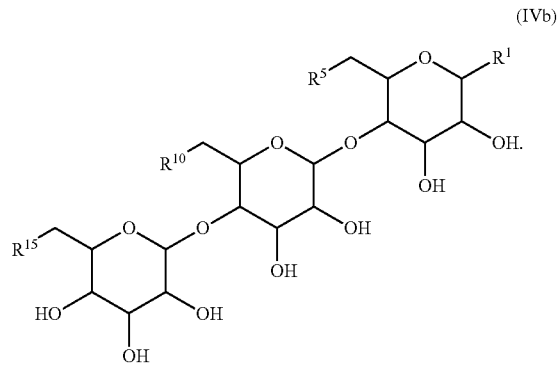

(IVb)

Regarding Formula (IVb), in embodiments one or more of $R^1$, $R^5$, $R^{10}$ and $R^{15}$ is —SH. In embodiments, $R^1$ is —SH. In embodiments, $R^5$ is —SH. In embodiments, $R^{10}$ is —SH. In embodiments, $R^{15}$ is —SH. In embodiments, $R^1$ and $R^5$ are —SH. In embodiments, $R^1$ and $R^{10}$ are —SH. In embodiments, $R^1$ and $R^{15}$ are —SH. In embodiments, $R^5$ and $R^{10}$ are —SH. In embodiments, $R^5$ and $R^{15}$ are —SH. In embodiments, $R^{10}$ and $R^{15}$ are —SH. In embodiments, $R^1$, $R^5$ and $R^{10}$ are —SH. In embodiments, $R^1$, $R^5$ and $R^{15}$ are —SH. In embodiments, $R^1$, $R^{10}$ and $R^{15}$ are —SH. In embodiments, $R^5$, $R^{10}$ and $R^{15}$ are —SH. In embodiments, $R^1$, $R^5$, $R^{10}$ and $R^{15}$ are —SH. In embodiments, $R^{1A}$ is unsubstituted $C_1$-$C_{10}$alkyl, $R^{5A}$ is unsubstituted $C_1$-$C_{10}$ alkyl, $R^{10A}$ is unsubstituted $C_1$-$C_{10}$alkyl, and $R^{15A}$ is unsubstituted $C_1$-$C_{10}$alkyl. In embodiments, $R^{1A}$ is methyl. In embodiments, $R^{5A}$ is methyl. In embodiments, $R^{10A}$ is methyl. In embodiments, $R^{15A}$ is methyl.

Further to Formula (IV), in embodiments $R^2$, $R^3$, $R^7$, $R^8$, $R^{12}$, $R^{13}$ and $R^{14}$ are —OH, $R^1$ is —$OR^{1A}$, wherein $R^{1A}$ is H, substituted or unsubstituted $C_1$-$C_{10}$alkyl, or substituted or unsubstituted $C_1$-$C_{10}$ thiol-alkyl, $R^5$ is —$OR^{5A}$, wherein $R^{5A}$ is H, substituted or unsubstituted $C_1$-$C_{10}$alkyl, or substituted or unsubstituted $C_1$-$C_{10}$ thiol-alkyl, $R^{10}$ is —$OR^{10A}$, wherein $R^{10A}$ is H, substituted or unsubstituted $C_1$-$C_{10}$alkyl, or substituted or unsubstituted $C_1$-$C_{10}$ thiol-alkyl, and $R^{15}$ is —$OR^{15A}$, wherein $R^{15A}$ is H, substituted or unsubstituted $C_1$-$C_{10}$alkyl, or substituted or unsubstituted $C_1$-$C_{10}$ thiol-alkyl. In embodiments, one or more of $R^{1A}$, $R^{5A}$, $R^{10A}$ and $R^{15A}$ are H or methyl. In embodiments, one or more of $R^{1A}$, $R^{5A}$, $R^{10A}$ and $R^{15A}$ are substituted or unsubstituted $C_1$-$C_{10}$alkyl. In embodiments, $R^{1A}$ is unsubstituted $C_1$-$C_{10}$ thiol-alkyl. In embodiments, $R^{5A}$ is unsubstituted $C_1$-$C_{10}$ thiol-alkyl. In embodiments, $R^{10A}$ is unsubstituted $C_1$-$C_{10}$ thiol-alkyl. In embodiments, $R^{15A}$ is unsubstituted $C_1$-$C_{10}$ thiol-alkyl. In embodiments, $R^{1A}$ is unsubstituted $C_5$ thiol-alkyl. In embodiments, $R^{5A}$ is unsubstituted $C_5$ thiol-alkyl. In embodiments, $R^{10A}$ is $C_5$ thiol-alkyl. In embodiments, $R^{15A}$ is unsubstituted $C_5$ thiol-alkyl. In embodiments, $R^{1A}$ is unsubstituted $C_1$-$C_6$ alkyl. In embodiments, $R^{5A}$ is unsubstituted $C_1$-$C_6$ alkyl. In embodiments, $R^{10A}$ is unsubstituted $C_1$-$C_6$ alkyl. In embodiments, $R^{15A}$ is unsubstituted $C_1$-$C_6$ alkyl. In embodiments, $R^{10A}$ is methyl. In embodiments, $R^{5A}$ is methyl. In embodiments, $R^{10A}$ is methyl. In embodiments, $R^{15A}$ is methyl.

In yet another embodiment of the method, the thiosaccharide mucolytic agent has the formula:

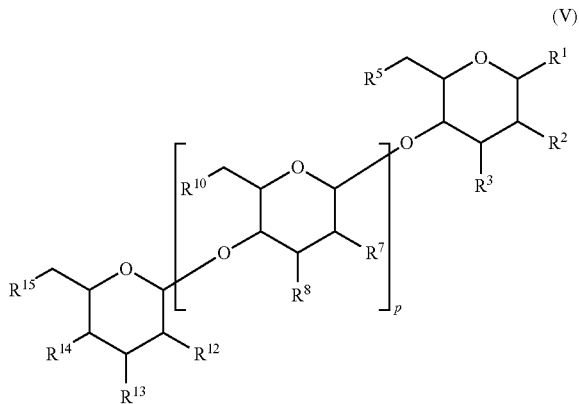

(V)

Regarding Formula (V), in embodiments $R^1$ is —$SR^{1A}$, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl, $R^{1B}$ is —$C(O)R^{1C}$, substituted or unsubstituted $C_1$-$C_{10}$ thiol-alkyl or substituted or unsubstituted 2 to 10 membered thiol-heteroalkyl, and $R^{1C}$ is substituted or unsubstituted $C_1$-$C_{10}$ thiol-alkyl or substituted or unsubstituted 2 to 10 membered thiol-heteroalkyl. $R^2$ is —$SR^{2A}$, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl, $R^{2B}$ is —$C(O)R^{2C}$, substituted or unsubstituted $C_1$-$C_{10}$ thiol-alkyl or substituted or unsubstituted 2 to 10 membered thiol-heteroalkyl, and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^3$ is —$SR^{3A}$, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl, $R^{3B}$ is —$C(O)R^{3C}$, substituted or unsubstituted $C_1$-$C_{10}$ thiol-alkyl or substituted or unsubstituted 2 to 10 membered thiol-heteroalkyl, and $R^{3C}$ is substituted or unsubstituted $C_1$-$C_{10}$ thiol-alkyl or substituted or unsubstituted 2 to 10 membered thiol-heteroalkyl. $R^5$ is H, —$SR^{5A}$, —SAc, —$OR^{5A}$ or —$NR^{5B}$, wherein $R^{5A}$ is H, substituted or unsubstituted $C_1$-$C_{10}$ thiol-alkyl or substituted or unsubstituted 2 to 10 membered thiol-heteroalkyl, $R^{5B}$ is —$C(O)R^{5C}$, substituted or unsubstituted $C_1$-$C_{10}$ thiol-alkyl or substituted or unsubstituted 2 to 10 membered thiol-heteroalkyl, $R^{5C}$ is substituted or unsubstituted $C_1$-$C_{10}$ thiol-alkyl or substituted or unsubstituted 2 to 10 membered thiol-heteroalkyl. $R^7$ at each occurrence is independently —$SR^{7A}$, —$OR^{7A}$ or —$NR^{7B}$, wherein $R^{7A}$ at each occurrence is independently H, substituted or unsubstituted $C_1$-$C_{10}$ thiol-alkyl or substituted or unsubstituted 2 to 10 membered thiol-heteroalkyl, $R^{7B}$ at each occurrence is independently —$C(O)R^{7C}$, substituted or unsubstituted $C_1$-$C_{10}$ thiol-alkyl or substituted or unsubstituted 2 to 10 membered thiol-heteroalkyl, and $R^{7C}$ at each occurrence is independently substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl. $R^8$ at each occurrence is independently —$SR^{8A}$, —$OR^{8A}$ or —$NR^{8B}$, wherein $R^{8A}$ at each occurrence is independently H, substituted or unsubstituted $C_1$-$C_{10}$ thiol-alkyl or substituted or unsubstituted 2 to 10 membered thiol-heteroalkyl, $R^{8B}$ at each occurrence is independently —$C(O)R^{8C}$, substituted or unsubstituted $C_1$-$C_{10}$ thiol-alkyl or substituted or unsubstituted 2 to 10 membered thiol-heteroalkyl, and $R^{8C}$ at each occurrence is independently substituted or unsubstituted $C_1$-$C_{10}$ thiol-alkyl or substituted or unsubstituted 2 to 10 membered thiol-heteroalkyl. $R^{10}$ at each occurrence is independently H, —$SR^{11A}$, —SAc, —$OR^{10A}$ or —$NR^{10B}$, wherein $R^{10A}$ at each occurrence is independently H, substituted or unsubstituted $C_1$-$C_{10}$ thiol-alkyl or substituted or unsubstituted 2 to 10 membered thiol-heteroalkyl, $R^{10B}$ at each occurrence is independently —$C(O)R^{10C}$, substituted or unsubstituted $C_1$-$C_{10}$ thiol-alkyl or substituted or unsubstituted 2 to 10 membered thiol-heteroalkyl, $R^{10C}$ at each occurrence is independently substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl. $R^{12}$ is —$SR^{12A}$, —$OR^{12A}$ or —$NR^{12B}$, wherein $R^{12A}$ is H, substituted or unsubstituted $C_1$-$C_{10}$ thiol-alkyl or substituted or unsubstituted 2 to 10 membered thiol-heteroalkyl, $R^{12B}$ is —$C(O)R^{12C}$, substituted or unsubstituted $C_1$-$C_{10}$ thiol-alkyl or substituted or unsubstituted 2 to 10 membered thiol-heteroalkyl, and $R^{12C}$ is substituted or unsubstituted $C_1$-$C_{10}$ thiol-alkyl or substituted or unsubstituted 2 to 10 membered thiol-heteroalkyl. $R^{13}$ is —$SR^{13A}$, —$OR^{13A}$ or —$NR^{13B}$, wherein $R^{13A}$ is H, substituted or unsubstituted $C_1$-$C_{10}$ thiol-alkyl or substituted or unsubstituted 2 to 10 membered thiol-heteroalkyl, $R^{3B}$ is —$C(O)R^{13C}$, substituted or unsubstituted $C_1$-$C_{10}$ thiol-alkyl or substituted or unsubstituted 2 to 10 membered thiol-heteroalkyl, and $R^{13C}$ is substituted or unsubstituted $C_1$-$C_{10}$ thiol-alkyl or substituted or unsubstituted 2 to 10 membered thiol-heteroalkyl. $R^{14}$ is —$SR^{14A}$, —$OR^{14A}$ or —$NR^{14B}$, wherein $R^{14A}$ is H, substituted or unsubstituted $C_1$-$C_{10}$ thiol-alkyl or substituted or unsubstituted 2 to 10 membered thiol-heteroalkyl, $R^{4B}$ is —$C(O)R^{14C}$, substituted or unsubstituted $C_1$-$C_{10}$ thiol-alkyl or substituted or unsubstituted 2 to 10 membered thiol-heteroalkyl, and $R^{14C}$ is substituted or unsubstituted $C_1$-$C_{10}$ thiol-alkyl or substituted or unsubstituted 2 to 10 membered thiol-heteroalkyl. $R^{15}$ is H, —$SR^{15A}$, —SAc, —$OR^{15A}$ or —$NR^{15B}$, wherein $R^{15A}$ is H, substituted or unsubstituted $C_1$-$C_{10}$ thiol-alkyl or substituted or unsubstituted 2 to 10 membered thiol-heteroalkyl, $R^{15B}$ is —$C(O)R^{1C}$, substituted or unsubstituted $C_1$-$C_{10}$ thiol-alkyl or substituted or unsubstituted 2 to 10 membered thiol-heteroalkyl, $R^{15C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. p is 2-10.

Regarding Formula (V), in embodiments $R^1$ is —$SR^{1A}$, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl, $R^{1B}$ is —$C(O)R^{1C}$, substituted or unsubstituted $C_1$-$C_{10}$ thiol-alkyl or substituted or unsubstituted 2 to 10 membered thiol-heteroalkyl, and $R^{1C}$ is substituted or unsubstituted $C_1$-$C_{10}$ thiol-alkyl or substituted or unsubstituted 2 to 10 membered thiol-heteroalkyl. $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl, $R^{2B}$ is —$C(O)R^{2C}$, substituted or unsubstituted $C_1$-$C_{10}$ thiol-alkyl or substituted or unsubstituted 2 to 10 membered thiol-heteroalkyl, and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl. $R^3$ is —SH, —OR$^{3A}$ or —NR$^{3B}$, wherein R$^{3A}$ is H, substituted or unsubstituted C$_1$-C$_{10}$ thiol-alkyl or substituted or unsubstituted 2 to 10 membered thiol-heteroalkyl, R$^{3B}$ is —C(O)R$^{3C}$, substituted or unsubstituted C$_1$-C$_{10}$ thiol-alkyl or substituted or unsubstituted 2 to 10 membered thiol-heteroalkyl, and R$^{3C}$ is substituted or unsubstituted C$_1$-C$_{10}$ thiol-alkyl or substituted or unsubstituted 2 to 10 membered thiol-heteroalkyl. R$^5$ is H, —SH, —SAc, —OR$^{5A}$ or —NR$^{5B}$ wherein R$^{5A}$ is H, substituted or unsubstituted C$_1$-C$_{10}$ thiol-alkyl or substituted or unsubstituted 2 to 10 membered thiol-heteroalkyl, R$^{5B}$ is —C(O)R$^{5C}$, substituted or unsubstituted C$_1$-C$_{10}$ thiol-alkyl or substituted or unsubstituted 2 to 10 membered thiol-heteroalkyl, R$^{5C}$ is substituted or unsubstituted C$_1$-C$_{10}$ thiol-alkyl or substituted or unsubstituted 2 to 10 membered thiol-heteroalkyl. R$^7$ at each occurrence is independently —SH, —OR$^{7A}$ or —NR$^{7B}$, wherein R$^{7A}$ at each occurrence is independently H, substituted or unsubstituted C$_1$-C$_{10}$ thiol-alkyl or substituted or unsubstituted 2 to 10 membered thiol-heteroalkyl, R$^{7B}$ at each occurrence is independently —C(O)R$^{7C}$, substituted or unsubstituted C$_1$-C$_{10}$ thiol-alkyl or substituted or unsubstituted 2 to 10 membered thiol-heteroalkyl, and R$^{7C}$ at each occurrence is independently substituted or unsubstituted C$_1$-C$_{10}$ alkyl, substituted or unsubstituted C$_1$-C$_{10}$ thiol-alkyl or substituted or unsubstituted 2 to 10 membered thiol-heteroalkyl. R$^8$ at each occurrence is independently —SH, —OR$^{8A}$ or —NR$^{8B}$, wherein R$^{8A}$ at each occurrence is independently H, substituted or unsubstituted C$_1$-C$_{10}$ thiol-alkyl or substituted or unsubstituted 2 to 10 membered thiol-heteroalkyl, R$^{8B}$ at each occurrence is independently —C(O)R$^{8C}$, substituted or unsubstituted C$_1$-C$_{10}$ thiol-alkyl or substituted or unsubstituted 2 to 10 membered thiol-heteroalkyl, and R$^{8C}$ at each occurrence is independently substituted or unsubstituted C$_1$-C$_{10}$ thiol-alkyl or substituted or unsubstituted 2 to 10 membered thiol-heteroalkyl. R$^{10}$ at each occurrence is independently H, —SH, —SAc, —OR$^{10A}$ or —NR$^{10B}$, wherein R$^{10A}$ at each occurrence is independently H, substituted or unsubstituted C$_1$-C$_{10}$ thiol-alkyl or substituted or unsubstituted 2 to 10 membered thiol-heteroalkyl, R$^{10B}$ at each occurrence is independently —C(O)R$^{10C}$, substituted or unsubstituted C$_1$-C$_{10}$ thiol-alkyl or substituted or unsubstituted 2 to 10 membered thiol-heteroalkyl, R$^{10C}$ at each occurrence is independently substituted or unsubstituted C$_1$-C$_{10}$alkyl, substituted or unsubstituted C$_1$-C$_{10}$ thiol-alkyl or substituted or unsubstituted 2 to 10 membered thiol-heteroalkyl. R$^{12}$ is —SH, —OR$^{12A}$ or —NR$^{12B}$, wherein R$^{12A}$ is H, substituted or unsubstituted C$_1$-C$_{10}$ thiol-alkyl or substituted or unsubstituted 2 to 10 membered thiol-heteroalkyl, R$^{2B}$ is —C(O)R$^{2C}$, substituted or unsubstituted C$_1$-C$_{10}$ thiol-alkyl or substituted or unsubstituted 2 to 10 membered thiol-heteroalkyl, and R$^{2C}$ is substituted or unsubstituted C$_1$-C$_{10}$ thiol-alkyl or substituted or unsubstituted 2 to 10 membered thiol-heteroalkyl. R$^{13}$ is —SH, —OR$^{13A}$ or —NR$^{13B}$, wherein R$^{13A}$ is H, substituted or unsubstituted C$_1$-C$_{10}$ thiol-alkyl or substituted or unsubstituted 2 to 10 membered thiol-heteroalkyl, R$^{13B}$ is —C(O)R$^{13C}$, substituted or unsubstituted C$_1$-C$_{10}$ thiol-alkyl or substituted or unsubstituted 2 to 10 membered thiol-heteroalkyl, and R$^{13C}$ is substituted or unsubstituted C$_1$-C$_{10}$ thiol-alkyl or substituted or unsubstituted 2 to 10 membered thiol-heteroalkyl. R$^{14}$ is —SH, —OR$^{14A}$ or —NR$^{14B}$, wherein R$^{14A}$ is H, substituted or unsubstituted C$_1$-C$_{10}$ thiol-alkyl or substituted or unsubstituted 2 to 10 membered thiol-heteroalkyl, R$^{14B}$ is —C(O)R$^{14C}$, substituted or unsubstituted C$_1$-C$_{10}$ thiol-alkyl or substituted or unsubstituted 2 to 10 membered thiol-heteroalkyl, and R$^{14C}$ is substituted or unsubstituted C$_1$-C$_{10}$ thiol-alkyl or substituted or unsubstituted 2 to 10 membered thiol-heteroalkyl. R$^{15}$ is H, —SH, —SAc, —OR$^{15A}$ or —NR$^{15B}$, wherein R$^{15A}$ is H, substituted or unsubstituted C$_1$-C$_{10}$ thiol-alkyl or substituted or unsubstituted 2 to 10 membered thiol-heteroalkyl, R$^{15B}$ is —C(O)R$^{15C}$, substituted or unsubstituted C$_1$-C$_{10}$ thiol-alkyl or substituted or unsubstituted 2 to 10 membered thiol-heteroalkyl, R$^{15C}$ is substituted or unsubstituted C$_1$-C$_{10}$alkyl, substituted or unsubstituted C$_1$-C$_{10}$ thiol-alkyl or substituted or unsubstituted 2 to 10 membered thiol-heteroalkyl. p is 2-10.

Regarding Formula (V), in embodiments R$^1$ is —SH, —OR$^{1A}$ or —NR$^{1B}$, wherein R$^{1A}$ is H, substituted or unsubstituted C$_1$-C$_{10}$alkyl, substituted or unsubstituted C$_1$-C$_{10}$ thiol-alkyl or substituted or unsubstituted 2 to 10 membered thiol-heteroalkyl, R$^{1B}$ is —C(O)R$^{1C}$, substituted or unsubstituted C$_1$-C$_{10}$ thiol-alkyl or substituted or unsubstituted 2 to 10 membered thiol-heteroalkyl, and R$^{1C}$ is substituted or unsubstituted C$_1$-C$_{10}$ thiol-alkyl or substituted or unsubstituted 2 to 10 membered thiol-heteroalkyl. R$^2$ is —SH, —OR$^{2A}$ or —NR$^{2B}$, wherein R$^{2A}$ is H, substituted or unsubstituted C$_1$-C$_{10}$ thiol-alkyl or substituted or unsubstituted 2 to 10 membered thiol-heteroalkyl, R$^{2B}$ is —C(O)R$^{2C}$, substituted or unsubstituted C$_1$-C$_{10}$ thiol-alkyl or substituted or unsubstituted 2 to 10 membered thiol-heteroalkyl, and R$^{2C}$ is substituted or unsubstituted C$_1$-C$_{10}$ alkyl, substituted or unsubstituted C$_1$-C$_{10}$ thiol-alkyl or substituted or unsubstituted 2 to 10 membered thiol-heteroalkyl. R$^3$ is —SH, —OR$^{3A}$ or —NR$^{3B}$, wherein R$^{3A}$ is H, substituted or unsubstituted C$_1$-C$_{10}$ thiol-alkyl or substituted or unsubstituted 2 to 10 membered thiol-heteroalkyl, R$^{3B}$ is —C(O)R$^{3C}$, substituted or unsubstituted C$_1$-C$_{10}$ thiol-alkyl or substituted or unsubstituted 2 to 10 membered thiol-heteroalkyl, and R$^{3C}$ is substituted or unsubstituted C$_1$-C$_{10}$ thiol-alkyl or substituted or unsubstituted 2 to 10 membered thiol-heteroalkyl. R$^5$ is H, —SH, —SAc, —OR$^{5A}$ or —NR$^{5B}$ wherein R$^{5A}$ is H, substituted or unsubstituted C$_1$-C$_{10}$ thiol-alkyl or substituted or unsubstituted 2 to 10 membered thiol-heteroalkyl, R$^{5B}$ is —C(O)R$^{5C}$, substituted or unsubstituted C$_1$-C$_{10}$ thiol-alkyl or substituted or unsubstituted 2 to 10 membered thiol-heteroalkyl, R$^{5C}$ is substituted or unsubstituted C$_1$-C$_{10}$ thiol-alkyl or substituted or unsubstituted 2 to 10 membered thiol-heteroalkyl. R$^7$ at each occurrence is independently —SH, —OR$^{7A}$ or —NR$^{7B}$, wherein R$^{7A}$ at each occurrence is independently H, substituted or unsubstituted C$_1$-C$_{10}$ thiol-alkyl or substituted or unsubstituted 2 to 10 membered thiol-heteroalkyl, R$^{7B}$ at each occurrence is independently —C(O)R$^{7C}$, substituted or unsubstituted C$_1$-C$_{10}$ thiol-alkyl or substituted or unsubstituted 2 to 10 membered thiol-heteroalkyl, and R$^{7C}$ at each occurrence is independently substituted or unsubstituted C$_1$-C$_{10}$ alkyl, substituted or unsubstituted C$_1$-C$_{10}$ thiol-alkyl or substituted or unsubstituted 2 to 10 membered thiol-heteroalkyl. R$^8$ at each occurrence is independently —SH, —OR$^{8A}$ or —NR$^{8B}$, wherein R$^{8A}$ at each occurrence is independently H, substituted or unsubstituted C$_1$-C$_{10}$ thiol-alkyl or substituted or unsubstituted 2 to 10 membered thiol-heteroalkyl, R$^{8B}$ at each occurrence is independently —C(O)R$^{8C}$, substituted or unsubstituted C$_1$-C$_{10}$ thiol-alkyl or substituted or unsubstituted 2 to 10 membered thiol-heteroalkyl, and R$^{8C}$ at each occurrence is independently substituted or unsubstituted C$_1$-C$_{10}$ thiol-alkyl or substituted or unsubstituted 2 to 10 membered thiol-heteroalkyl. R$^{10}$ at each occurrence is independently H, —SH, —SAc, —OR$^{10A}$ or —NR$^{10B}$, wherein R$^{10A}$ at each occurrence is independently H, substituted or unsubstituted C$_1$-C$_{10}$ thiol-alkyl or substituted or unsubstituted 2 to 10 membered thiol-heteroalkyl, R$^{10B}$ at each occurrence is independently —C(O)R$^{10C}$, substituted or unsubstituted $C_1$-$C_{10}$ thiol-alkyl or substituted or unsubstituted 2 to 10 membered thiol-heteroalkyl, $R^{10C}$ at each occurrence is independently substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl. $R^{12}$ is —SH, —$OR^{12A}$ or —$NR^{12B}$, wherein $R^{12A}$ is H, substituted or unsubstituted $C_1$-$C_{10}$ thiol-alkyl or substituted or unsubstituted 2 to 10 membered thiol-heteroalkyl, $R^{12B}$ is —$C(O)R^{12C}$, substituted or unsubstituted $C_1$-$C_{10}$ thiol-alkyl or substituted or unsubstituted 2 to 10 membered thiol-heteroalkyl, and $R^{12C}$ is substituted or unsubstituted $C_1$-$C_{10}$ thiol-alkyl or substituted or unsubstituted 2 to 10 membered thiol-heteroalkyl. $R^{13}$ is —SH, —$OR^{13A}$ or —$NR^{13B}$, wherein $R^{13A}$ is H, substituted or unsubstituted $C_1$-$C_{10}$ thiol-alkyl or substituted or unsubstituted 2 to 10 membered thiol-heteroalkyl, $R^{13B}$ is —$C(O)R^{13C}$, substituted or unsubstituted $C_1$-$C_{10}$ thiol-alkyl or substituted or unsubstituted 2 to 10 membered thiol-heteroalkyl, and $R^{13C}$ is substituted or unsubstituted $C_1$-$C_{10}$ thiol-alkyl or substituted or unsubstituted 2 to 10 membered thiol-heteroalkyl. $R^{14}$ is —SH, —$OR^{14A}$ or —$NR^{14B}$, wherein $R^{14A}$ is H, substituted or unsubstituted $C_1$-$C_{10}$ thiol-alkyl or substituted or unsubstituted 2 to 10 membered thiol-heteroalkyl, $R^{14B}$ is —$C(O)R^{14C}$, substituted or unsubstituted $C_1$-$C_{10}$ thiol-alkyl or substituted or unsubstituted 2 to 10 membered thiol-heteroalkyl, and $R^{14C}$ is substituted or unsubstituted $C_1$-$C_{10}$ thiol-alkyl or substituted or unsubstituted 2 to 10 membered thiol-heteroalkyl. $R^{15}$ is H, —SH, —SAc, —$OR^{15A}$ or —$NR^{15B}$, wherein $R^{15A}$ is H, substituted or unsubstituted $C_1$-$C_{10}$ thiol-alkyl or substituted or unsubstituted 2 to 10 membered thiol-heteroalkyl, $R^{15B}$ is —$C(O)R^{15C}$, substituted or unsubstituted $C_1$-$C_{10}$ thiol-alkyl or substituted or unsubstituted 2 to 10 membered thiol-heteroalkyl, $R^{15C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl. p is 2-10.

III. Compounds

In another aspect, there is provided a compound with structure of Formula (I), wherein substituents $R^1$, $R^2$, $R^3$, $R^4$, $R^5$, $R^{5'}$, $R^{1A}$, $R^{1B}$, $R^{1C}$, RD, $R^{2A}$, $R^{2B}$, $R^{2C}$, $R^{3A}$, $R^{3B}$, $R^{4A}$, $R^{4B}$, $R^{5A}$, $R^{5B}$, $R^{5C}$, and $R^{5D}$ are as disclosed herein for Formula (I),

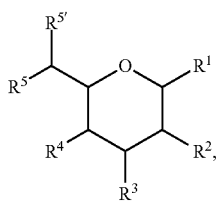

(I)

provided, however, that the compound does not have the structure following:

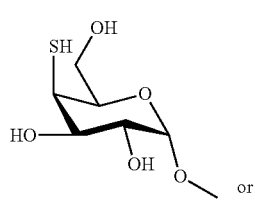

(29)

or

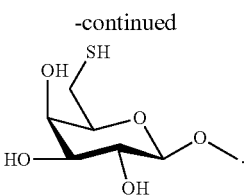

In embodiments, the compound has the structure of any one of Formulae (I), (Ia)-(Ii), (II), (III), (IIIa), (IIIb), (IIIc), (IV), (IVa), (V), (VI), (VIa), (VIb) or (VII), or embodiments thereof, disclosed herein.

In embodiments of Formula (I), the compound has the structure of Formula (Ie'):

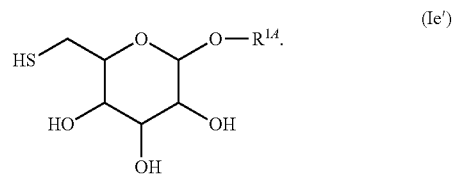

(Ie')

In embodiments of Formula (Ie'), the compound has the structure following:

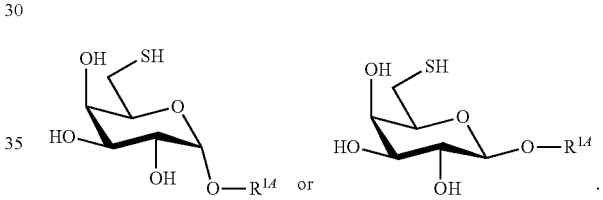

In embodiments of Formula (Ie'), $R^{14}$ is unsubstituted $C_1$-$C_{10}$ alkyl. In embodiments, $R^{14}$ is methyl. In embodiments, the compound has the structure following:

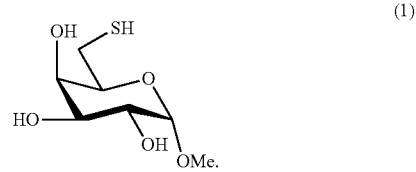

(1)

In embodiments of Formula (I), the compound has the structure of Formula (Ib'):

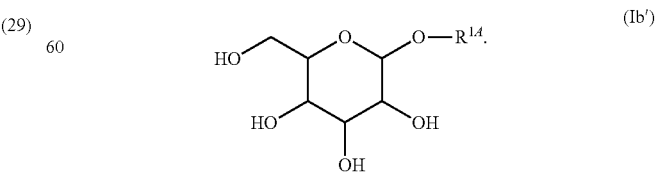

(Ib')

In embodiments, the compound of Formula (Ib') has the structure following:
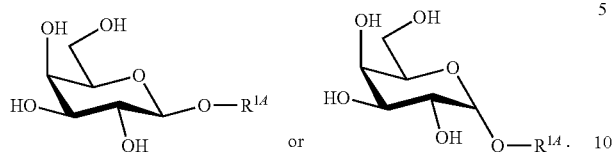
In embodiments of Formula (Ib'), the compound has the structure following:
(2)
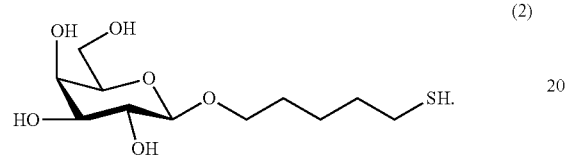
In embodiments of Formula (I), the compound has the structure of
(26)
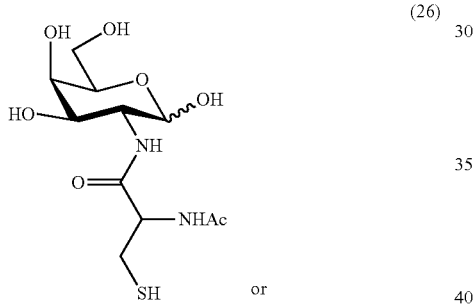
or
(27)
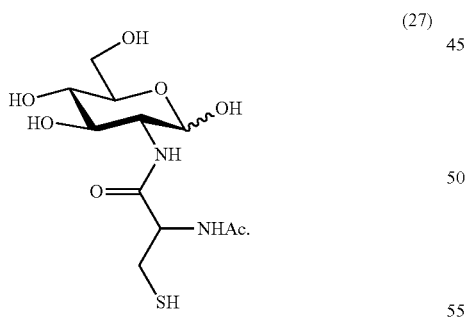
In embodiments, the compound has the structure of
(1)
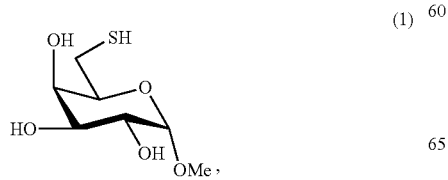
-continued
(28)
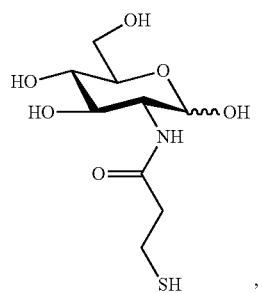
(6)
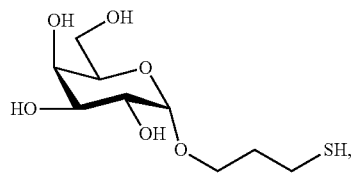
(33)
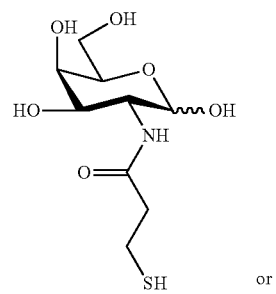
or
(34)
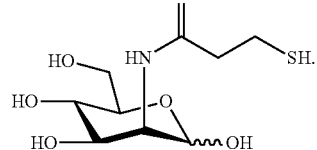
In embodiments, the compound has the structure of
(30)
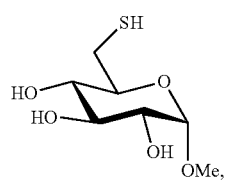
(31)
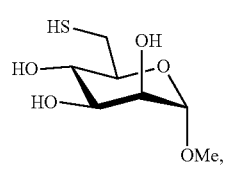
(32)
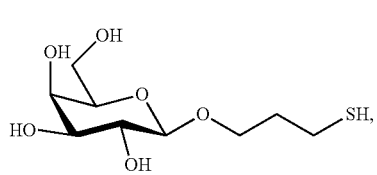

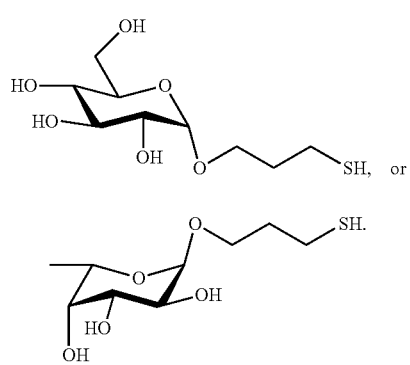

(10)

(11)

In embodiments, the compound has the structure of

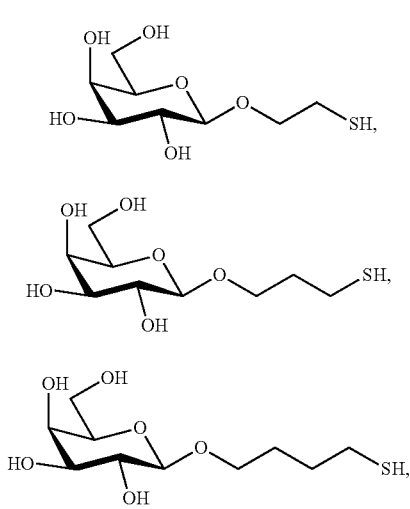

(3)

(13)

(14)

(2)

(16)

In embodiments, the compound has the structure of

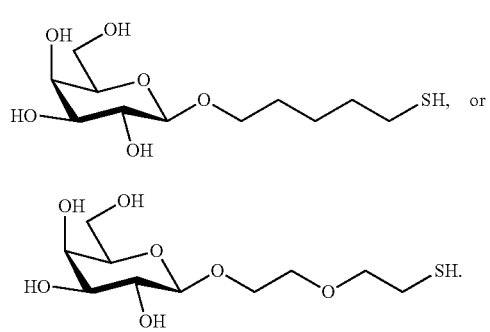

(4)

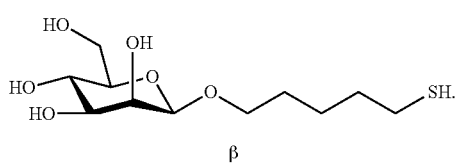

(5)

In embodiments, the compound has the structure of

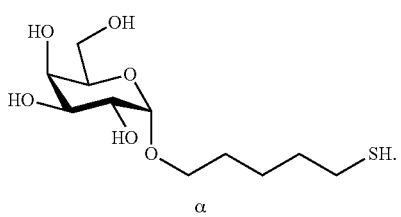

(7)

In embodiments, the compound has the structure of

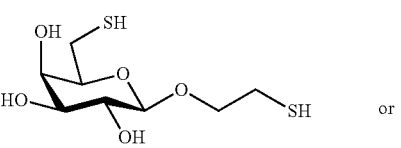

(21)

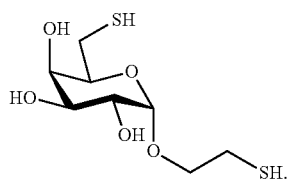

(22)

In embodiments, the compound has the structure of

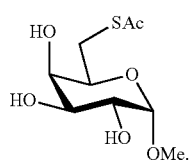

(25)

In another aspect, there is provided a compound with structure of Formula (VI), wherein substituents $R^1$, $R^2$, $R^3$, and $R^4$ are as described herein for Formula (I),

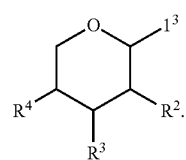

(VI)

In embodiments, the compound has the structure of (35)

(36)

In embodiments, the compound has the structure of

In another aspect, there is provided a compound with structure of Formula (II), wherein substituents $R^1$, $R^2$, $R^3$, $R^4$, $R^5$, $L^1$ and $L^2$ are as described herein for Formula (II):

(II)

In another aspect, there is provided a compound with structure of Formula (III), wherein substituents $R^1$, $R^2$, $R^3$, $R^5$, $R^7$, $R^8$, $R^9$ and $R^{10}$, $R^{1A}$, $R^{1B}$, $R^{1C}$, $R^{1D}$, $R^{2A}$, $R^{2B}$, $R^{2C}$, $R^{3A}$, $R^{3B}$, $R^{4A}$, $R^{4B}$, $R^{5A}$, $R^{5B}$, $R^{5C}$, $R^{5D}$, $R^{7A}$, $R^{7B}$, $R^{8A}$, $R^{8B}$, $R^{9A}$, $R^{9B}$, $R^{10A}$, $R^{10B}$ and $R^{10C}$ are as described herein for Formula (III):

(III)

In embodiments, the compound with structure of Formula (III), has the structure of (17)

(18)

(19)

(20)

In embodiments, the compound has the structure of (23)

(24)

In another aspect, there is provided a thiosaccharide mucolytic agent having the structure of Formula (VII) following, wherein $R^1$, $R^2$, $R^3$, $R^4$, $R^{1A}$, $R^{1B}$, $R^{1C}$, $R^{1D}$, $R^{2A}$, $R^{2B}$, $R^{2C}$, $R^{3A}$, $R^{3B}$, $R^{4A}$, and $R^{4B}$ are as defined for Formula (I).

(VII)

In embodiments of Formula (VII), the compound has the structure of

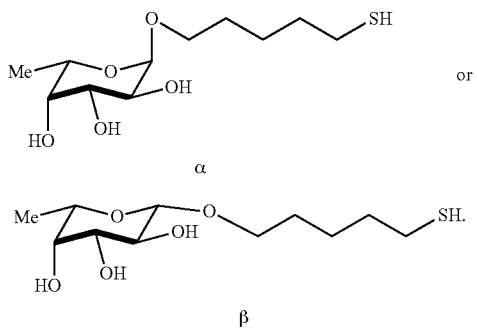

In another aspect, there is provided a compound with structure of Formula (IV), wherein $R^1$, $R^2$, $R^3$, $R^5$, $R^7$, $R^8$, $R^{10}$, $R^{12}$, $R^3$, $R^{14}$ and $R^{15}$ are as described herein for Formula (IV), and embodiments thereof:

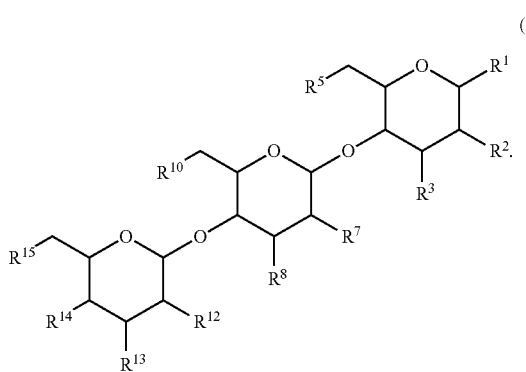

In another aspect, there is provided a compound with structure of Formula (V), wherein $R^1$, $R^2$, $R^3$, $R^5$, $R^7$, $R^8$, $R^{10}$, $R^{12}$, $R^{13}$, $R^4$, $R^{15}$ and p are as described herein for Formula (V), and embodiments thereof:

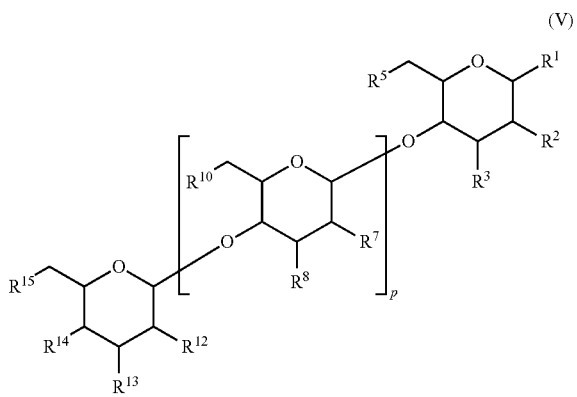

IV. Pharmaceutical Compositions

In another aspect, there is provided a pharmaceutical composition including a pharmaceutically acceptable excipient and a compound, or pharmaceutically acceptable salt thereof, as described herein (e.g., a compound of any one of Formulae (I), (Ia)-(Ii), (II), (III), (IIIa), (IIIb), (IIIc), (IV), (IVa), (V), (VI), (VIa), (VIb) or (VII), or embodiments thereof.

The terms "pharmaceutical composition" and the like refer, in the usual and customary sense, to a composition which is generally recognized as safe and effective for administration to a subject. The terms "pharmaceutically acceptable excipient," "pharmaceutically acceptable carrier" and the like refer, the usual and customary sense, to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (e.g., Ringer's solution and the like), alcohols, oils, gelatins, and carbohydrates such as lactose, amylose or starch, fatty acid esters, hydroxymethylcellulose, polyvinyl pyrrolidine, mannitol, and the parent sugar of a thiosaccharide mucolytic agent as disclosed herein, wherein the thiosaccharide mucolytic agent lacks a thiol functionality, e.g., D-glucopyranose, D-galactopyranose, D-mannopyranose, D-glucopyranoside, D-galactopyranoside, or D-mannopyranoside. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. The compounds described herein can be administered alone or can be coadministered to a subject. Coadministration is meant to include simultaneous or sequential administration of the compounds individually or in combination (more than one compound). The preparations can also be combined, when desired, with other active substances (e.g., to reduce metabolic degradation).

A. Formulations

The compounds disclosed herein can be prepared and administered in a wide variety of inhalation, oral, parenteral, and topical dosage forms, preferably inhalation. Thus, the compounds of the present invention can be administered by injection (e.g., intravenously, intramuscularly, intracutaneously, subcutaneously, intraduodenally, or intraperitoneally). Also, the compounds described herein can be administered by inhalation and by the intranasal route. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable carrier or excipient and one or more compounds of the invention.

For preparing pharmaceutical compositions from the compounds described herein, pharmaceutically acceptable carriers can be either solid or liquid. Solid form preparations include powders, tablets, pills, capsules, cachets, suppositories, and dispersible granules. A solid carrier can be one or more substance that may also act as diluents, flavoring agents, binders, preservatives, tablet disintegrating agents, or an encapsulating material.

In powders, the carrier is a finely divided solid in a mixture with the finely divided active component. In tablets, the active component is mixed with the carrier having the necessary binding properties in suitable proportions and compacted in the shape and size desired.

The powders and tablets preferably contain from 5% to 100% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampoules are convenient unit dosages. The compounds of the invention can also be incorporated into liposomes or administered via transdermal pumps or patches. Pharmaceutical admixtures suitable for use in the present invention include those described, for example, in PHARMACEUTICAL SCIENCES (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 0.1 mg to 10000 mg, more typically 1.0 mg to 1000 mg, most typically 10 mg to 500 mg, according to the particular application and the potency of the active component. The composition can, if desired, also contain other compatible therapeutic agents.

Some compounds may have limited solubility in water and therefore may require a surfactant or other appropriate co-solvent in the composition. Such co-solvents include: Polysorbate 20, 60, and 80; Pluronic F-68, F-84, and P-103; cyclodextrin; and polyoxyl 35 castor oil. Such co-solvents are typically employed at a level between about 0.01% and about 2% by weight.

Viscosity greater than that of simple aqueous solutions may be desirable to decrease variability in dispensing the formulations, to decrease physical separation of components of a suspension or emulsion of formulation, and/or otherwise to improve the formulation. Such viscosity building agents include, for example, polyvinyl alcohol, polyvinyl pyrrolidone, methyl cellulose, hydroxy propyl methylcellulose, hydroxyethyl cellulose, carboxymethyl cellulose, hydroxy propyl cellulose, chondroitin sulfate and salts thereof, hyaluronic acid and salts thereof, and combinations of the foregoing. Such agents are typically employed at a level between about 0.01% and about 2% by weight.

The compositions of the present invention may additionally include components to provide sustained release and/or comfort. Such components include high molecular weight, anionic mucomimetic polymers, gelling polysaccharides, and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

In another aspect, there is provided a pulmonary pharmaceutical composition comprising a pulmonary pharmaceutical carrier and a thiosaccharide mucolytic agent. The terms "pulmonary pharmaceutical composition" and the like refer to pharmaceutical compositions intended for pulmonary administration. The terms "pulmonary administration" and the like refer, in the usual and customary sense, to administration to achieve inhalation therapy. The term "inhalation therapy" and the like refer to direct delivery of medications to the lungs by inhalation. The thiosaccharide mucolytic agent disclosed herein are effective as mucolytics when delivered directly to the lung by an inhaled drug delivery system so that the intra-luminal mucus can be directly contacted by the drug to "lyse" or break up the mucus (mucolytic activity). The term "pulmonary pharmaceutical liquid" refers to a pulmonary pharmaceutical composition which is a liquid. The terms "pulmonary pharmaceutical solid," "pulmonary pharmaceutical solid" and the like refer to a pulmonary pharmaceutical composition which is a solid (e.g., a powder).

There are three categories of inhaled drug delivery systems: (i) nebulizers; (ii) pressurized metered-dose inhalers (pMDIs); (iii) dry powder inhalers (DPIs). Nebulizers are distinctly different from both pMDIs and DPIs, in that the active agent is dissolved or suspended in a polar liquid, e.g., water. In contrast, pMDIs and DPIs are bolus drug delivery devices that contain active agent (e.g., solid thiosaccharide mucolytic agent), suspended or dissolved in a nonpolar volatile propellant or in a dry powder mix that is fluidized when the patient inhales. pMDIs and DPIs have considerably reduced treatment time compared with nebulizers. The term "pulmonary pharmaceutical delivery device" and the like refer to an inhaled drug delivery system suitable for delivery (e.g., pulmonary delivery) of a pulmonary pharmaceutical composition.

Without wishing to be bound by any theory, it is believed that the lung deposition characteristics and efficacy of an aerosol depend largely on the particle or droplet size. For example, particles of more than 10 µm in diameter are most likely to deposit in the mouth and throat, for those of 5-10 µm diameter a transition from mouth to airway deposition occurs, and particles smaller than 5 μm in diameter deposit more frequently in the lower airways and are appropriate for pharmaceutical aerosols (e.g., pulmonary pharmaceutical compositions). Aerodynamic particle size distribution is measured by methods known in the art, e.g., cascade impaction method. Micronization is a conventional approach for size reduction. Additional drug particle engineering technologies includes spray drying large porous particles, sonocrystalization, or super critical fluids, and the like as known in the art. In embodiments, the particle is a nanoparticle, as known in the art. In all of these technologies, the particles can be delivered alone or co-formulated with carriers.

It is further believed that ideal inhaled particles are characterized as having uniform particle size with monodispersion, uniform density, non-cohesiveness, no agglomeration, no compaction, excellent flowability, and ready dispersal when delivered as an aerosol.

It is further believed that the attributes of an optimized inhaled delivery system include stability (i.e., consistent delivered dose through inhaler life), consistent aerodynamic particle size distribution (i.e., fine particle dose/fraction), and chemical and performance stability, as known in the art.

It is further believed that key formulation considerations for the pulmonary pharmaceutical composition disclosed herein include consistent product performance on stability and through the labeled number of doses, uniform formulation upon shaking to ensure metering and delivery of accurate and consistent doses, drug suspension stabilized by forming loose agglomerates and readily re-dispersed upon shaking after storage, no particle growth due to aggregation or crystal growth to ensure aerosolization performance, no drug loss due to deposition on dispenser to ensure consistent doses through inhaler life, and protection from moisture ingression to ensure long term stability.

Regarding nebulizers, as known in the art, nebulizers can employ a carrier (e.g., oxygen, inert gas, compressed air and the like) or a mechanical means (e.g., jet nebulization, ultrasonic power and the like) to break up pharmaceutical compositions (e.g., solutions and suspensions) into small aerosol droplets that can be directly inhaled from the nebulizer. The term "aerosol" and the like refer, in the usual and customary sense to a mixture of gas and liquid particles. The term "jet nebulizer" and the like refer, in the usual and customary sense, to any of a variety of devices connected by tubing to a compressor that causes compressed air or oxygen to flow at high velocity through a liquid medicine to turn it into an aerosol, which is then inhaled by the patient. Jet nebulizers are commonly used for patients in hospitals who have difficulty using inhalers or who require higher doses of drug than can be delivered with hand held devices such as pMDIs or DPIs. The term "ultrasonic nebulizer" and the like refer, in the usual and customary sense, to nebulizers having an electronic oscillator to generate a high frequency ultrasonic wave, which causes the mechanical vibration of a piezoelectric element. This vibrating element is in contact with a liquid reservoir and its high frequency vibration is sufficient to produce a vapor mist. These nebulizers are used commonly when aerosol drugs need to be administered while patients are on a mechanical ventilator.

A DPI is a device that delivers medication to the lungs in the form of a dry powder. When a DPI is actuated, the formulation is fluidized and enters the patient's airways. Under the influence of inspiratory airflow, the drug particles separate from the carrier particles and are carried deep into the lungs, while the larger carrier particles impact on the oropharyngeal surfaces and are cleared. If the cohesive forces acting on the powder are too strong, the shear of the airflow may not be sufficient to separate the drug from the carrier particles, which results in low deposition efficiency. Advances in understanding of aerosol and solid state physics and interfacial chemistry are moving formulation development from an empirical activity to a fundamental scientific foundation. Once loaded or actuated, the operator puts the mouthpiece of the inhaler into their mouth and takes a deep inhalation, holding their breath for a time (e.g., 5-10 seconds). The dose that can be delivered is typically less than a few tenths of milligrams in a single breath.

As known in the art, the formulation of an agent (e.g., a thiosaccharide mucolytic agent) in DPIs often includes a micronized agent blended with larger carrier particles to enhance flow, reduce aggregation, and aid in dispersion. Key variables in the formulation include intrinsic physicochemical properties, particle size, shape, surface area, and morphology, all of which affects forces of interaction and aerodynamic properties, which in turn determine fluidization, dispersion, delivery to the lungs, and deposition in the peripheral airways. DPIs are typically formulated as one-phase, solid particle blends, which has stability and processing advantages. DPIs involve micronized powder often packaged in single dose quantities in blisters or gel capsules containing the powdered medication to be drawn into the lungs by the user's own breath. Many DPI formulations consist of micronized agent blended with larger carrier particles, which enhance flow, reduce aggregation, and aid in dispersion. A combination of intrinsic physicochemical properties, particle size, shape, surface area, and morphology affects the forces of interaction and aerodynamic properties, which in turn determine fluidization, dispersion, delivery to the lungs, and deposition in the peripheral airways. Some DPIs use a bulking agent to aid in powder uptake from the device during inhalation.

Without wishing to be bound by any theory, it is believed that a DPI formulation must undergo flow, fluidization, and de-aggregation. However, micronized particles, particularly those resulting from high-energy operations such as jet milling, have high surface areas and surface energies, which can result in poor flow and a high tendency to aggregate. One way to improve the non-pharmacologic properties of a drug is through the addition of excipients to enhance the physical or chemical stability of the active pharmaceutical ingredient mechanical properties, and/or its pharmaceutical properties, such as dissolution and permeation. In DPI formulations, excipients function first and foremost as carrier particles. Usually, no more than a few milligrams of agent need to be delivered, and excipients provide bulk, which improves handling, dispensing, and metering of the drug. Excipients also reduce drug cohesiveness by occupying the high-energy sites of the agent particles. Currently, lactose is the only excipient used in DPIs marketed in the United States. The reasons for this are as much historical as they are physicochemical/pharmaceutical in nature. Lactose had long been used as an excipient in oral dosage forms before being deployed in DPIs. It had an established safety and stability profile, manufacturing process with tight controls over purity and physical properties, and was available and inexpensive. Lactose is highly crystalline and has the smooth surfaces and satisfactory flow properties desirable for a DPI carrier particle. Other sugars, such as mannitol have been shown to be feasible alternatives to lactose. Phospholipids, such as phosphatidyl choline and cholesterol, have also been used in experimental liposomal formulations. Excipients can makes up over 99% of the product by weight, making them crucial determinants of overall DPI performance. The adhesive forces must be carefully considered;

inadequate separation of drug and carrier is the main reason for deposition problems. The formulator may also choose to modify the excipient before combining it with the drug. An excipient is not necessarily required for the functioning of a DPI, as known in the art.

It is known that loose agglomerates have been used as a means of stabilizing powder aerosols, so that, upon the introduction of energy from the patient's breath or some active source, loose agglomerate readily disperse into small particles for inhalation. These agglomerates can consist of particles of disparate sizes, as is the case when agent is prepared with large carrier particles, or particles of similar sizes prepared by unique methods of formation that result in ease of dispersion.

After drug and excipient(s) have individually been brought to their desired forms, they are combined in the blending process. The blending process is a critical step in the manufacture of a DPI product. After the formulation has been blended, it is filled into capsules, multi-dose blisters, or reservoirs for use with the inhaler device. In order to maintain its physical and chemical integrity and dispersibility, the product must be stored appropriately. Storage conditions, such as temperature and relative humidity profoundly effect DPI stability and performance, so permissible storage conditions need to be determined, as known in the art.

Regarding metered-dose inhalers (pMDIs), a formulation can be made up of the agent (e.g., a mucolytic thiosaccharide agent), a liquefied gas propellant and, in many cases, stabilizing excipients. The actuator contains the mating discharge nozzle and generally includes a dust cap to prevent contamination. Actuation of the device releases a single metered dose of the formulation which contains the medication either dissolved or suspended in the propellant. Breakup of the volatile propellant into droplets, followed by rapid evaporation of these droplets, results in the generation of an aerosol consisting of micrometer-sized medication particles that are then inhaled. One of the most crucial components of a MDI is its propellant. The propellant provides the force to generate the aerosol cloud and is also the medium in which the active component must be suspended or dissolved. Propellants in MDIs typically make up more than 99% of the delivered dose, so it is the properties of the propellant that dominate more than any other individual factor. Suitable propellants must pass a stringent set of criteria, they must: have a boiling point in the range −100 to +30° C. have a density of approximately 1.2 to 1.5 g $cm^{-3}$ (approximately that of the drug to be suspended or dissolved) have a vapor pressure of 40 to 80 psig have no toxicity to the patient, be non-flammable and be able to dissolve common additives. Active ingredients can be either fully soluble or fully insoluble. In the early days of MDIs the most commonly used propellants were the chlorofluorocarbons, but hydrofluoroalkane propellants are now preferred because they have fewer environmental toxicities. General considerations for metered dose inhalers include consideration of the following: agent is dissolved in the liquefied propellant, compliance with applicable rules (e.g., formulation agent (e.g., HFA propellant, surfactant, so-solvent and/or excipient)), container closure system (e.g., can, metering valve), actuator, and dose compliance device, as known in the art. Suspension formulation issues can include micronized drug particles suspended in the liquefied propellant (e.g., air, $CO_2$, HFA134a, 227 and the like). The suspension formulation may contain surfactant and co-solvent to aid suspension, particularly with respect irregular particles, polydispersed (e.g., 0.5-10 μm) particles, or amorphous/crystalline particles.

In embodiments of the pulmonary pharmaceutical composition, the pulmonary pharmaceutical carrier is a pulmonary pharmaceutical liquid or pulmonary pharmaceutical powder. In embodiments, the pulmonary pharmaceutical carrier is a pulmonary pharmaceutical liquid. In embodiments, the pulmonary pharmaceutical carrier is a pulmonary pharmaceutical powder.

In embodiments of the pulmonary pharmaceutical composition, the pulmonary pharmaceutical liquid comprises a polar liquid, and the thiosaccharide mucolytic agent is dissolved or suspended in the polar liquid. In embodiments, the polar liquid is water.

In embodiments of the pulmonary pharmaceutical composition, the pulmonary pharmaceutical carrier is lactose, mannitol, a phospholipid or cholesterol. In embodiments, the phospholipid is phosphatidyl choline. In embodiments, the pulmonary pharmaceutical carrier is the parent sugar of the thiosaccharide mucolytic agent, wherein the parent sugar lacks a thiol moiety, e.g., D-glucopyranose, D-galactopyranose, D-mannopyranose, D-glucopyranoside, D-galactopyranoside, or D-mannopyranoside.

In embodiments of the pulmonary pharmaceutical composition, the pulmonary pharmaceutical composition is within a pulmonary pharmaceutical delivery device. In embodiments, the pulmonary pharmaceutical delivery device is a pulmonary pharmaceutical nebulizer, a pulmonary pharmaceutical dry powder inhaler, or a pulmonary pharmaceutical pressurized metered dose inhaler.

In embodiments of the pulmonary pharmaceutical composition, the pulmonary pharmaceutical composition further includes one or more additional therapeutic agents. In embodiments, the pulmonary pharmaceutical composition further includes one additional therapeutic agent. In embodiments, the pulmonary pharmaceutical composition further includes a plurality of additional therapeutic agents. In embodiments, the pulmonary pharmaceutical composition further includes two additional therapeutic agents. In embodiments, the pulmonary pharmaceutical composition further includes three additional therapeutic agents. In embodiments, the pulmonary pharmaceutical composition further includes four additional therapeutic agents.

In embodiments, the additional therapeutic agent is a beta agonist, as known in the art. In embodiments, the additional therapeutic agent is a short-acting beta agonist, as known in the art. In embodiments, the additional therapeutic agent is a long-acting beta agonist, as known in the art. The term "short-acting" in the context of therapeutic agents refers, in the usual and customary sense, a therapeutic agent that elicits a transient effect, e.g., 1-60 seconds, 1-60 minutes, 1, 2, 3, 4, 5, 6, 7, 8, 9, 10, 11 or even 12 hours, as known in the art. The term "long-acting" in the context of therapeutic agents refers, in the usual and customary sense, a therapeutic agent that elicits a sustained effect, e.g., 1, 2, 3, 4, 5, 6, 7, 8, 9, 10, 11, 12, 13, 14, 15, 16, 17, 18, 19, 20, 21, 22, 23 or even 24 hours, 1, 2, 3, 4, 5, 6, or even 7 days, 1, 2, 3, 4 weeks or longer, as known in the art.

In embodiments, the additional therapeutic agent is a anticholinergic, as known in the art. In embodiments, the additional therapeutic agent is a short-acting anticholinergic, as known in the art. In embodiments, the additional therapeutic agent is a long-acting anticholinergic, as known in the art.

In embodiments, the additional therapeutic agent is a steroid as disclosed herein or as known in the art, e.g., fluticasone, budesonide, beclomethasone, momethasone. In embodiments, the additional therapeutic agent is a corticosteroid as disclosed herein or as known in the art.

In embodiments, the additional therapeutic agent is an antibiotic, as known in the art.

In embodiments, the additional therapeutic agent is rhDNAse, as known in the art.

B. Effective Dosages

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated.

The dosage and frequency (single or multiple doses) of compound administered can vary depending upon a variety of factors, including route of administration; size, age, sex, health, body weight, body mass index, and diet of the recipient; nature and extent of symptoms of the disease being treated; presence of other diseases or other health-related problems; kind of concurrent treatment; and complications from any disease or treatment regimen. Other therapeutic regimens or agents can be used in conjunction with the methods and compounds of the invention.

Therapeutically effective amounts for use in humans may be determined from animal models. For example, a dose for humans can be formulated to achieve a concentration that has been found to be effective in animals.

Dosages may be varied depending upon the requirements of the patient and the compound being employed. The dose administered to a patient, in the context of the present invention, should be sufficient to effect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See e.g., Fingl et al., In: THE PHARMACOLOGICAL BASIS OF THERAPEUTICS, Ch. 1, p. 1, 1975. The exact formulation, route of administration, and dosage can be chosen by the individual physician in view of the patient's condition and the particular method in which the compound is used.

V. Examples

Example 1. Chemical Synthesis

Example 1.1. General Methods

The $^1H/^{13}C$ NMR spectra (δ in ppm, relative to TMS in $CDCl_3$) were recorded with Varian spectrometers (400/100 MHz or 500/125 MHz) at 25° C. Assignments were aided by $^1H$-$^1H$ and $^1H$-$^{13}C$ correlation experiments. HRMS spectra were recorded on a micromass LCT instrument from Waters. Optical rotations were measured on a Perkin Elmer polarimeter with a Na lamp (589 nm) at 20° C. and are not corrected. TLC was carried out on precoated 60 F254 silica gel alumina plates (Merck) using UV-light and/or $H_2SO_4$ (10% in ethanol). Flash chromatography (FC) was performed on silica gel via pre-packed columns (Biotage AB, particle size 50 m) on a Biotage SP4 system.

Example 1.2. Synthesis of Methyl 2,3,4-Tri-O-acetyl-6-O-tosyl-α-D-galactopyranoside (Reagent R1)

A solution of tosyl chloride (0.540 g, 2.83 mmol) in dry pyridine (2.5 mL) was added to an ice cooled solution of methyl α-D-galactopyranoside (0.500 g, 2.57 mmol) in dry pyridine (5 mL) and the reaction was stirred while allowing to warm up to room temperature. After 4 h stirring a substantial amount of starting material was still detected by TLC (Eluent: EtOAc-MeOH 4:1). Additional tosyl chloride (0.442 g, 2.32 mmol) dissolved in pyridine (2.5 mL) was added and the mixture was stirred overnight. MeOH (2 mL) was then added and the mixture concentrated and co-evaporated with toluene (3×10 mL). The residue was taken up into pyridine (4 mL), acetic anhydride (2 mL) added and the mixture stirred overnight. The mixture was then concentrated and co-evaporated with toluene (3×10 mL), dissolved in EtOAc (30 mL), the solution washed with satd aq $NaHCO_3$ (20 mL), the organic layer dried over $MgSO_4$, filtered and concentrated. The crude was purified by FC on silica gel via Biotage (toluene-EtOAc) to give R1 (0.639 g, 52%) as a colourless solid. See e.g., Zaliz, C. L. R.; Varela, O.; *J. Carbohydr. Chem.*, 2001, 20, 689-701. $R_f$ 0.53 (toluene-EtOAc 2:1); $[\alpha]_D^{20}$+920 (c 0.87, $CHCl_3$); $^1H$ NMR (400 MHz, $CDCl_3$) δ 7.78-7.72 (m, 2H, Ar), 7.36-7.30 (m, 2H, Ar), 5.37 (dd, $J_{3,4}$=3.4 Hz, $J_{4,5}$=1.0 Hz, 1H, H-4), 5.27 (dd, $J_{2,3}$=10.8 Hz, $J_{3,4}$=3.4 Hz, 1H, H-3), 5.07 (dd, $J_{2,3}$=10.8 Hz, $J_{1,2}$=3.6 Hz, 1H, H-2), 4.92 (d, $J_{1,2}$=3.6 Hz, 1H, H-1), 4.20-4.13 (m, 1H, H-5), 4.06 (dd, $J_{6a,b}$=10.2 Hz, $J_{6a}$=6.9 Hz, 1H, H-6a), 3.98 (dd, $J_{6a,b}$=10.2 Hz, $J_{5,6b}$=5.6 Hz, 1H, H-6b), 3.34 (s, 3H, $C^1OCH_3$), 2.44 (s, 3H, —$C_6H_4OCH_3$), 2.05, 2.03 and 1.94 (3 s, 9H, $OCOCH_3$) ppm. $^{13}C$ NMR (100 MHz, $CDCl_3$) δ 170.4, 170.0, 169.8 (3C, —$OCOCH_3$), 145.2, 132.5, 129.9 and 128.0 (6 C, Ar), 97.1 (C-1), 68.0 (C-4), 67.9 (C-2), 67.3 (C-3), 67.0 (C-6), 66.2 (C-5), 55.6 (—$C^1OCH_3$), 21.7 ($C_6H_4OCH_3$), 20.8, 20.6 and 20.5 (3 C, —$OCOCH_3$) ppm. ES-HRMS calcd for $C_{20}H_{26}O_{11}S$ $[Na]^+$ 497.1094 found 497.1088.

Example 1.3. Synthesis of Methyl 2,3,4-Tri-O-acetyl-6-deoxy-6-thioacetyl-α-D-galactopyranoside (Reagent R2)

Potassium thioacetate (1.70 g, 14.9 mmol) was added to a solution of reagent R1 (1.77 g, 3.73 mmol) in DMF (20 mL) and stirred with at 90 OC overnight. The mixture was cooled down to room temperature, diluted with toluene and EtOAc (1:1, 100 mL) and washed with water (50 mL) and satd aq $NaHCO_3$ (50 mL). The organic layer was dried over $MgSO_4$, concentrated and two times purified by FC on silica gel via Biotage (Eluent: toluene-EtOAc). The obtained slightly yellowish residue was dissolved in $CH_2Cl_2$ (50 mL) and stirred with activated charcoal over night. The charcoal was filtered off and the mixture concentrated and dried in-vacuo to obtain R2 as a colourless solid (1.05 g, 74%). See e.g., Elhalabi, J.; Rice, K. G.; *Carbohydr. Res.*, 2002, 337, 1935-1940. $R_f$ 0.59 (toluene-EtOAc 2:1); $[α]^2$+1410 (c 1.15, $CHCl_3$); $^1$H NMR (500 MHz, $CDCl_3$) δ 5.50-5.41 (m, 1H, H-4), 5.31 (dd, $J_{2,3}$=10.8 Hz, $J_{3,4}$=3.3 Hz, 1H, H-3), 5.13 (dd, $J_{2,3}$=10.8 Hz, $J_{1,2}$=3.6 Hz, 1H, H-2), 4.96 (d, $J_{1,2}$=3.6 Hz, 1H, H-1), 3.97 (m, 1H, H-5), 3.41 (s, 3H, —$OCH_3$), 3.06 (dd, $J_{6a,b}$=13.8 Hz, $J_{5,6a}$=6.6 Hz, 1H, H-6a), 2.98 (dd, $J_{6a,b}$=13.8 Hz, $J_{5,6b}$=7.6 Hz, 1H), 2.34 (s, 3H, —$SCOCH_3$) 2.17, 2.08 and 1.98 (s, 9H, —$OCOCH_3$) ppm. $^{13}$C NMR (125 MHz, $CDCl_3$) δ 194.5 (—$SCOCH_3$), 170.4, 170.3 and 169.9 (3C, —$OCOCH_3$), 97.2 (C-1), 69.1 (C-4), 68.1 (C-2), 67.8 (C-3), 67.5 (C-5), 55.4 (—$OCH_3$), 30.5 (C-6), 28.7 (—$SCOCH_3$), 20.8, 20.7 and 20.7 (3C, —$OCOCH_3$). ES-HRMS calcd for $C_{15}H_{22}O9_s$ $[Na]^+$ 401.0882 found 401.0890.

Example 1.4. Synthesis of Methyl 6-deoxy-6-thio-α-D-galactopyranoside (Reagent R3)

A solution of sodium methoxide (1N in MeOH) was added to R2 (0.272 g, 0.719 mmol) in dry MeOH (5 mL) under a $N_2$ atmosphere until pH=13 was reached and the resulting mixture was stirred for 3 h. After completion of the reaction the mixture was neutralized with Dowex 50 W+ ion exchange resin, the resin filtered off and the solution concentrated. The solid was taken up into water and freeze dried to obtain R3 (137 mg, 91%) as a colourless solid. See e.g., Konstantinovic, S. et al., *J. Serbian Chem. Soc.*, 2005, 70(7):925-929. $R_f$ 0.53 (EtOAc-MeOH—$H_2O$ 4:1:1); $[α]_D^{20}$+139° (c 1.00, $H_2O$); $^1$H NMR (400 MHz, $D_2O$) δ 4.85-4.83 (m, 1H, H-1), 4.08-4.06 (m, 1H, H-4), 3.90-3.85 (m, 1H, H-5), 3.84-3.82 (m, 2H, H-2, H-3), 3.47 (s, 3H, —$OCH_3$), 2.80 (dd, $J_{6a,b}$=13.7, $J_{5,6a}$=8.1 Hz, 1H, H-6a), 2.74 (dd, $J_{6a,b}$=13.7, $J_{5,6b}$=5.8 Hz, 1H, H-6b) ppm. $^{13}$C NMR (100 MHz, $D_2O$) δ 99.4 (C-1), 72.1 (C-5), 69.5 (C-4), 69.4 and 68.0 (C-2, C-3), 55.07 (—$OCH_3$), 23.87 (C-6) ppm. ES-HRMS calcd for $C_7H_{14}O_5S$ $[Na]^+$233.0460 found 233.0471.

Example 1.5. Synthesis of 5-Thioacetoxypentyl 2,3,4,6-tetra-O-acetyl-β-D-galactopyranoside (R4)

A solution of thioacetic acid (0.6 ml, 8.6 mmol) and AIBN (0.20 g) was added into a solution of R3 (0.36 mg, 0.86 mmol) in dry 1,4-dioxane (10 mL). The reaction mixture was then thoroughly degassed under an atmosphere of nitrogen. Thereafter, the reaction was refluxed at a temperature of 75° C. under an atmosphere of nitrogen for 1-4 hrs, with constant monitoring at every hour by TLC. After complete reaction the mixture was allowed to cool down to room temperature and was then concentrated. The crude residue was purified by FC on silica gel (cyclohexane-EtOAc) to afford R4 (0.338 mg, 94%). $[α]_D$–16.2° (c 0.5, $CHCl_3$); $^1$H NMR ($CDCl_3$) δ 1.26-1.63 (dd, 6H), 2.00, 2.02, 2.05, 2.08 (s, 3H each), 2.32 (s, 3H), 2.85 (t, 2H), 3.47 (m, 1H), 3.68 (m, H), 4.15, 4.28 (dd, 1H each), 4.50 (d, 1H, J), 4.98, 5.08, 5.21 (dd, 1H each); $^{13}$C NMR ($CDCl_3$): δ 20.6 (2 signals), 20.7 (2 signals), 25.0, 28.8, 28.9, 29.1, 30.6, 61.9, 68.4, 69.7, 71.3, 71.7, 72.8, 100.7, 169.3, 169.4, 170.3, 170.7, 195.8.

Example 1.6. Synthesis of methyl 6-deoxy-6-thio-α-D-galactopyranoside (Cmpd 1)

Synthesis of Cmpd 1 followed the strategy of Scheme 1 following.

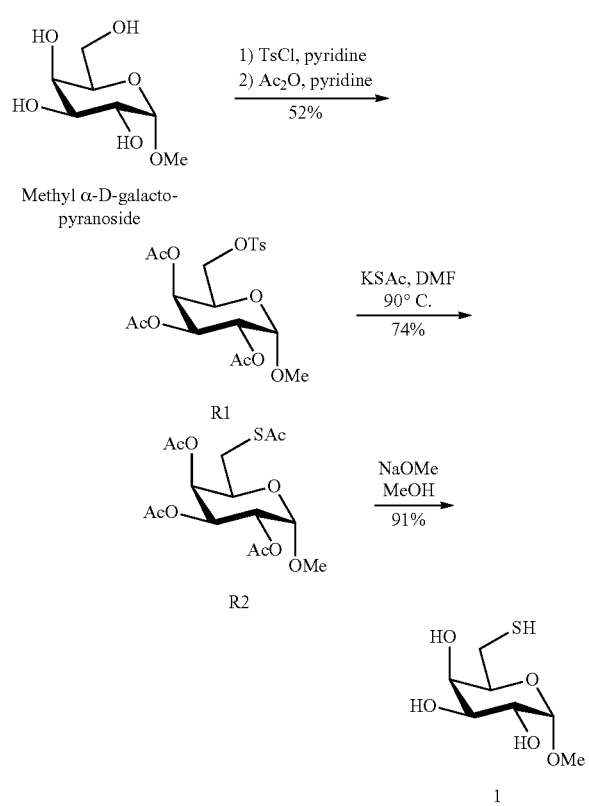

Scheme 1.

Methyl 6-deoxy-6-thio-α-D-galactopyranoside (Cmpd 1) was synthesized from commercially available methyl α-D-galactopyranoside in four steps and an overall yield of 35% (Scheme 1). Selective tosylation at the primary position followed by acetylation afforded reagent R1, in which the tosyl group was replaced by a thioacetate group to give reagent R2, which was deacetylated using Zemplen conditions to afford Cmpd 1.

Example 1.7. Synthesis of 5-Thiopentyl β-D-galactopyranoside (Cmpd 2)

Synthesis of Cmpd 2 followed the strategy of Scheme 2 following.

Scheme 2.

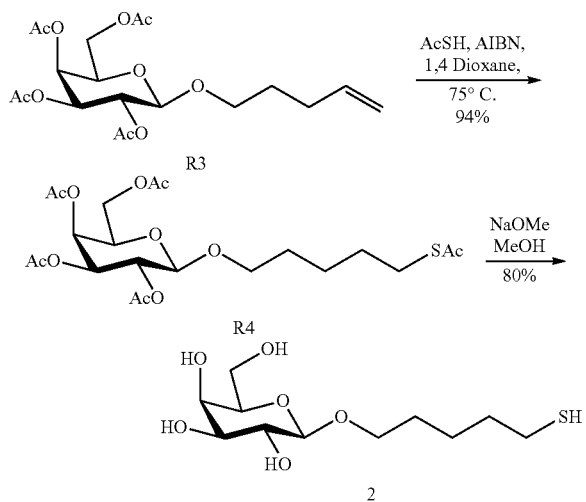

5-Thiolpentyl β-D-galactopyranoside (Cmpd 2) was synthesized in two steps from acetylated 4-pentenyl 3-D-galactopyranoside, R3. Radical addition of thioacetic acid to the double bond gave reagent R4, which was deacetylated to afford Cmpd 2. See e.g., Buskas, T., et al., 2000, *J. Org. Chem.*, 65(4):958-963.

Compound reagent R4 (0.338 mg, 0.68 mmol) was deacetylated as described for compound R2 to give Cmpd 2 (0.55 mmol, 80%). $^1$H NMR (400 MHz, CDCl$_3$) δ 4.85-4.83 (m, 1H, H-1), 4.08-4.06 (m, 1H, H-4), 3.90-3.85 (m, 1H, H-5), 3.84-3.82 (m, 2H, H-2, H-3), 2.80 (dd, J$_{6a,b}$=13.7, J$_{5,6a}$=8.1 Hz, 1H, H-6a) ppm. $^{13}$C NMR (400 MHz, CDCl$_3$) δ 99.4 (C-1), 72.1 (C-5), 69.5 (C-4) ppm.

Example 2. Rheometric Studies

A rheometer was employed to determine the effect of the compounds disclosed herein on the elastic modulus (G') of sputum sample from human subjects. The terms "elastic modulus," "G'," and the like refer to the elastic modulus as known in the art. Inhalation of 3% saline facilitates mucus expectoration ("induced sputum") in human subjects, including in healthy subjects without lung disease. A typical sputum induction yields 3-5 mL of sputum, and induced sputum samples can be pooled from several donors in order to provide as much as 20 mL with for any given set of experiments. The rheometer can use 1 mL per assay. Rheological measurements can be made, e.g., with a AR2000 cone-and-plate rheometer (TA Instruments), as known in the art.

Patients with cystic fibrosis (CF) are able to spontaneously expectorate sputum samples. Sputum from CF patients has a higher elastic modulus than induced sputum from healthy subjects, e.g., patients not demonstrating symptoms of CF. We typically add the test compound to induced sputum at a 10% v/v, and we calculate effect of the test compound by measuring G' every 2 minutes for periods up to 20 minutes. Because oxidation can cause baseline drift, we keep the experiment under nitrogen to improve signal to noise ratios. We custom modified a cone and plate rheometer to permit this kind of control in our rheometry experiments. Another protocol element that we use to optimize signal to noise is the addition of protease inhibitors to CF sputum to inhibit protease digestion of mucin.

Example 3. Comparative Studies on Compound Efficacy

As depicted in FIG. 1, the elastic modulus (G') of pooled induced sputum from five healthy subjects was determined as a function of time in the presence of 1 mM PBS (phosphate buffered saline), NAC (N-acetylcysteine), Cmpd 1, Cmpd 29, Glc-NAc, and Gal-NAc.

Results.

At a concentration of 1 mM, N-acetylcysteine (i.e., a currently approved mucolytic drug) is not effective in decreasing G'. However, Cmpd 1 works well at 1 mM, decreasing G' by ~30%) during the time course of the experiment. Cmpd 29 provided approximately half of the decrease in G' observed with Cmpd 1 under these conditions.

Example 4. Disulfide Dimer Studies

Figure 2:
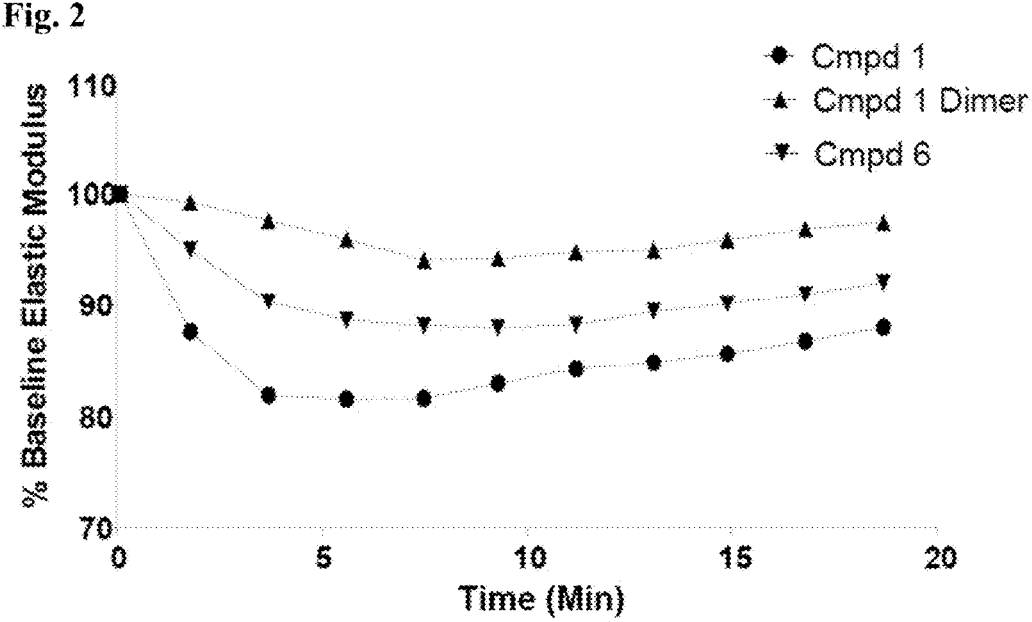
FIG. 2 depicts the effect of Cmpd 1 compared to a disulfide dimer of Cmpd 1 showing that the dimer is less effective than Cmpd 1. Also shown is the effect of Cmpd 6. All compounds are tested at 10 mM in this set of experiments. Legend: Cmpd 1 (circle); Cmpd 1 (dimer) (triangle tip up); Cmpd 6 (triangle tip down).
Figure 3:
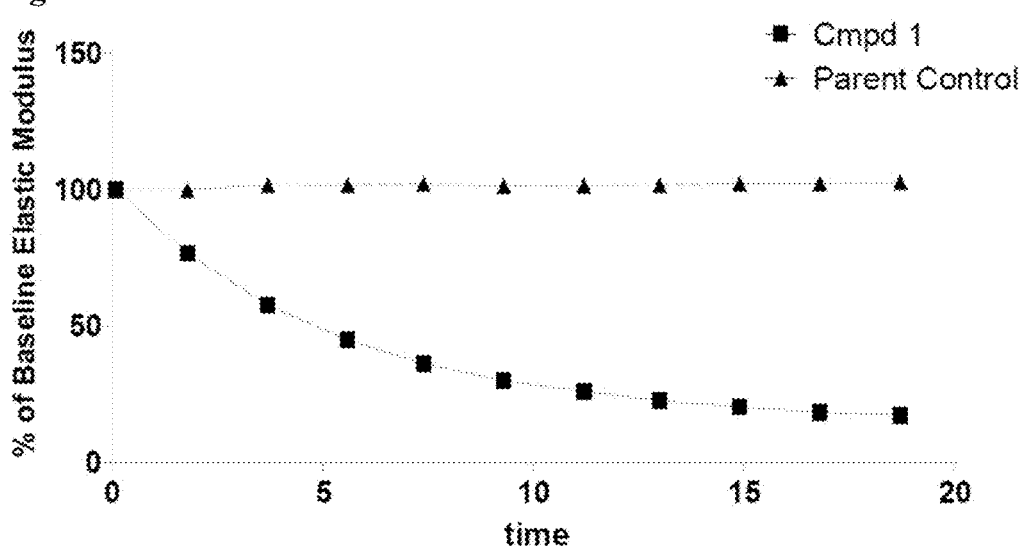
FIG. 3 depicts the effect of Cmpd 1 and the parent sugar of Cmpd 1 on the G' of CF sputum at 10 mM test compound concentration. The parent sugar is ineffective in decreasing G' of CF sputum under the test conditions. Legend: Cmpd 1 (box); parent sugar (triangle).

As depicted in FIG. 2, a comparative study was conducted on the efficacy of Cmpd 1, a disulfide dimer of Cmpd 1, and Cmpd 6. All compounds were tested at 10 mM to compare their effects on elastic modulus (G'). As shown in the figure, Cmpd 1 is more effective in reducing elastic modulus G' than either the disulfide dimer of Cmpd 1 or Cmpd 6.

Example 5. Comparison of Cmpd 1 and Parent on Sputum from CF Patients

Sputum from three patients with diagnosed CF was pooled. The elastic modulus G' of the pooled samples were determined as a function of time upon contacting with 10 mM Cmpd 1 or the parent sugar of Cmpd 1 (i.e., D-galactose). It is observed that effect of Cmpd 1 in CF sputum was larger than the effect in healthy induced sputum. Without wishing to be bound by any theory, it is believed likely that this reflects the higher starting G' of CF sputum and the more heavily disulfide bonded mucin polymers contained therein.

Example 6. Effect of Thiosaccharides on G' of Sputum from Separate CF Patients

Figure 4A:
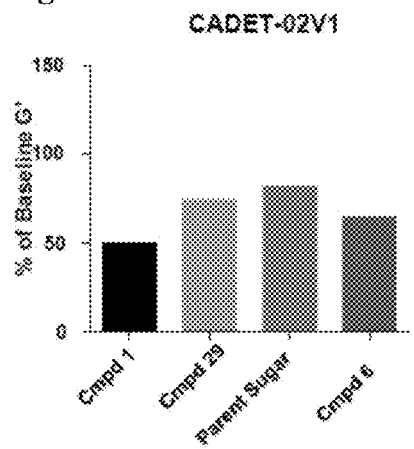
FIGS. 4A-4D depict histograms of change in elastic modulus G' (%-change relative to baseline) in sputum from three CF patients (FIGS. 4A-4C) and the average thereof (FIG. 4D) for rheometric studies conducted as disclosed herein. Test compounds (left to right): Cmpd 1, Cmpd 29, the parent sugar of Cmpd 1, and Cmpd 6.
Figure 4B:
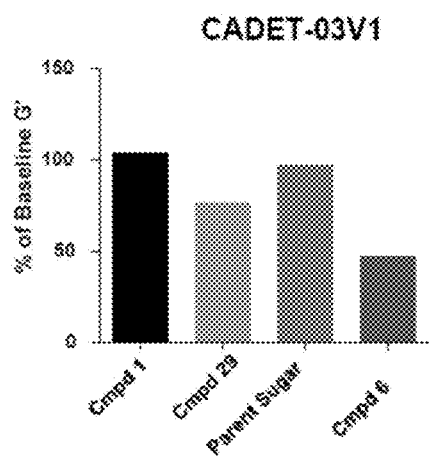
Figure 4C:
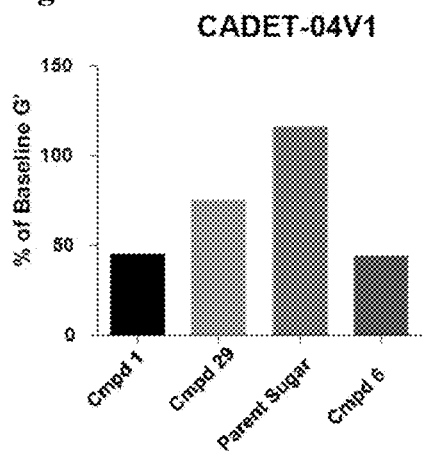
Figure 4D:
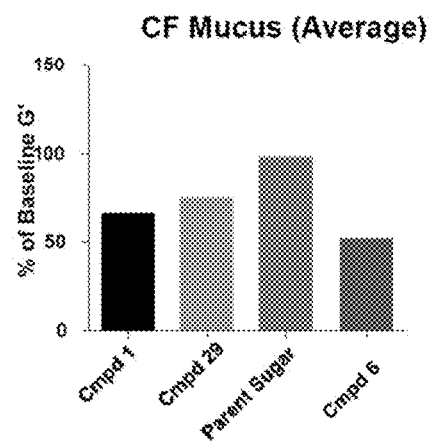

In order to determine the variability which can exist between individual sputum samples from CF patients and pooled samples of sputum from CF patients, an experiment was conducted employing individual sputum samples. As depicted in FIGS. 4A-4C, samples from individual CF patients (i.e., codes CADET-02V1, CADET-03C1 and CADET-04V1) were expressed and subjected to a rheometric analysis as described herein. The assayed compound were Cmpd 1, Cmpd 29, the parent sugar of Cmpd 1 (see Example 4), and the disulfide of Cmpd 1 and Cmpd 6. FIG. 4D provides a numeric average of the results depicted in FIGS. 4A-4C.

Results.

As depicted in FIGS. 4A-4D, Cmpd 1 demonstrates a large (i.e., ca. 50%) decrease in elastic modulus G' of individual sputum samples from CF patients.

Example 7

Comparison of Mucolytic Effects of N-Acetylcysteine and Cmpd 1 using averaged data from separate experiments in spontaneously expectorated sputum from five different patients with cystic fibrosis.

Figure 5A:
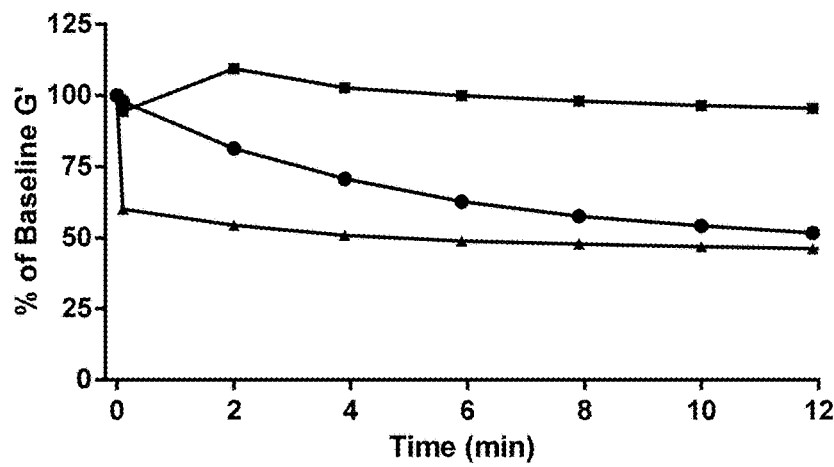
FIG. 5A: High concentrations (61 mM) of Cmpd 1 and N-acetyl cysteine (NAC) decrease the elastic modulus (G') (%-change from baseline) of CF sputum (n=5 donors) over a twelve-minute test period. The parent compound for Cmpd 1 (methyl α-D-galactopyranoside [MDG]) has no mucolytic effect.
Figure 5B:
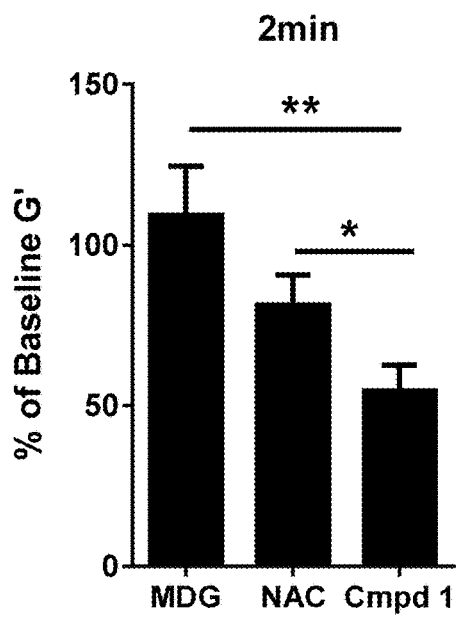
FIGS. 5B-5C.
Figure 5C:
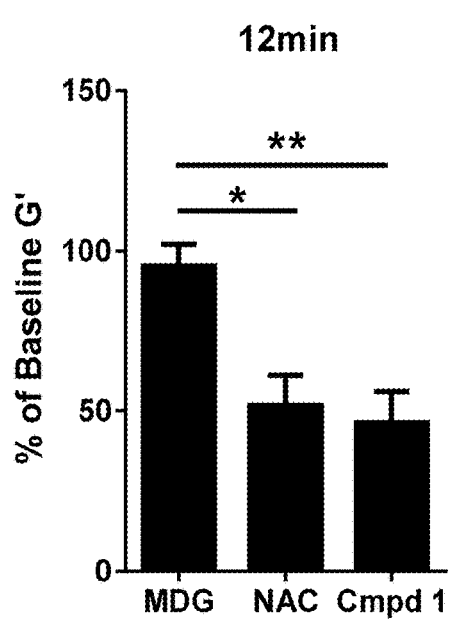

It is believed that oxidant-induced increases in mucus elasticity occur because mucin chains are extended via end-to-end disulfides between terminal cysteines or are cross-linked via side-to-side disulfides between internal cysteines. This mechanism implicates disulfides as therapeutic targets and reducing agents as rational mucolytic drugs. Indeed, N-acetylcysteine (NAC), an acetylated sulfur-containing amino acid, is a reducing agent that is used clinically as a mucolytic drug ("MUCOMYST®"). The mucolytic efficacy of NAC is limited, however, by relatively low potency, a potentially offensive (i.e., "rotten egg") smell, and airway irritant effects. In addition, NAC does not have mucolytic efficacy when given orally because lung concentrations are low or absent following oral delivery. We therefore considered the possibility that thiol-modified carbohydrates might be better reducing agents than NAC and candidates as novel mucolytic drugs. Carbohydrate scaffolds are polar, cheap, natural, often crystalline, and offer easy access to analogues for structure activity relationship studies. The abundance of hydroxyl groups as well as chiral centers on carbohydrate scaffolds allows many possibilities for the introduction of a thiol group. For example, one approach is to introduce the thiol onto the scaffold by direct displacement of a hydroxyl group with a thiol group. Thus, a methyl α-D-galactopyranoside (MDG) was modified with a thiol at the 6-position and stabilized as a methyl glycoside: Cmpd 1. In comparing the relative effects of high concentrations (61 mM) of Parent Sugar (MDG), Cmpd 1, and NAC on the elastic properties of CF sputum samples over a twelve-minute test period (FIG. 5A), it was observed that Cmpd 1 has much larger mucolytic effects than NAC at two minutes and similar effects at 12 minutes. See FIGS. 5B-5C. Thus, Cmpd 1 provides a significantly faster onset of action relative to either parent sugar MDG or NAC.

Example 8. Studies for Parent Sugar MDG and Cmpds 1-5

Figure 6:
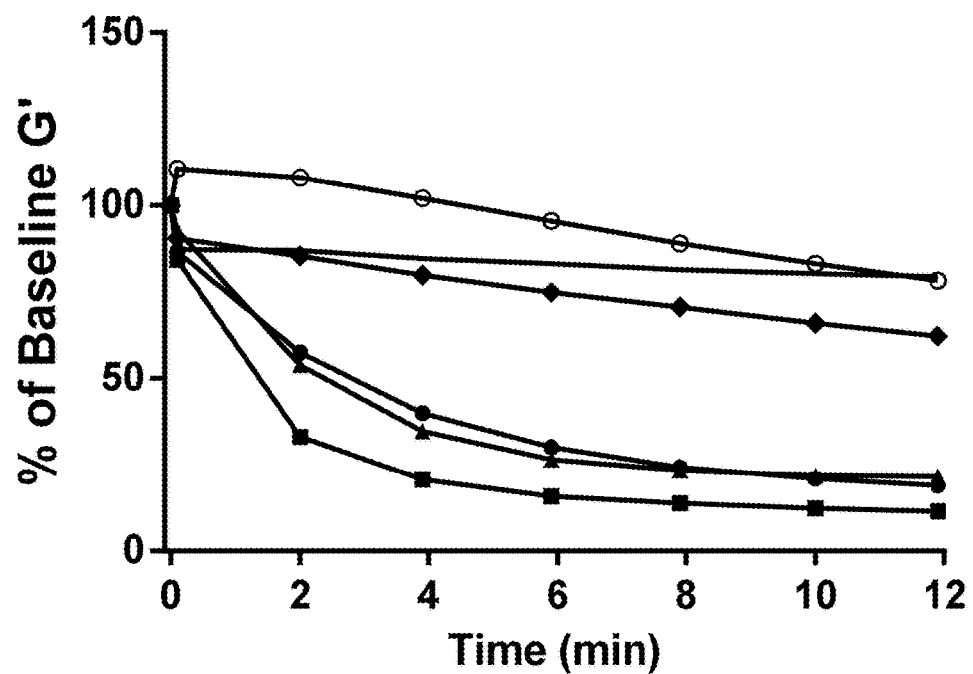
FIG. 6 depicts time courses (0-12 min) of screening assays for change in elastic modulus G' (%-change from baseline) for sputum samples (n=1 subject) for parent sugar MDG and Cmpds 1, 2, 3, 4 and 5, each at 10 mM. Legend: MDG (solid line); Cmpd 1 (solid circle); Cmpd 2 (solid square); Cmpd 3 (solid triangle); Cmpd 4 (open circle); Cmpd 5 (solid diamond).

A series of time courses of the change in baseline G' (%-change from baseline) of sputum samples at 10 mM concentration of MDG and Cmpds 1-5 is depicted in FIG. 6. Each datum in the figure was obtained from a single sputum sample from a patient with cystic fibrosis. These data of FIG. 6 indicate that a galactose moiety (i.e., Cmpd 2) affords a better mucolytic than mannose (Cmpd 5) or glucose (Cmpd 4), with respect to both onset of mucolysis and endpoint (12-minutes). Moreover, the length of the chain leading to the thiol is important; compare Cmpd 2 ($C_5$ alkylene) vs. Cmpd 3 ($C_2$ alkylene).

Example 9. Mucolytic Effect of Low Doses (10 mM) of Parent Sugar MDF, NAC, GSH and Cmpd 2

Figure 7A:
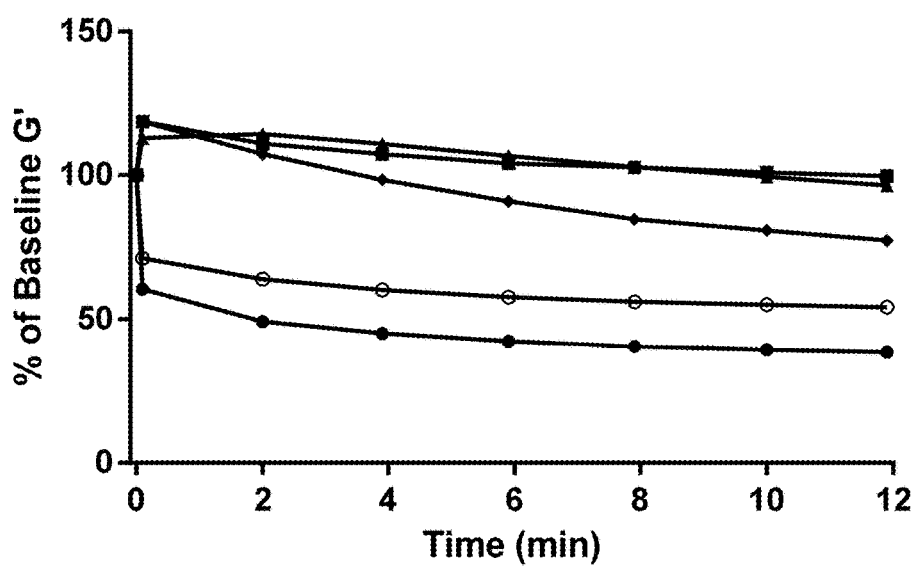
FIG. 7A depicts course of change in elastic modulus (G') (%-change from baseline) over time. Data were averaged from experiments using sputum from five different Cystic Fibrosis (CF) subjects.
Figure 7B:
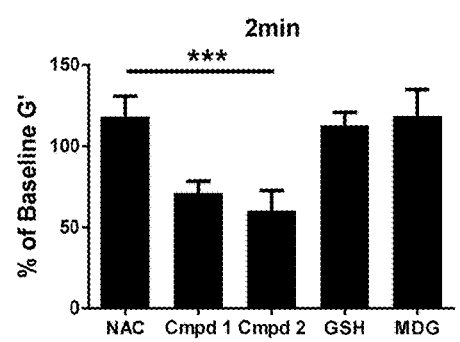
FIGS. 7B-7C.
Figure 7C:
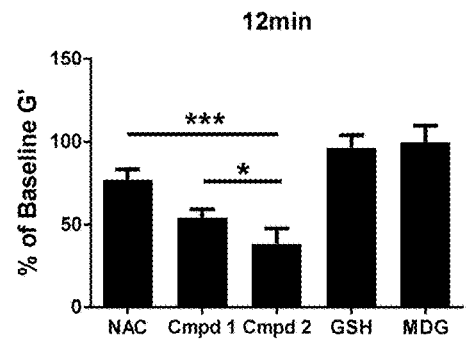

A time course of the change in baseline G' (%-change from baseline) at 10 mM concentration of thiosaccharide is depicted in FIG. 7A. The drugs compared include an unmodified sugar (MDG), Glutathione (GSH, a natural endogenous reducing agent), N-acetyl cysteine (NAC), Cmpd 1 and Cmpd 2. We found that Cmpd 2 had much larger mucolytic effects than NAC at both two minutes (FIG. 7B) and 12 minutes (FIG. 7C). Indeed, NAC was no better than control solutions at this 10 mM concentration, and the mucolytic effect of Cmpd 2 is significantly greater than that of Cmpd 1 at the 12-minute time-point (FIG. 7C).

Example 10. Oxidation-Reduction Potential (ORP) Measurements

Method.

An INLAB® Redox Micro ORP probe (Mettler Toledo) was employed, which utilizes a small platinum ring indicator electrode and a 3M KCL reference electrolyte. ORP values were determined for thiosaccharides, NAC and glutathione.

Results.

As shown in Table 1 following, compared to a parent sugar (PS) control, the NAC and glutathione (GSH) solutions (1 mM) did not have strong reducing properties. In contrast, Cmpd 1 had relatively strong reducing capabilities, and Cmpd 2 had an ORP values that was negative relative to control, indicating very strong reducing activity.

TABLE 1

Comparison of reducing capacity of thiosaccharides compared to NAC and GSH.

| Cmpd | Reducing capacity (mV) |
| --- | --- |
| Parent Sugar | 176 |
| Cmpd 1 | 99 |
| NAC | 121 |
| GSH | 140 |
| Cmpd 2 | −15 |

VI. Embodiments

Embodiments include embodiments P1-P93 following:

Embodiment P1

A method of decreasing mucus elasticity or decreasing mucus viscosity in a subject in need thereof, said method comprising administering to said subject an effective amount of a thiosaccharide mucolytic agent.

Embodiment P2

The method of embodiment P1, wherein said method comprises decreasing mucus viscoelasticity in said subject.

Embodiment P3

The method of embodiment P1, wherein said thiosaccharide mucolytic agent is a thiol monosaccharide mucolytic agent, a thiol disaccharide mucolytic agent, or a thiol trisaccharide mucolytic agent.

Embodiment P4

The method of embodiment P1, wherein said thiosaccharide mucolytic agent comprises D-glucopyranose, D-galactopyranose, D-mannopyranose, D-glucopyranoside, D-galactopyranoside, or D-mannopyranoside moieties.

Embodiment P5

The method of embodiment P1, wherein said thiosaccharide mucolytic agent has the formula:

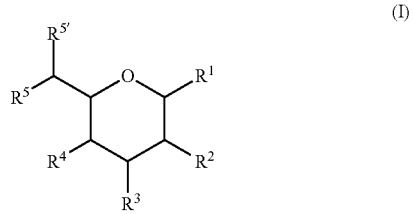

(I)

wherein, $R^1$ is —SH, —OR$^{1A}$, —NR$^{1B}$ or —R$^{1D}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —C(O)R$^{1C}$, substituted or unsubstituted $C_1$-$C_{10}$ thiol-alkyl or substituted or unsubstituted 2 to 10 membered thiol-heteroalkyl; $R^{1C}$ is substituted or unsubstituted $C_1$-$C_{10}$ thiol-alkyl or substituted or unsubstituted 2 to 10 membered thiol-heteroalkyl; and $R^{1D}$ is substituted or unsubstituted $C_1$-$C_{10}$ thiol-alkyl or substituted or unsubstituted 2 to 10 membered thiol-heteroalkyl; $R^2$—SH, —OR$^{2A}$ or —NR$^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —C(O)R$^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$—SH, —OR$^{3A}$ or NR$^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —C(O)R$^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^4$ is —SH, —SAc, —OR$^{4A}$ or —NR$^{4B}$, wherein $R^{4A}$ is H, substituted or unsubstituted $C_1$-$C_{10}$ thiol-alkyl or substituted or unsubstituted 2 to 10 membered thiol-heteroalkyl; $R^{4B}$ is —C(O)R$^{4C}$, substituted or unsubstituted $C_1$-$C_{10}$ thiol-alkyl or substituted or unsubstituted 2 to 10 membered thiol-heteroalkyl; and $R^{4C}$ is substituted or unsubstituted $C_1$-$C_{10}$ thiol-alkyl or substituted or unsubstituted 2 to 10 membered thiol-heteroalkyl; and $R^5$ is H, —SH, —SAc, —OR$^{5A}$, —NR$^{5B}$, or —R$^{5D}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —C(O)R$^{5C}$, substituted or unsubstituted $C_1$-$C_{10}$ thiol-alkyl or substituted or unsubstituted 2 to 10 membered thiol-heteroalkyl; $R^{5C}$ is substituted or unsubstituted $C_1$-$C_{10}$ thiol-alkyl or substituted or unsubstituted 2 to 10 membered thiol-heteroalkyl; and $R^{5D}$ is substituted or unsubstituted $C_1$-$C_{10}$ thiol-alkyl; and $R^{5'}$ is H or —OH.

Embodiment P6

The method of embodiment P5, wherein $R^1$, $R^3$, $R^4$ and $R^5$ are —OH; $R^{5'}$ is H; $R^{2A}$ is an unsubstituted $C_1$-$C_{10}$ thiol-alkyl or unsubstituted 2 to 10 membered thiol-heteroalkyl; $R^{2B}$ is —C(O)R$^{2C}$, unsubstituted $C_1$-$C_{10}$ thiol-alkyl or unsubstituted thiol-heteroalkyl; and $R^{2C}$ is substituted or unsubstituted $C_1$-$C_{10}$ thiol-alkyl or substituted or unsubstituted 2 to 10 membered thiol-heteroalkyl.

Embodiment P7

The method of embodiment P6, wherein $R^2$ is —NR$^{2B}$.

Embodiment P8

The method of one of embodiments P5 to P7, wherein $R^{2B}$ is —C(O)R$^{2C}$.

Embodiment P9

The method of one of embodiments P5 to P8, wherein $R^{2C}$ is $R^{2C1}$-substituted $C_1$-$C_{10}$ thiol-alkyl or $R^{2C1}$-substituted 2 to 10 membered thiol-heteroalkyl, wherein $R^{2C1}$ is —N(H)C(O)R$^{2C2}$, wherein $R^{2C2}$ is unsubstituted $C_1$-$C_{10}$ alkyl.

Embodiment P10

The method of embodiment P9, wherein $R^{2C2}$ is methyl.

Embodiment P11

The method of embodiment P10, wherein $R^{2A}$ is —N(H)—C(O)—CH(NHAc)—CH$_2$—SH.

Embodiment P12

The method of embodiment P5, wherein $R^2$, $R^3$, $R^4$ are —OH.

Embodiment P13

The method of embodiment P12, wherein $R^{5'}$ is H; $R^5$ is —SH, —OR$^{5A}$ or —NR$^{5B}$, wherein $R^{5A}$ unsubstituted $C_1$-$C_{10}$ thiol-alkyl or unsubstituted 2 to 10 membered thiol-heteroalkyl; $R^{5B}$ is —C(O)R$^{5C}$, unsubstituted $C_1$-$C_{10}$ thiol-alkyl or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl.

Embodiment P14

The method of embodiment P13, wherein $R^5$ is —SH.

Embodiment P15

The method of one of embodiments P12 to P14, wherein $R^1$ is OR$^{1A}$.

Embodiment P16

The method of one of embodiments P12 to P15, wherein $R^{1A}$ is unsubstituted $C_1$-$C_5$ alkyl.

Embodiment P17

The method of one of embodiments P12 to P16, wherein $R^{1A}$ is methyl.

Embodiment P18

The method of embodiment P5, wherein $R^3$, $R^4$ and $R^5$ are —OH; and R5' is H.

Embodiment P19

The method of embodiment P18, wherein $R^2$ is —OH.

Embodiment P20

The method of embodiment P19, wherein $R^1$ is —SH, —$OR^{1A}$ or —$NR^{1B}$, wherein $R^{1A}$ is unsubstituted $C_1$-$C_{10}$ thiol-alkyl or unsubstituted 2 to 10 membered 10 thiol-heteroalkyl; $R^{1B}$ is —$C(O)R^{1C}$, unsubstituted $C_1$-$C_{10}$ thiol-alkyl or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl.

Embodiment P21

The method of embodiment P21, wherein $R^1$ is —$OR^{1A}$ and $R^{1A}$ is unsubstituted $C_1$-$C_{10}$ thiol-alkyl.

Embodiment P22

The method of embodiment P18, wherein $R^1$ is —OH.

Embodiment P23

The method of embodiment P22, wherein $R^2$ is —SH, —$OR^{2A}$ or —$NR^{2B}$, wherein $R^{2A}$ is unsubstituted $C_1$-$C_{10}$ thiol-alkyl or unsubstituted 2 to 10 membered thiol-heteroalkyl; $R^{2B}$ is —$C(O)R^{2C}$, unsubstituted $C_1$-$C_{10}$ thiol-alkyl or unsubstituted 2 to 10 membered thiol-heteroalkyl; and $R^{2C}$ is substituted or unsubstituted $C_1$-$C_{10}$ thiol-alkyl or substituted or unsubstituted 2 to 10 membered thiol-heteroalkyl.

Embodiment P24

The method of embodiment P23, wherein $R^2$ is —$NR^{2B}$, and $R^{2B}$ is —$C(O)R^{2C}$.

Embodiment P25

The method of embodiment P24, wherein $R^{2C}$ is unsubstituted $C_1$-$C_{10}$ thiol-alkyl.

Embodiment P26

The method of embodiment P5, wherein $R^4$ is —SH.

Embodiment P27

The method of embodiment P26, wherein $R^1$ is —$OR^{1A}$; and $R^2$, $R^3$, and $R^5$ are —OH.

Embodiment P28

The method of embodiment P27, wherein $R^{1A}$ is unsubstituted $C_1$-$C_{10}$ alkyl.

Embodiment P29

The method of embodiment P28, wherein $R^{1A}$ is methyl.

Embodiment P30

The method of embodiment P5, wherein $R^5$ is —SH; and $R^{5'}$ is H.

Embodiment P31

The method of embodiment P30, wherein $R^1$ is —$OR^{1A}$; and $R^2$, $R^3$, and $R^4$ are —OH.

Embodiment P32

The method of embodiment P31, $R^{1A}$ is unsubstituted $C_1$-$C_{10}$ alkyl.

Embodiment P33

The method of embodiment P32, wherein $R^{1A}$ is methyl.

Embodiment P34

The method of embodiment P5, wherein $R^1$ is —$OR^{1A}$; $R^2$, $R^3$, and $R^4$ are —OH; $R^5$ is H or —$OR^{5A}$; and $R^{5'}$ is H.

Embodiment P35

The method of embodiment P34, wherein $R^5$ is H.

Embodiment P36

The method of embodiment P35, wherein $R^{1A}$ is substituted or unsubstituted $C_1$-$C_{10}$ thiol-alkyl or substituted or unsubstituted 2 to 10 membered thiol-heteroalkyl.

Embodiment P37

The method of embodiment P36, wherein $R^{1A}$ is unsubstituted $C_1$-$C_{10}$ thiol-alkyl.

Embodiment P38

The method of embodiment P37, wherein $R^{1A}$ is thiopropyl.

Embodiment P39

The method of embodiment P34, wherein $R^5$ is —$OR^{5A}$.

Embodiment P40

The method of embodiment P39, wherein $R^5$ is —OH.

Embodiment P41

The method of embodiment P40, wherein $R^{1A}$ is unsubstituted $C_1$-$C_{10}$ thiol-alkyl.

Embodiment P42

The method of embodiment P41, wherein $R^{1A}$ is thiopropyl.

Embodiment P43

The method of embodiment P34, wherein $R^{1A}$ is substituted or unsubstituted $C_1$-$C_{10}$ thiol-alkyl or substituted or unsubstituted 2 to 10 membered thiol-heteroalkyl.

Embodiment P44

The method of embodiment P43, wherein $R^5$ is —OH; and $R^{1A}$ is or unsubstituted $C_1$-$C_{10}$ thiol-alkyl or unsubstituted 2 to 10 membered thiol-heteroalkyl.

Embodiment P45

The method of embodiment P44, wherein $R^{1A}$ is unsubstituted $C_1$-$C_{10}$ thiol-alkyl.

Embodiment P46

The method of embodiment P45, wherein $R^{1A}$ is thioethyl, thiopropyl, thiobutyl, or thiopentyl.

Embodiment P47

The method of embodiment P44, wherein $R^{1A}$ is unsubstituted 2 to 10 membered thiol-heteroalkyl.

Embodiment P48

The method of embodiment P47, wherein $R^{1A}$ is thioethyloxyethyl.

Embodiment P49

The method of embodiment P5, wherein $R^1$ is —$OR^{1A}$; $R^2$, $R^3$, and $R^4$ are —OH; $R^{5'}$ is H; and $R^5$ is —SH.

Embodiment P50

The method of embodiment P49, wherein $R^{1A}$ is substituted or unsubstituted $C_1$-$C_{10}$ thiol-alkyl.

Embodiment P51

The method of embodiment P50, wherein $R^{1A}$ is unsubstituted $C_1$-$C_{10}$ thiol-alkyl.

Embodiment P52

The method of embodiment P51, wherein $R^{1A}$ is thioethyl.

Embodiment P53

The method of embodiment P5, wherein $R^1$ is —$OR^{1A}$; $R^2$, $R^3$, and $R^4$ are —OH; $R^5$ is —SAc; and $R^{5'}$ is H.

Embodiment P54

The method of embodiment P53, wherein $R^{1A}$ is methyl.

Embodiment P55

The method of embodiment P5, wherein $R^1$ is —$OR^{1A}$ or —$R^{1D}$, $R^2$ is —OH or —$NR^{2B}$; $R^{2B}$ is —$C(O)R^{2C}$; $R^{2C}$ is substituted or unsubstituted $C_1$-$C_{10}$ alkyl; $R^3$ and $R^4$ are —OH; and $R^5$ is —$OR^{5A}$ or —$R^{5D}$.

Embodiment P56

The method of embodiment P55, wherein $R^1$ is —$OR^{1A}$.

Embodiment P57

The method of embodiment P56, wherein $R^{1A}$ is unsubstituted $C_1$-$C_5$ alkyl.

Embodiment P8

The method of embodiment P57, wherein $R^{1A}$ is methyl.

Embodiment P59

The method of embodiment P55, wherein $R^1$ is —$R^{1D}$.

Embodiment P60

The method of embodiment P55, wherein $R^5$ is —$OR^{5A}$; $R^{5A}$ is substituted or unsubstituted $C_1$-$C_{10}$ thiol-alkyl or substituted or unsubstituted 2 to 10 membered thiol-heteroalkyl; and $R^{5'}$ is H.

Embodiment P61

The method of embodiment P55, wherein $R^5$ is —$R^{5D}$; and $R^{5'}$ is —OH.

Embodiment P62

The method of embodiment P55, wherein $R^5$ is —$R^{5D}$; and $R^{5'}$ is H.

Embodiment P3

The method of one of embodiments P55 to P62, wherein $R^2$ is —OH.

Embodiment 64

The method of one of embodiments P55 to P62, wherein $R^2$ is —$NR^{2B}$.

Embodiment P65

The method of embodiment P64, wherein $R^2$ is —NHAc.

Embodiment P66

The method of embodiment P1, wherein said thiosaccharide mucolytic agent has the formula:

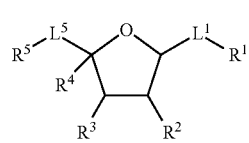

(II)

wherein, $L^1$ and $L^5$ are independently a bond or methylene; $R^1$ is —SH, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$—SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ thiol-alkyl or substituted or unsubstituted 2 to 10 membered thiol-heteroalkyl; $R^3$—SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^4$—SH, —$OR^{4A}$ or —$NR^{4B}$ wherein $R^{4A}$ is H, substituted or unsubstituted $C_1$-$C_{10}$ thiol-alkyl or substituted or unsubstituted 2 to 10 membered thiol-heteroalkyl; $R^{4B}$ is —$C(O)R^{4C}$, substituted or unsubstituted $C_1$-$C_{10}$ thiol-alkyl or substituted or unsubstituted 2 to 10 membered thiol-heteroalkyl; and $R^{4C}$ is substituted or unsubstituted $C_1$-$C_{10}$ thiol-alkyl or substituted or unsubstituted 2 to 10 membered thiol-heteroalkyl; and $R^5$ is H, —SH, —$OR^{5A}$ or —$NR^{5B}$ wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —$C(O)R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl.

Embodiment P67

The method of embodiment P1, wherein said thiosaccharide mucolytic agent has the formula:

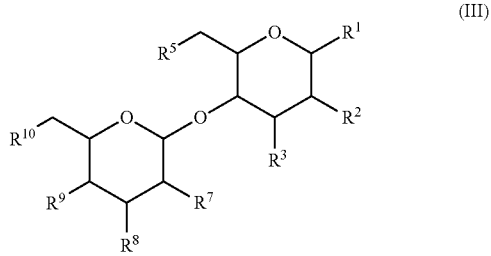

(III)

wherein, $R^1$ is —SH, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$ is —SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —$OR^{5A}$ or —$NR^{5B}$ wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —$C(O)R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ is —SH, —$OR^{7A}$ or —$NR^{7B}$, wherein $R^{7A}$ is H, substituted or unsubstituted $C_1$-$C_{10}$ thiol-alkyl or substituted or unsubstituted 2 to 10 membered thiol-heteroalkyl; $R^{7B}$ is —$C(O)R^{7C}$, substituted or unsubstituted $C_1$-$C_{10}$ thiol-alkyl or substituted or unsubstituted 2 to 10 membered thiol-heteroalkyl; and $R^{7C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^8$ is —SH, —$OR^{7A}$ or —$NR^{7B}$, wherein $R^{8A}$ is H, substituted or unsubstituted $C_1$-$C_{10}$ thiol-alkyl or substituted or unsubstituted 2 to 10 membered thiol-heteroalkyl; $R^{8B}$ is —$C(O)R^{8C}$, substituted or unsubstituted $C_1$-$C_{10}$ thiol-alkyl or substituted or unsubstituted 2 to 10 membered thiol-heteroalkyl; and $R^{8C}$ is substituted or unsubstituted $C_1$-$C_{10}$ thiol-alkyl or substituted or unsubstituted 2 to 10 membered thiol-heteroalkyl; $R^9$ is —SH, —$OR^{9A}$ or —$NR^{9B}$, wherein $R^{9A}$ is H, substituted or unsubstituted $C_1$-$C_{10}$ thiol-alkyl or substituted or unsubstituted 2 to 10 membered thiol-heteroalkyl; $R^{9B}$ is —$C(O)R^9C$, substituted or unsubstituted $C_1$-$C_{10}$ thiol-alkyl or substituted or unsubstituted 2 to 10 membered thiol-heteroalkyl; and $R^{9C}$ is substituted or unsubstituted $C_1$-$C_{10}$ thiol-alkyl or substituted or unsubstituted 2 to 10 membered thiol-heteroalkyl; $R^{10}$ is H, —SH, —SAc, —$OR^{9A}$ or —$NR^{9B}$, wherein $R^{10A}$ is H, substituted or unsubstituted $C_1$-$C_{10}$ thiol-alkyl or substituted or unsubstituted 2 to 10 membered thiol-heteroalkyl; $R^{10B}$ is —$C(O)R^{10C}$, substituted or unsubstituted $C_1$-$C_{10}$ thiol-alkyl or substituted or unsubstituted 2 to 10 membered thiol-heteroalkyl; and $R^{10C}$ is substituted or unsubstituted $C_1$-$C_{10}$ thiol-alkyl or substituted or unsubstituted 2 to 10 membered thiol-heteroalkyl.

Embodiment P68

The method of embodiment P67, wherein $R^1$ is —$OR^{1A}$; and $R^2$, $R^3$, $R^5$, $R^7$, $R^8$, and $R^9$ are —OH; and $R^{10}$ is —SH or —$OR^{10A}$.

Embodiment P69

The method of embodiment P68, wherein $R^{1A}$ is substituted or unsubstituted $C_1$-$C_{10}$ thiol-alkyl or substituted or unsubstituted 2 to 10 membered thiol-heteroalkyl.

Embodiment P70

The method of embodiment P69, wherein $R^{1A}$ is unsubstituted $C_1$-$C_{10}$ thiol-alkyl; and $R^{10}$ is —OH.

Embodiment P71

The method of embodiment P70, wherein $R^{1A}$ is thioethyl.

Embodiment P72

The method of embodiment P68, wherein $R^{1A}$ is H; and $R^{10}$ is —SH.

Embodiment P73

The method of embodiment P67, wherein $R^{1A}$ is substituted or unsubstituted $C_1$-$C_{10}$ thiol-alkyl or substituted or unsubstituted 2 to 10 membered thiol-heteroalkyl; $R^2$, $R^3$, $R^5$, $R^7$, $R^8$, and $R^9$ are —OH; and $R^{10}$ is —SH.

Embodiment P74

The method of embodiment P73, wherein $R^{1A}$ is unsubstituted $C_1$-$C_{10}$ thiol-alkyl.

Embodiment P75

The method of embodiment P74, wherein $R^{1A}$ is thioethyl.

Embodiment P76

The method of embodiment P67, wherein $R^1$, $R^3$, $R^5$, $R^8$, $R^9$, and $R^{10}$ are —OH; $R^2$ is —OH or —$NR^{2B}$; $R^{2C}$ is substituted or unsubstituted $C_1$-$C_{10}$ thiol-alkyl; $R^7$ is —OH or —$NR^{7B}$; and $R^{7C}$ is substituted or unsubstituted $C_1$-$C_{10}$ thiol-alkyl.

Embodiment P77

The method of embodiment P67, wherein $R^1$ is —$OR^{1A}$; $R^{1A}$ is substituted or unsubstituted $C_1$-$C_{10}$ thiol-alkyl or substituted or unsubstituted 2 to 10 membered thiol-heteroalkyl; $R^3$, $R^5$, $R^8$, $R^9$, and $R^{10}$ are —OH; $R^2$ is —OH or —$NR^{2B}$; $R^{2C}$ is substituted or unsubstituted $C_1$-$C_{10}$ alkyl; $R^7$ is —OH or —$NR^{7B}$; and $R^{7C}$ is substituted or unsubstituted $C_1$-$C_{10}$ alkyl.

Embodiment P78

The method of embodiment P77, wherein $R^2$ is —NHAc; and $R^7$ is —NHAc.

Embodiment P79

The method of embodiment P1, wherein said thiosaccharide mucolytic agent has the formula:

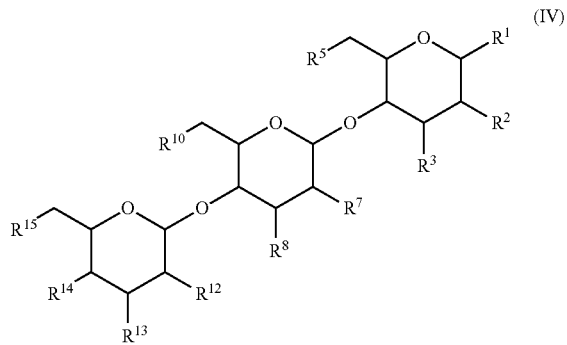

(IV)

wherein, $R^1$ is —SH, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —C(O)$R^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —C(O)$R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$ is —SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —C(O)$R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —$OR^{5A}$ or —$NR^{5B}$, wherein $R^{5A}$ is H, substituted or unsubstituted $C_1$-$C_{10}$ thiol-alkyl or substituted or unsubstituted 2 to 10 membered thiol-heteroalkyl, $R^{5B}$ is —C(O)$R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ is —SH, —$OR^{7A}$ or —$NR^{7B}$, wherein $R^{7A}$ is H, substituted or unsubstituted $C_1$-$C_{10}$ thiol-alkyl or substituted or unsubstituted 2 to 10 membered thiol-heteroalkyl; $R^{7B}$ is —C(O)$R^{7C}$, substituted or unsubstituted $C_1$-$C_{10}$ thiol-alkyl or substituted or unsubstituted 2 to 10 membered thiol-heteroalkyl; and $R^{7C}$ is substituted or unsubstituted $C_1$-$C_{10}$ thiol-alkyl or substituted or unsubstituted 2 to 10 membered thiol-heteroalkyl; $R^8$ is —SH, —$OR^{8A}$ or —$NR^{8B}$, wherein $R^{8A}$ is H, substituted or unsubstituted $C_1$-$C_{10}$ thiol-alkyl or substituted or unsubstituted 2 to 10 membered thiol-heteroalkyl; $R^{8B}$ is —C(O)$R^{8C}$, substituted or unsubstituted $C_1$-$C_{10}$ thiol-alkyl or substituted or unsubstituted 2 to 10 membered thiol-heteroalkyl; and $R^{8C}$ is substituted or unsubstituted $C_1$-$C_{10}$ thiol-alkyl or substituted or unsubstituted 2 to 10 membered thiol-heteroalkyl; $R^{10}$ is H, —SH, —SAc, —$OR^{10A}$ or —$NR^{10B}$, wherein $R^{10A}$ is H, substituted or unsubstituted $C_1$-$C_{10}$ thiol-alkyl or substituted or unsubstituted 2 to 10 membered thiol-heteroalkyl; $R^{10B}$ is —C(O)$R^{10C}$, substituted or unsubstituted $C_1$-$C_{10}$ thiol-alkyl or substituted or unsubstituted 2 to 10 membered thiol-heteroalkyl; and $R^{10C}$ is substituted or unsubstituted $C_1$-$C_{10}$ thiol-alkyl or substituted or unsubstituted 2 to 10 membered thiol-heteroalkyl; $R^{12}$—SH, —$OR^{12A}$ or —$NR^{12B}$, wherein $R^{12A}$ is H, substituted or unsubstituted $C_1$-$C_{10}$ thiol-alkyl or substituted or unsubstituted 2 to 10 membered thiol-heteroalkyl; $R^{2B}$ is —C(O)$R^{12C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ thiol-alkyl or substituted or unsubstituted 2 to 10 membered thiol-heteroalkyl; $R^{13}$—SH, —$OR^{13A}$ or —$NR^{3B}$ wherein $R^{13A}$ is H, substituted or unsubstituted $C_1$-$C_{10}$ thiol-alkyl or substituted or unsubstituted 2 to 10 membered thiol-heteroalkyl; $R^{13B}$ is —C(O)$R^{13C}$, substituted or unsubstituted $C_1$-$C_{10}$ thiol-alkyl or substituted or unsubstituted 2 to 10 membered thiol-heteroalkyl; and $R^{13C}$ is substituted or unsubstituted $C_1$-$C_{10}$ thiol-alkyl or substituted or unsubstituted 2 to 10 membered thiol-heteroalkyl; $R^{14}$ is —SH, —$OR^{14A}$ or —$NR^{14B}$, wherein $R^{14A}$ is H, substituted or unsubstituted $C_1$-$C_{10}$ thiol-alkyl or substituted or unsubstituted 2 to 10 membered thiol-heteroalkyl; $R^{14B}$ is —C(O)$R^{14C}$, substituted or unsubstituted $C_1$-$C_{10}$ thiol-alkyl or substituted or unsubstituted 2 to 10 membered thiol-heteroalkyl; and $R^{14C}$ is substituted or unsubstituted $C_1$-$C_{10}$ thiol-alkyl or substituted or unsubstituted 2 to 10 membered thiol-heteroalkyl; and $R^{15}$ is H, —SH, —SAc, —$OR^{15A}$ or —$NR^{15B}$, wherein $R^{15A}$ is H, substituted or unsubstituted $C_1$-$C_{10}$ thiol-alkyl or substituted or unsubstituted 2 to 10 membered thiol-heteroalkyl; $R^{15B}$ is —C(O)$R^{15C}$, substituted or unsubstituted $C_1$-$C_{10}$ thiol-alkyl or substituted or unsubstituted 2 to 10 membered thiol-heteroalkyl; and $R^{15C}$ is substituted or unsubstituted $C_1$-$C_{10}$ thiol-alkyl or substituted or unsubstituted 2 to 10 membered thiol-heteroalkyl.

Embodiment P80

The method of embodiment P79, wherein $R^1$, $R^3$, $R^5$, $R^8$, $R^{10}$, $R^{13}$, $R^{14}$ and $R^{15}$ are —OH; $R^2$ is —OH or —$NR^{2B}$; $R^{2B}$ is —$C(O)R^{2C}$; $R^{2C}$ is substituted or unsubstituted $C_1$-$C_{10}$ thiol-alkyl or substituted or unsubstituted 2 to 10 membered thiol-heteroalkyl; $R^7$ is —OH or —$NH^{7B}$; $R^{7B}$ is —$C(O)R^{7C}$; $R^{7C}$ is substituted or unsubstituted $C_1$-$C_{10}$ thiol-alkyl or substituted or unsubstituted 2 to 10 membered thiol-heteroalkyl; $R^{12}$ is —OH or —$NH^{12B}$; $R12^B$ is —$C(O)R12^C$; and $R12^C$ is substituted or unsubstituted $C_1$-$C_{10}$ thiol-alkyl or substituted or unsubstituted 2 to 10 membered thiol-heteroalkyl.

Embodiment P81

The method of embodiment PP1, wherein said thiosaccharide mucolytic agent has the formula:

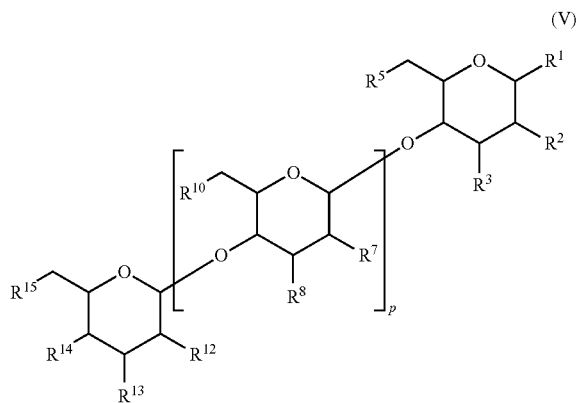

(V)

wherein, $R^1$ is —SH, —$OR^{1A}$ or —$NR^{1B}$, wherein $R^{1A}$ is H, substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^3$ is —SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —$OR^{5A}$ or —$NR^{5B}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —$C(O)R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ at each occurrence is independently —SH, —$OR^{7A}$ or —$NR^{7B}$, wherein $R^{7A}$ at each occurrence is independently H, substituted or unsubstituted $C_1$-$C_{10}$ thiol-alkyl or substituted or unsubstituted 2 to 10 membered thiol-heteroalkyl; $R^{7B}$ at each occurrence is independently —$C(O)R^{7C}$, substituted or unsubstituted $C_1$-$C_{10}$ thiol-alkyl or substituted or unsubstituted 2 to 10 membered thiol-heteroalkyl; and $R^{7C}$ at each occurrence is independently substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^8$ at each occurrence is independently —SH, —$OR^{8A}$ or —$NR^{8B}$, wherein $R^{8A}$ at each occurrence is independently H, substituted or unsubstituted $C_1$-$C_{10}$ thiol-alkyl or substituted or unsubstituted 2 to 10 membered thiol-heteroalkyl; $R^{8B}$ at each occurrence is independently —$C(O)R^{8C}$, substituted or unsubstituted $C_1$-$C_{10}$ thiol-alkyl or substituted or unsubstituted 2 to 10 membered thiol-heteroalkyl; and $R^{8C}$ at each occurrence is independently substituted or unsubstituted $C_1$-$C_{10}$ thiol-alkyl or substituted or unsubstituted 2 to 10 membered thiol-heteroalkyl; $R^{10}$ at each occurrence is independently H, —SH, —SAc, —$OR^{10A}$ or —$NR^{10B}$, wherein $R^{10A}$ at each occurrence is independently H, substituted or unsubstituted $C_1$-$C_{10}$ thiol-alkyl or substituted or unsubstituted 2 to 10 membered thiol-heteroalkyl; $R^{10B}$ at each occurrence is independently —$C(O)R^{10C}$, substituted or unsubstituted $C_1$-$C_{10}$ thiol-alkyl or substituted or unsubstituted 2 to 10 membered thiol-heteroalkyl; and $R^{10C}$ at each occurrence is independently substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^{12}$ is —SH, —$OR^{2A}$ or —$NR^{2B}$, wherein $R^{12A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ thiol-alkyl or substituted or unsubstituted 2 to 10 membered thiol-heteroalkyl; $R^{13}$ is —SH, —$OR^{13A}$ or —$NR^{13B}$, wherein $R^{13A}$ is H, substituted or unsubstituted $C_1$-$C_{10}$ thiol-alkyl or substituted or unsubstituted 2 to 10 membered thiol-heteroalkyl; $R^{13B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^{14}$ is —SH, —$OR^{14A}$ or —$NR^{14B}$, wherein $R^{14A}$ is H, substituted or unsubstituted $C_1$-$C_{10}$ thiol-alkyl or substituted or unsubstituted 2 to 10 membered thiol-heteroalkyl; $R^{4B}$ is —$C(O)R^{4C}$, substituted or unsubstituted $C_1$-$C_{10}$ thiol-alkyl or substituted or unsubstituted 2 to 10 membered thiol-heteroalkyl; and $R^{4C}$ is substituted or unsubstituted $C_1$-$C_{10}$ thiol-alkyl or substituted or unsubstituted 2 to 10 membered thiol-heteroalkyl; and $R^{15}$ is H, —SH, —SAc, —$OR^{15A}$ or —$NR^{15B}$, wherein $R^{15A}$ is H, substituted or unsubstituted $C_1$-$C_{10}$ thiol-alkyl or substituted or unsubstituted 2 to 10 membered thiol-heteroalkyl; $R^{15B}$ is —$C(O)R^{5C}$, substituted or unsubstituted $C_1$-$C_{10}$ thiol-alkyl or substituted or unsubstituted 2 to 10 membered thiol-heteroalkyl; and $R^{15C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; and p is 2-10.

Embodiment P82

A compound with structure of Formula (I):

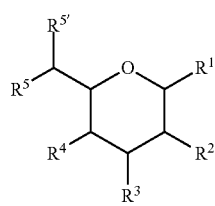

(I)

wherein, $R^1$ is —SH, —$OR^{1A}$, —$NR^{1B}$ or —$R^{1D}$, wherein $R^{1A}$ is H, substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; $R^{1C}$ is substituted or unsubstituted $C_1$-$C_{10}$ thiol-alkyl or substituted or unsubstituted 2 to 10 membered thiol-heteroalkyl; and $R^{1D}$ is substituted or unsubstituted $C_1$-$C_{10}$ thiol-alkyl or substituted or unsubstituted 2 to 10 membered thiol-heteroalkyl; $R^2$ is —SH, —$OR^{2A}$ or $NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$—SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^4$ is —SH, —SAc, —$OR^{4A}$ or —$NR^{4B}$, wherein $R^{4A}$ is H, substituted or unsubstituted $C_1$-$C_{10}$ thiol-alkyl or substituted or unsubstituted 2 to 10 membered thiol-heteroalkyl; $R^{4B}$ is —$C(O)R^{4C}$, substituted or unsubstituted $C_1$-$C_{10}$ thiol-alkyl or substituted or unsubstituted 2 to 10 membered thiol-heteroalkyl; and $R^{4C}$ is substituted or unsubstituted $C_1$-$C_{10}$ thiol-alkyl or substituted or unsubstituted 2 to 10 membered thiol-heteroalkyl; and $R^5$ is H, —SH, —SAc, —$OR^{5A}$, —$NR^{5B}$, or —$R^{5D}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —$C(O)R^{5C}$, substituted or unsubstituted $C_1$-$C_{10}$ thiol-alkyl or substituted or unsubstituted 2 to 10 membered thiol-heteroalkyl; $R^{5C}$ is substituted or unsubstituted $C_1$-$C_{10}$ thiol-alkyl or substituted or unsubstituted 2 to 10 membered thiol-heteroalkyl; and $R^{5D}$ is substituted or unsubstituted $C_1$-$C_{10}$ thiol-alkyl; and $R^{5'}$ is H or —OH; provided, however, that said structure is not

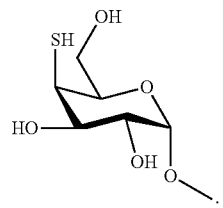

Embodiment P83

The compound of embodiment P82, having the structure

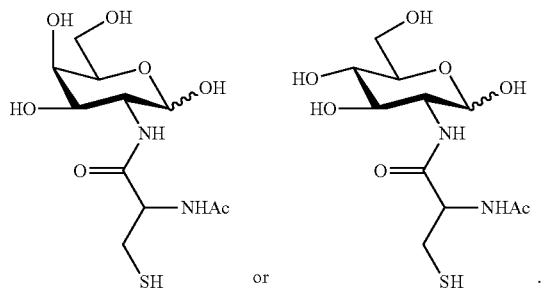

Embodiment P84

The compound of embodiment P82, having the structure

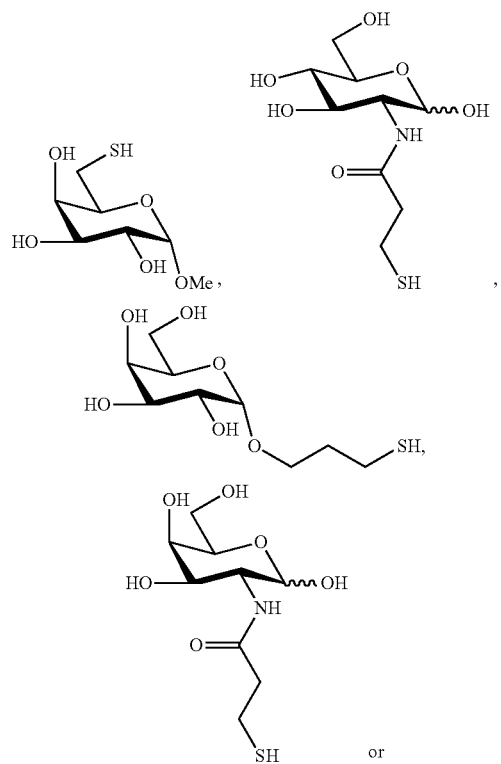

-continued

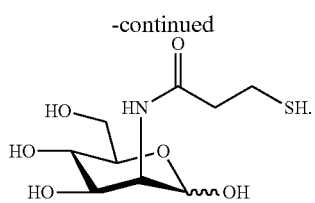

Embodiment P85

The compound of embodiment P82, having the structure

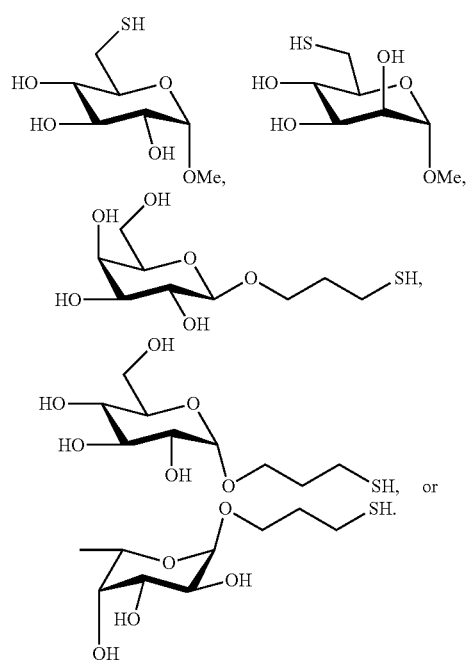

Embodiment P86

The compound of embodiment P82, having the structure

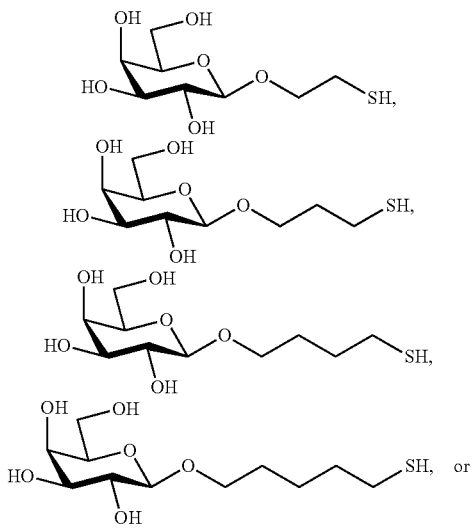

-continued

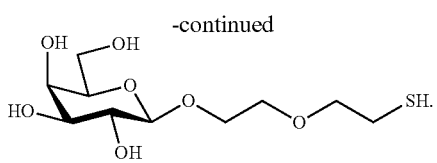

Embodiment P87

The compound of embodiment P82, having the structure

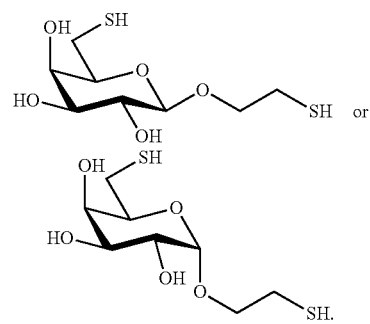

Embodiment P88

The compound of embodiment P82, having the structure

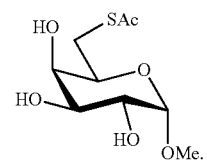

Embodiment P89

A compound with structure of Formula (III):

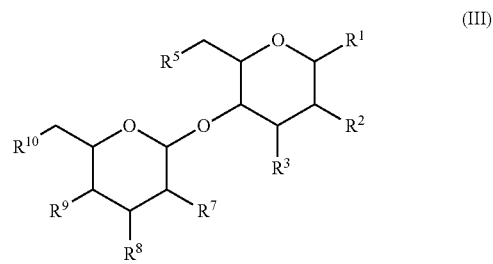

wherein, $R^1$ is —SH, —OR$^{1A}$ or —NR$^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —C(O)R$^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —OR$^{2A}$ or —NR$^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —C(O)$R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$ is —SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —C(O)$R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —$OR^{5A}$ or —$NR^{5B}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —C(O)$R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ is —SH, —$OR^{7A}$ or —$NR^{7B}$, wherein $R^{7A}$ is H, substituted or unsubstituted $C_1$-$C_{10}$ thiol-alkyl or substituted or unsubstituted 2 to 10 membered thiol-heteroalkyl; $R^{7B}$ is —C(O)$R^{7C}$, substituted or unsubstituted $C_1$-$C_{10}$ thiol-alkyl or substituted or unsubstituted 2 to 10 membered thiol-heteroalkyl; and $R^{7C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^8$ is —SH, —$OR^{8A}$ or —$NR^{8B}$, wherein $R^{8A}$ is H, substituted or unsubstituted $C_1$-$C_{10}$ thiol-alkyl or substituted or unsubstituted 2 to 10 membered thiol-heteroalkyl; $R^{8B}$ is —C(O)$R^{8C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^9$ is —SH, —$OR^{9A}$ or —$NR^{9B}$, wherein $R^{9A}$ is H, substituted or unsubstituted $C_1$-$C_{10}$ thiol-alkyl or substituted or unsubstituted 2 to 10 membered thiol-heteroalkyl; $R^{9B}$ is —C(O)$R^{9C}$, substituted or unsubstituted $C_1$-$C_{10}$ thiol-alkyl or substituted or unsubstituted 2 to 10 membered thiol-heteroalkyl; and $R^{9C}$ is substituted or unsubstituted $C_1$-$C_{10}$ thiol-alkyl or substituted or unsubstituted 2 to 10 membered thiol-heteroalkyl; and $R^{10}$ is H, —SH, —SAc, —$OR^{10A}$ or —$NR^{10B}$, wherein $R^{10A}$ is H, substituted or unsubstituted $C_1$-$C_{10}$ thiol-alkyl or substituted or unsubstituted 2 to 10 membered thiol-heteroalkyl; $R^{10B}$ is —C(O)$R^{10C}$, substituted or unsubstituted $C_1$-$C_{10}$ thiol-alkyl or substituted or unsubstituted 2 to 10 membered thiol-heteroalkyl; and $R^{10C}$ is substituted or unsubstituted $C_1$-$C_{10}$ thiol-alkyl or substituted or unsubstituted 2 to 10 membered thiol-heteroalkyl.

Embodiment P90

The compound of embodiment P89, having the structure

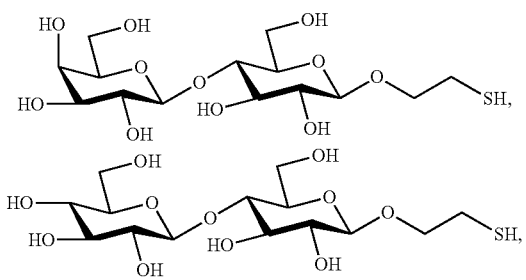

Embodiment P91

The compound of embodiment P89, having the structure

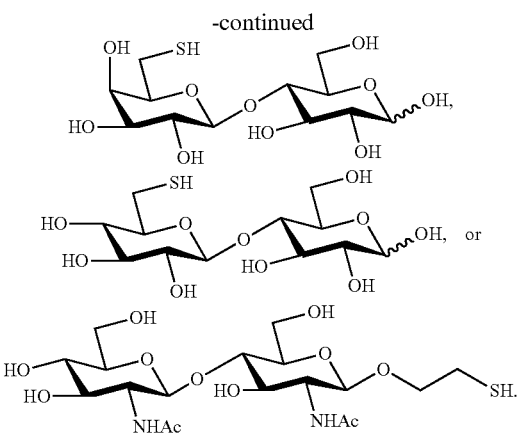

Embodiment P92

A compound with structure of Formula (IV):

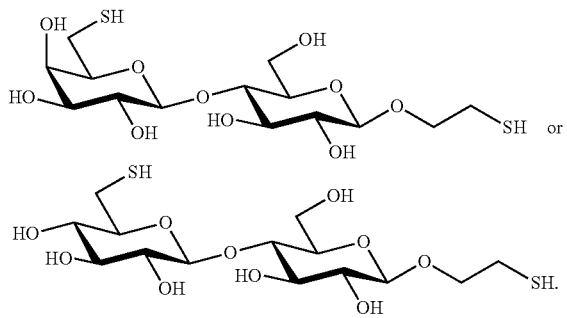

wherein, $R^L$ is —SH, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —C(O)$R^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —C(O)$R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$ is —SH, —OR$^{3A}$ or —NR$^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —C(O)$R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —OR$^{5A}$ or —NR$^{5B}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —C(O)$R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ is —SH, —OR$^{7A}$ or —NR$^{7B}$, wherein $R^{7A}$ is H, substituted or unsubstituted $C_1$-$C_{10}$ thiol-alkyl or substituted or unsubstituted 2 to 10 membered thiol-heteroalkyl; $R^{7B}$ is —C(O)$R^{7C}$, substituted or unsubstituted $C_1$-$C_{10}$ thiol-alkyl or substituted or unsubstituted 2 to 10 membered thiol-heteroalkyl; and $R^{7C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^8$ is —SH, —OR$^{8A}$ or —NR$^{8B}$, wherein $R^{8A}$ is H, substituted or unsubstituted $C_1$-$C_{10}$ thiol-alkyl or substituted or unsubstituted 2 to 10 membered thiol-heteroalkyl; $R^{8B}$ is —C(O)$R^{8C}$, substituted or unsubstituted $C_1$-$C_{10}$ thiol-alkyl or substituted or unsubstituted 2 to 10 membered thiol-heteroalkyl; and $R^{8C}$ is substituted or unsubstituted $C_1$-$C_{10}$ thiol-alkyl or substituted or unsubstituted 2 to 10 membered thiol-heteroalkyl; $R^{10}$ is H, —SH, —SAc, —OR$^{10A}$ or —NR$^{10B}$, wherein $R^{10A}$ is H, substituted or unsubstituted $C_1$-$C_{10}$ thiol-alkyl or substituted or unsubstituted 2 to 10 membered thiol-heteroalkyl; $R^{10B}$ is —C(O)$R^{10C}$, substituted or unsubstituted $C_1$-$C_{10}$ thiol-alkyl or substituted or unsubstituted 2 to 10 membered thiol-heteroalkyl; and Roc is substituted or unsubstituted $C_1$-$C_{10}$ thiol-alkyl or substituted or unsubstituted 2 to 10 membered thiol-heteroalkyl; $R^{12}$ is —SH, —OR$^{12A}$ or —NR$^{12B}$, wherein $R^{12A}$ is H, substituted or unsubstituted $C_1$-$C_{10}$ thiol-alkyl or substituted or unsubstituted 2 to 10 membered thiol-heteroalkyl; $R^{12B}$ is —C(O)$R^{12C}$ substituted or unsubstituted $C_1$-$C_{10}$ thiol-alkyl or substituted or unsubstituted 2 to 10 membered thiol-heteroalkyl; and $R^{12C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^{13}$ is —SH, —OR$^{13A}$ or —NR$^{3B}$, wherein $R^{13A}$ is H, substituted or unsubstituted $C_1$-$C_{10}$ thiol-alkyl or substituted or unsubstituted 2 to 10 membered thiol-heteroalkyl; $R^{13B}$ is —C(O)$R^{13C}$, substituted or unsubstituted $C_1$-$C_{10}$ thiol-alkyl or substituted or unsubstituted 2 to 10 membered thiol-heteroalkyl; and $R^{13C}$ is substituted or unsubstituted $C_1$-$C_{10}$ thiol-alkyl or substituted or unsubstituted 2 to 10 membered thiol-heteroalkyl; $R^{14}$ is —SH, —OR$^{14A}$ or —NR$^{14B}$, wherein $R^{14A}$ is H, substituted or unsubstituted $C_1$-$C_{10}$ thiol-alkyl or substituted or unsubstituted 2 to 10 membered thiol-heteroalkyl; $R^{14B}$ is —C(O)$R^{14C}$, substituted or unsubstituted $C_1$-$C_{10}$ thiol-alkyl or substituted or unsubstituted 2 to 10 membered thiol-heteroalkyl; and $R^{14C}$ is substituted or unsubstituted $C_1$-$C_{10}$ thiol-alkyl or substituted or unsubstituted 2 to 10 membered thiol-heteroalkyl; and $R^{15}$ is H, —SH, —SAc, —OR$^{15A}$ or —NR$^{15B}$, wherein $R^{15A}$ is H, substituted or unsubstituted $C_1$-$C_{10}$ thiol-alkyl or substituted or unsubstituted 2 to 10 membered thiol-heteroalkyl; $R^{15B}$ is —C(O)$R^{5C}$, substituted or unsubstituted $C_1$-$C_{10}$ thiol-alkyl or substituted or unsubstituted 2 to 10 membered thiol-heteroalkyl; and $R^{15C}$ is substituted or unsubstituted $C_1$-$C_{10}$ thiol-alkyl or substituted or unsubstituted 2 to 10 membered thiol-heteroalkyl.

Embodiment P93

A compound with structure of Formula (V):

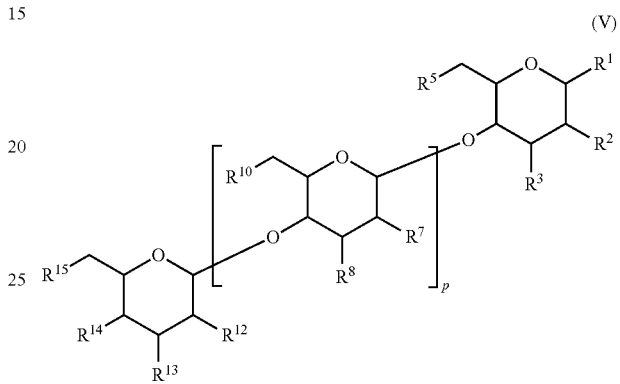

wherein, $R^1$ is —SH, —OR$^{1A}$ or —NR$^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —C(O)$R^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —OR$^{2A}$ or —NR$^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —C(O)$R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$ is —SH, —OR$^{3A}$ or —NR$^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —C(O)$R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —OR$^{5A}$ or —NR$^{5B}$ wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —C(O)$R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ is at each occurrence is independently —SH, —OR$^{7A}$ or —NR$^{7B}$, wherein $R^{7A}$ is H, substituted or unsubstituted $C_1$-$C_{10}$ thiol-alkyl or substituted or unsubstituted 2 to 10 membered thiol-heteroalkyl; $R^{7B}$ is —C(O)$R^{7C}$, substituted or unsubstituted $C_1$-$C_{10}$ thiol-alkyl or substituted or unsubstituted 2 to 10 membered thiol-heteroalkyl; and $R^{7C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^8$ at each occurrence is independently-SH, —$OR^{8A}$ or —$NR^{8B}$, wherein $R^{8A}$ is H, substituted or unsubstituted $C_1$-$C_{10}$ thiol-alkyl or substituted or unsubstituted 2 to 10 membered thiol-heteroalkyl; $R^{8B}$ is —$C(O)R^{8C}$, substituted or unsubstituted $C_1$-$C_{10}$ thiol-alkyl or substituted or unsubstituted 2 to 10 membered thiol-heteroalkyl; and $R^{8C}$ is substituted or unsubstituted $C_1$-$C_{10}$ thiol-alkyl or substituted or unsubstituted 2 to 10 membered thiol-heteroalkyl; $R^{10}$ at each occurrence is independently H, —SH, —SAc, —$OR^{10A}$ or —$NR^{10B}$, wherein $R^{10A}$ is H, substituted or unsubstituted $C_1$-$C_{10}$ thiol-alkyl or substituted or unsubstituted 2 to 10 membered thiol-heteroalkyl; $R^{10B}$ is —$C(O)Roc$, substituted or unsubstituted $C_1$-$C_{10}$ thiol-alkyl or substituted or unsubstituted 2 to 10 membered thiol-heteroalkyl; and $R^{10C}$ is substituted or unsubstituted $C_1$-$C_{10}$ thiol-alkyl or substituted or unsubstituted 2 to 10 membered thiol-heteroalkyl; $R^{12}$ is —SH, —$OR^{12A}$ or —$NR^{12B}$, wherein $R^{12A}$ is H, substituted or unsubstituted $C_1$-$C_{10}$ thiol-alkyl or substituted or unsubstituted 2 to 10 membered thiol-heteroalkyl; $R^{12B}$ is —$C(O)R^{12C}$ substituted or unsubstituted $C_1$-$C_{10}$ thiol-alkyl or substituted or unsubstituted 2 to 10 membered thiol-heteroalkyl; and $R^{12C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^{13}$ is —SH, —$OR^{13A}$ or —$NR^{3B}$, wherein $R^{13A}$ is H, substituted or unsubstituted $C_1$-$C_{10}$ thiol-alkyl or substituted or unsubstituted 2 to 10 membered thiol-heteroalkyl; $R^{13B}$ is —$C(O)R^{13C}$, substituted or unsubstituted $C_1$-$C_{10}$ thiol-alkyl or substituted or unsubstituted 2 to 10 membered thiol-heteroalkyl; and $R^{13C}$ is substituted or unsubstituted $C_1$-$C_{10}$ thiol-alkyl or substituted or unsubstituted 2 to 10 membered thiol-heteroalkyl; $R^{14}$ is —SH, —$OR^{14A}$ or —$NR^{14B}$, wherein $R^{14A}$ is H, substituted or unsubstituted $C_1$-$C_{10}$ thiol-alkyl or substituted or unsubstituted 2 to 10 membered thiol-heteroalkyl; $R^{14B}$ is —$C(O)R^{14C}$, substituted or unsubstituted $C_1$-$C_{10}$ thiol-alkyl or substituted or unsubstituted 2 to 10 membered thiol-heteroalkyl; and $R^{14C}$ is substituted or unsubstituted $C_1$-$C_{10}$ thiol-alkyl or substituted or unsubstituted 2 to 10 membered thiol-heteroalkyl; and $R^{15}$ is H, —SH, —SAc, —$OR^{15A}$ or —$NR^{15B}$, wherein $R^{15A}$ is H, substituted or unsubstituted $C_1$-$C_{10}$ thiol-alkyl or substituted or unsubstituted 2 to 10 membered thiol-heteroalkyl; $R^{15B}$ is —$C(O)R^5$, substituted or unsubstituted $C_1$-$C_{10}$ thiol-alkyl or substituted or unsubstituted 2 to 10 membered thiol-heteroalkyl; and $R^5$ is substituted or unsubstituted $C_1$-$C_{10}$ thiol-alkyl or substituted or unsubstituted 2 to 10 membered thiol-heteroalkyl; and p is 2-10.

Further embodiments are provided following.

Embodiment 1

Use of a thiosaccharide mucolytic agent for decreasing mucus elasticity or decreasing mucus viscosity in a subject in need thereof.

Embodiment 2

The use of embodiment 1, wherein said method includes decreasing mucus viscoelasticity in said subject.

Embodiment 3

The use of embodiment 1, wherein said thiosaccharide mucolytic agent is a thiol monosaccharide mucolytic agent, a thiol disaccharide mucolytic agent, or a thiol trisaccharide mucolytic agent.

Embodiment 4

The use of embodiment 1, wherein said thiosaccharide mucolytic agent includes D-glucopyranose, D-galactopyranose, D-mannopyranose, D-glucopyranoside, D-galactopyranoside, or D-mannopyranoside moieties.

Embodiment 5

The use of embodiment 1, wherein said thiosaccharide mucolytic agent includes D-galactopyranose.

Embodiment 6

The use of embodiment 1, wherein said thiosaccharide mucolytic agent has the formula:

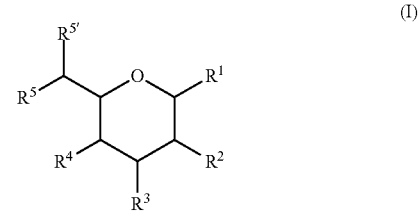

(I)

wherein, $R^1$ is —SH, —$OR^{1A}$, —$NR^{1B}$ or —$R^{1D}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; $R^{1C}$ is substituted or unsubstituted $C_1$-$C_{10}$ thiol-alkyl or substituted or unsubstituted 2 to 10 membered thiol-heteroalkyl; and $R^{1D}$ is substituted or unsubstituted $C_1$-$C_{10}$ thiol-alkyl or substituted or unsubstituted 2 to 10 membered thiol-heteroalkyl; $R^2$—SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$—SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^4$ is —SH, —SAc, —$OR^{4A}$ or —$NR^{4B}$, wherein $R^{4A}$ is H, substituted or unsubstituted $C_1$-$C_{10}$ thiol-alkyl or substituted or unsubstituted 2 to 10 membered thiol-heteroalkyl; $R^{4B}$ is —$C(O)R^{4C}$ substituted or unsubstituted $C_1$-$C_{10}$ thiol-alkyl or substituted or unsubstituted 2 to 10 membered thiol-heteroalkyl; and $R^{4C}$ is substituted or unsubstituted $C_1$-$C_{10}$ thiol-alkyl or substituted or unsubstituted 2 to 10 membered thiol-heteroalkyl; and $R^5$ is H, —SH, —SAc, —OR$^{5A}$, —NR$^{5B}$, or —R$^{5D}$, wherein R$^{5A}$ is H, substituted or unsubstituted $C_1$-$C_{10}$ thiol-alkyl or substituted or unsubstituted 2 to 10 membered thiol-heteroalkyl; R$^{5B}$ is —C(O)R$^{5C}$, substituted or unsubstituted $C_1$-$C_{10}$ thiol-alkyl or substituted or unsubstituted 2 to 10 membered thiol-heteroalkyl; R$^{5C}$ is substituted or unsubstituted $C_1$-$C_{10}$ thiol-alkyl or substituted or unsubstituted 2 to 10 membered thiol-heteroalkyl; and R$^{5D}$ is substituted or unsubstituted $C_1$-$C_{10}$ thiol-alkyl; and R$^{5'}$ is H or —OH.

Embodiment 7

The use of embodiment 6, wherein $R^1$, $R^3$, $R^4$ and $R^5$ are —OH; $R^{5'}$ is H; R$^{2A}$ is an unsubstituted $C_1$-$C_{10}$ thiol-alkyl or unsubstituted 2 to 10 membered thiol-heteroalkyl; R$^{2B}$ is —C(O)R$^{2C}$, unsubstituted $C_1$-$C_{10}$ thiol-alkyl or unsubstituted thiol-heteroalkyl; and R$^{2C}$ is substituted or unsubstituted $C_1$-$C_{10}$ thiol-alkyl or substituted or unsubstituted 2 to 10 membered thiol-heteroalkyl.

Embodiment 8

The use of embodiment 7, wherein $R^2$ is —NR$^{2B}$.

Embodiment 9

The use of one of embodiments 6 to 8, wherein R$^{2B}$ is —C(O)R$^{2C}$.

Embodiment 10

The use of one of embodiments 6 to 9, wherein R$^{2C}$ is R$^{2C1}$-substituted $C_1$-$C_{10}$ thiol-alkyl or R$^{2C1}$-substituted 2 to 10 membered thiol-heteroalkyl, wherein R$^{2C1}$ is —N(H)C(O)R$^{2C2}$, wherein R$^{2C2}$ is unsubstituted $C_1$-$C_{10}$ alkyl.

Embodiment 11

The use of embodiment 10, wherein R$^{2C2}$ is methyl.

Embodiment 12

The use of embodiment 11, wherein R$^{2A}$ is —N(H)—C(O)—CH(NHAc)—CH$_2$—SH.

Embodiment 13

The use of embodiment 6, wherein $R^2$, $R^3$, $R^4$ are —OH.

Embodiment 14

The use of embodiment 13, wherein R$^{5'}$ is H; $R^5$ is —SH, —OR$^{5A}$ or —NR$^{5B}$, wherein R$^{5A}$ unsubstituted $C_1$-$C_{10}$ thiol-alkyl or unsubstituted 2 to 10 membered thiol-heteroalkyl; R$^{5B}$ is —C(O)R$^{8C}$, unsubstituted $C_1$-$C_{10}$ alkyl or unsubstituted 2 to 10 membered thiol-heteroalkyl; and R$^{5C}$ is substituted or unsubstituted $C_1$-$C_{10}$ thiol-alkyl or substituted or unsubstituted 2 to 10 membered thiol-heteroalkyl.

Embodiment 15

The use of embodiment 14, wherein $R^5$ is —SH.

Embodiment 16

The use of one of embodiments 13 to 15, wherein $R^1$ is OR$^{1A}$.

Embodiment 17

The use of one of embodiments 13 to 16, wherein R$^{1A}$ is unsubstituted $C_1$-$C_5$ alkyl.

Embodiment 18

The use of one of embodiments 13 to 17, wherein R$^{1A}$ is methyl.

Embodiment 19

The use of embodiment 6, wherein $R^3$, $R^4$ and $R^5$ are —OH; and R5' is H.

Embodiment 20

The use of embodiment 19, wherein $R^2$ is —OH.

Embodiment 21

The use of embodiment 20, wherein $R^1$ is —SH, —OR$^{1A}$ or —NR$^{1B}$, wherein R$^{1A}$ is unsubstituted $C_1$-$C_{10}$ thiol-alkyl or unsubstituted 2 to 10 membered thiol-heteroalkyl; R$^{1B}$ is —C(O)R$^{1C}$, unsubstituted $C_1$-$C_{10}$ thiol-alkyl or unsubstituted 2 to 10 membered thiol-heteroalkyl; and R$^{1C}$ is substituted or unsubstituted $C_1$-$C_{10}$ thiol-alkyl or substituted or unsubstituted 2 to 10 membered thiol-heteroalkyl.

Embodiment 22

The use of embodiment 21, wherein $R^1$ is —OR$^{1A}$ and R$^{1A}$ is unsubstituted $C_1$-$C_{10}$ thiol-alkyl.

Embodiment 23

The use of embodiment 19, wherein $R^1$ is —OH.

Embodiment 24

The use of embodiment 23, wherein $R^2$ is —SH, —OR$^{2A}$ or —NR$^{2B}$, wherein R$^{2A}$ is unsubstituted $C_1$-$C_{10}$ thiol-alkyl or unsubstituted 2 to 10 membered thiol-heteroalkyl; R$^{2B}$ is —C(O)R$^{2C}$, unsubstituted $C_1$-$C_{10}$ thiol-alkyl or unsubstituted 2 to 10 membered thiol-heteroalkyl; and R$^{2C}$ is substituted or unsubstituted $C_1$-$C_{10}$ thiol-alkyl or substituted or unsubstituted 2 to 10 membered thiol-heteroalkyl.

Embodiment 25

The use of embodiment 24, wherein $R^2$ is —NR$^{2B}$, and R$^{2B}$ is —C(O)R$^{2C}$.

Embodiment 26

The use of embodiment 25, wherein R$^{2C}$ is unsubstituted $C_1$-$C_{10}$ thiol-alkyl.

Embodiment 27

The use of embodiment 6, wherein $R^4$ is —SH.

Embodiment 28

The use of embodiment 27, wherein $R^1$ is —$OR^{14}$; and $R^2$, $R^3$, and $R^5$ are —OH.

Embodiment 29

The use of embodiment 28, wherein $R^{14}$ is unsubstituted $C_1$-$C_{10}$ alkyl.

Embodiment 30

The use of embodiment 29, wherein $R^{14}$ is methyl.

Embodiment 31

The use of embodiment 6, wherein $R^5$ is —SH; and $R^{5'}$ is H.

Embodiment 32

The use of embodiment 31, wherein $R^1$ is —$OR^{14}$; and $R^2$, $R^3$, and $R^4$ are —OH.

Embodiment 33

The use of embodiment 32, $R^{14}$ is unsubstituted $C_1$-$C_{10}$ alkyl.

Embodiment 34

The use of embodiment 33, wherein $R^{14}$ is methyl.

Embodiment 35

The use of embodiment 6, wherein $R^1$ is —$OR^{14}$; $R^2$, $R^3$, and $R^4$ are —OH; $R^5$ is H or —$OR^{5A}$; and $R^{5'}$ is H.

Embodiment 36

The use of embodiment 35, wherein $R^5$ is H.

Embodiment 37

The use of embodiment 36, wherein $R^{14}$ is substituted or unsubstituted $C_1$-$C_{10}$ thiol-alkyl or substituted or unsubstituted 2 to 10 membered thiol-heteroalkyl.

Embodiment 38

The use of embodiment 37, wherein $R^{14}$ is unsubstituted $C_1$-$C_{10}$ thiol-alkyl.

Embodiment 39

The use of embodiment 38, wherein $R^{14}$ is thiopropyl.

Embodiment 40

The use of embodiment 35, wherein $R^5$ is —$OR^{5A}$.

Embodiment 41

The use of embodiment 40, wherein $R^5$ is —OH.

Embodiment 42

The use of embodiment 41, wherein $R^{14}$ is unsubstituted $C_1$-$C_{10}$ thiol-alkyl.

Embodiment 43

The use of embodiment 42, wherein $R^{14}$ is thiopropyl.

Embodiment 44

The use of embodiment 35, wherein $R^{14}$ is substituted or unsubstituted $C_1$-$C_{10}$ thiol-alkyl or substituted or unsubstituted 2 to 10 membered thiol-heteroalkyl.

Embodiment 45

The use of embodiment 44, wherein $R^5$ is —OH; and $R^{14}$ is or unsubstituted $C_1$-$C_{10}$ thiol-alkyl or unsubstituted 2 to 10 membered thiol-heteroalkyl.

Embodiment 46

The use of embodiment 45, wherein $R^{14}$ is unsubstituted $C_1$-$C_{10}$ thiol-alkyl.

Embodiment 47

The use of embodiment 46, wherein $R^{14}$ is thioethyl, thiopropyl, thiobutyl, or thiopentyl.

Embodiment 48

The use of embodiment 45, wherein $R^{14}$ is unsubstituted 2 to 10 membered thiol-heteroalkyl.

Embodiment 49

The use of embodiment 48, wherein $R^{14}$ is thioethyloxyethyl.

Embodiment 50

The use of embodiment 6, wherein $R^1$ is —$OR^{14}$; $R^2$, $R^3$, and $R^4$ are —OH; $R^{5'}$ is H; and $R^5$ is —SH.

Embodiment 51

The use of embodiment 50, wherein $R^{14}$ is substituted or unsubstituted $C_1$-$C_{10}$ thiol-alkyl.

Embodiment 52

The use of embodiment 51, wherein $R^{14}$ is unsubstituted $C_1$-$C_{10}$ thiol-alkyl.

Embodiment 53

The use of embodiment 52, wherein $R^{14}$ is thioethyl.

Embodiment 54

The use of embodiment 6, wherein $R^1$ is —$OR^{14}$; $R^2$, $R^3$, and $R^4$ are —OH; $R^5$ is —SAc; and $R^{5'}$ is H.

Embodiment 55

The use of embodiment 54, wherein $R^{14}$ is methyl.

Embodiment 56

The use of embodiment 6, wherein $R^1$ is —$OR^{1A}$ or —$R^{1D}$, $R^2$ is —OH or —$NR^{2B}$; $R^{2B}$ is —$C(O)R^{2C}$; $R^{2C}$ is substituted or unsubstituted $C_1$-$C_{10}$ alkyl; $R^3$ and $R^4$ are —OH; and $R^5$ is —$OR^{5A}$ or —$R^{5D}$.

Embodiment 57

The use of embodiment 56, wherein $R^1$ is —$OR^{1A}$.

Embodiment 58

The use of embodiment 57, wherein $R^{1A}$ is unsubstituted $C_1$-$C_5$ alkyl.

Embodiment 59

The use of embodiment 58, wherein $R^{1A}$ is methyl.

Embodiment 60

The use of embodiment 56, wherein $R^1$ is —$R^{1D}$.

Embodiment 61

The use of embodiment 56, wherein $R^5$ is —$OR^{5A}$; $R^{5A}$ is substituted or unsubstituted $C_1$-$C_{10}$ thiol-alkyl or substituted or unsubstituted 2 to 10 membered thiol-heteroalkyl; and $R^{5'}$ is H.

Embodiment 62

The use of embodiment 56, wherein $R^5$ is —$R^{5D}$; and $R^{5'}$ is —OH.

Embodiment 63

The use of embodiment 56, wherein $R^5$ is —$R^{5D}$; and $R^{5'}$ is H.

Embodiment 64

The use of one of embodiments 56 to 63, wherein $R^2$ is —OH.

Embodiment 65

The use of one of embodiments 56 to 63, wherein $R^2$ is —$NR^{2B}$.

Embodiment 66

The use of embodiment 65, wherein $R^2$ is —NHAc.

Embodiment 67

The use of embodiment 1, wherein said thiosaccharide mucolytic agent has the formula:

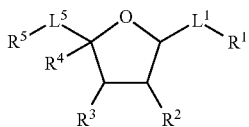

(II)

wherein, $L^1$ and $L^5$ are independently a bond or methylene; R is —SH, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ thiol-alkyl or substituted or unsubstituted 2 to 10 membered thiol-heteroalkyl; $R^3$—SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^4$ is —SH, —$OR^{4A}$ or —$NR^{4B}$ wherein $R^{4A}$ is H, substituted or unsubstituted $C_1$-$C_{10}$ thiol-alkyl or substituted or unsubstituted 2 to 10 membered thiol-heteroalkyl; $R^{4B}$ is —$C(O)R^{4C}$, substituted or unsubstituted $C_1$-$C_{10}$ thiol-alkyl or substituted or unsubstituted 2 to 10 membered thiol-heteroalkyl; and $R^{4C}$ is substituted or unsubstituted $C_1$-$C_{10}$ thiol-alkyl or substituted or unsubstituted 2 to 10 membered thiol-heteroalkyl; and $R^5$ is H, —SH, —$OR^{5A}$ or —$NR^{5B}$ wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —$C(O)R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl.

Embodiment 68

The use of embodiment 1, wherein said thiosaccharide mucolytic agent has the formula:

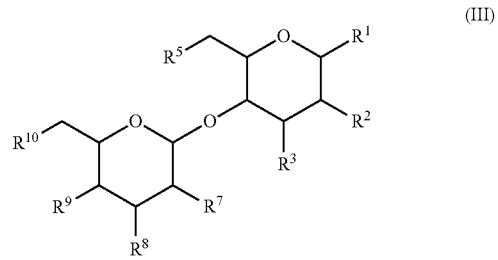

(III)

wherein, $R^1$ is —SH, —$OR^{1A}$ or —$NR^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —C(O)$R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$ is —SH, —O$R^{3A}$ or —N$R^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —C(O)$R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —O$R^{5A}$ or —N$R^{5B}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —C(O)$R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ is —SH, —O$R^{7A}$ or —N$R^{7B}$, wherein $R^{7A}$ is H, substituted or unsubstituted $C_1$-$C_{10}$ thiol-alkyl or substituted or unsubstituted 2 to 10 membered thiol-heteroalkyl; $R^{7B}$ is —C(O)$R^{7C}$, substituted or unsubstituted $C_1$-$C_{10}$ thiol-alkyl or substituted or unsubstituted 2 to 10 membered thiol-heteroalkyl; and $R^{7C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^8$ is —SH, —O$R^{8A}$ or —N$R^{8B}$, wherein $R^{8A}$ is H, substituted or unsubstituted $C_1$-$C_{10}$ thiol-alkyl or substituted or unsubstituted 2 to 10 membered thiol-heteroalkyl; $R^{8B}$ is —C(O)$R^{8C}$, substituted or unsubstituted $C_1$-$C_{10}$ thiol-alkyl or substituted or unsubstituted 2 to 10 membered thiol-heteroalkyl; and $R^{8C}$ is substituted or unsubstituted $C_1$-$C_{10}$ thiol-alkyl or substituted or unsubstituted 2 to 10 membered thiol-heteroalkyl; $R^9$ is —SH, —O$R^{9A}$ or —N$R^{9B}$, wherein $R^{9A}$ is H, substituted or unsubstituted $C_1$-$C_{10}$ thiol-alkyl or substituted or unsubstituted 2 to 10 membered thiol-heteroalkyl; $R^{9B}$ is —C(O)$R^9C$, substituted or unsubstituted $C_1$-$C_{10}$ thiol-alkyl or substituted or unsubstituted 2 to 10 membered thiol-heteroalkyl; and $R^{9C}$ is substituted or unsubstituted $C_1$-$C_{10}$ thiol-alkyl or substituted or unsubstituted 2 to 10 membered thiol-heteroalkyl; $R^{10}$ is H, —SH, —SAc, —O$R^{10A}$ or —N$R^{10B}$, wherein $R^{10A}$ is H, substituted or unsubstituted $C_1$-$C_{10}$ thiol-alkyl or substituted or unsubstituted 2 to 10 membered thiol-heteroalkyl; $R^{10B}$ is —C(O)Roc substituted or unsubstituted $C_1$-$C_{10}$ thiol-alkyl or substituted or unsubstituted 2 to 10 membered thiol-heteroalkyl; and $R^{10C}$ is substituted or unsubstituted $C_1$-$C_{10}$ thiol-alkyl or substituted or unsubstituted 2 to 10 membered thiol-heteroalkyl.

Embodiment 69

The use of embodiment 68, wherein $R^L$ is —O$R^{1A}$; and $R^2$, $R^3$, $R^5$, $R^7$, $R^8$, and $R^9$ are —OH; and $R^{10}$ is —SH or —O$R^{10A}$.

Embodiment 70

The use of embodiment 69, wherein $R^{1A}$ is substituted or unsubstituted $C_1$-$C_{10}$ thiol-alkyl or substituted or unsubstituted 2 to 10 membered thiol-heteroalkyl.

Embodiment 71

The use of embodiment 70, wherein $R^{1A}$ is unsubstituted $C_1$-$C_{10}$ thiol-alkyl; and $R^{10}$ is —OH.

Embodiment 72

The use of embodiment 71, wherein $R^{1A}$ is thioethyl.

Embodiment 73

The use of embodiment 69, wherein $R^{1A}$ is H; and $R^{10}$ is —SH.

Embodiment 74

The use of embodiment 68, wherein $R^{1A}$ is substituted or unsubstituted $C_1$-$C_{10}$ thiol-alkyl or substituted or unsubstituted 2 to 10 membered thiol-heteroalkyl; $R^2$, $R^3$, $R^5$, $R^7$, $R^8$, and $R^9$ are —OH; and $R^{10}$ is —SH.

Embodiment 75

The use of embodiment 74, wherein $R^{1A}$ is unsubstituted $C_1$-$C_{10}$ thiol-alkyl.

Embodiment 76

The use of embodiment 75, wherein $R^{1A}$ is thioethyl.

Embodiment 77

The use of embodiment 68, wherein $R^1$, $R^3$, $R^5$, $R^8$, $R^9$, and $R^{10}$ are —OH; $R^2$ is —OH or —N$R^{2B}$; $R^{2C}$ is substituted or unsubstituted $C_1$-$C_{10}$ thiol-alkyl; $R^7$ is —OH or —N$R^{7B}$; and $R^{7C}$ is substituted or unsubstituted $C_1$-$C_{10}$ thiol-alkyl.

Embodiment 78

The use of embodiment 68, wherein $R^L$ is —O$R^{1A}$; $R^{1A}$ is substituted or unsubstituted $C_1$-$C_{10}$ thiol-alkyl or substituted or unsubstituted 2 to 10 membered thiol-heteroalkyl; $R^3$, $R^5$, $R^8$, $R^9$, and $R^{10}$ are —OH; $R^2$ is —OH or —N$R^{2B}$; $R^{2C}$ is substituted or unsubstituted $C_1$-$C_{10}$ alkyl; $R^7$ is —OH or —N$R^{7B}$; and $R^{7C}$ is substituted or unsubstituted $C_1$-$C_{10}$alkyl.

Embodiment 79

The use of embodiment 78, wherein $R^2$ is —NHAc; and $R^7$ is —NHAc.

Embodiment 80

The use of embodiment 1, wherein said thiosaccharide mucolytic agent has the formula:

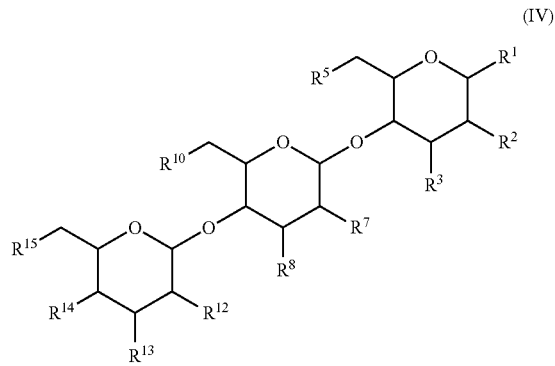

(IV)

wherein, $R^1$ is —SH, —OR$^{1A}$ or —NR$^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —C(O)R$^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —OR$^{2A}$ or —NR$^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —C(O)R$^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$ is —SH, —OR$^{3A}$ or —NR$^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —C(O)R$^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —OR$^{5A}$ or —NR$^{5B}$, wherein $R^{5A}$ is H, substituted or unsubstituted $C_1$-$C_{10}$ thiol-alkyl or substituted or unsubstituted 2 to 10 membered thiol-heteroalkyl, $R^{5B}$ is —C(O)R$^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ is —SH, —OR$^{7A}$ or —NR$^{7B}$, wherein $R^{7A}$ is H, substituted or unsubstituted $C_1$-$C_{10}$ thiol-alkyl or substituted or unsubstituted 2 to 10 membered thiol-heteroalkyl; $R^{7B}$ is —C(O)R$^{7C}$, substituted or unsubstituted $C_1$-$C_{10}$ thiol-alkyl or substituted or unsubstituted 2 to 10 membered thiol-heteroalkyl; and $R^{7C}$ is substituted or unsubstituted $C_1$-$C_{10}$ thiol-alkyl or substituted or unsubstituted 2 to 10 membered thiol-heteroalkyl; $R^8$ is —SH, —OR$^{8A}$ or —NR$^{8B}$, wherein $R^{8A}$ is H, substituted or unsubstituted $C_1$-$C_{10}$ thiol-alkyl or substituted or unsubstituted 2 to 10 membered thiol-heteroalkyl; $R^{8B}$ is —C(O)R$^{8C}$, substituted or unsubstituted $C_1$-$C_{10}$ thiol-alkyl or substituted or unsubstituted 2 to 10 membered thiol-heteroalkyl; and $R^{8C}$ is substituted or unsubstituted $C_1$-$C_{10}$ thiol-alkyl or substituted or unsubstituted 2 to 10 membered thiol-heteroalkyl; $R^{10}$ is H, —SH, —SAc, —OR$^{10A}$ or —NR$^{10B}$, wherein $R^{10A}$ is H, substituted or unsubstituted $C_1$-$C_{10}$ thiol-alkyl or substituted or unsubstituted 2 to 10 membered thiol-heteroalkyl; $R^{10B}$ is —C(O)R$^{10C}$, substituted or unsubstituted $C_1$-$C_{10}$ thiol-alkyl or substituted or unsubstituted 2 to 10 membered thiol-heteroalkyl; and $R^{10C}$ is substituted or unsubstituted $C_1$-$C_{10}$ thiol-alkyl or substituted or unsubstituted 2 to 10 membered thiol-heteroalkyl; $R^{12}$—SH, —OR$^{12A}$ or —NR$^{12B}$, wherein $R^{12A}$ is H, substituted or unsubstituted $C_1$-$C_{10}$ thiol-alkyl or substituted or unsubstituted 2 to 10 membered thiol-heteroalkyl; $R^{2B}$ is —C(O)R$^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ thiol-alkyl or substituted or unsubstituted 2 to 10 membered thiol-heteroalkyl; $R^{13}$—SH, —OR$^{13A}$ or —NR$^{3B}$ wherein $R^{13A}$ is H, substituted or unsubstituted $C_1$-$C_{10}$ thiol-alkyl or substituted or unsubstituted 2 to 10 membered thiol-heteroalkyl; $R^{13B}$ is —C(O)R$^{13C}$, substituted or unsubstituted $C_1$-$C_{10}$ thiol-alkyl or substituted or unsubstituted 2 to 10 membered thiol-heteroalkyl; and $R^{13C}$ is substituted or unsubstituted $C_1$-$C_{10}$ thiol-alkyl or substituted or unsubstituted 2 to 10 membered thiol-heteroalkyl; $R^{14}$ is —SH, —OR$^{14A}$ or —NR$^{14B}$, wherein $R^{14A}$ is H, substituted or unsubstituted $C_1$-$C_{10}$ thiol-alkyl or substituted or unsubstituted 2 to 10 membered thiol-heteroalkyl; $R^{14B}$ is —C(O)R$^{14C}$, substituted or unsubstituted $C_1$-$C_{10}$ thiol-alkyl or substituted or unsubstituted 2 to 10 membered thiol-heteroalkyl; and $R^{14C}$ is substituted or unsubstituted $C_1$-$C_{10}$ thiol-alkyl or substituted or unsubstituted 2 to 10 membered thiol-heteroalkyl; and $R^{15}$ is H, —SH, —SAc, —OR$^{15A}$ or —NR$^{15B}$, wherein $R^{15A}$ is H, substituted or unsubstituted $C_1$-$C_{10}$ thiol-alkyl or substituted or unsubstituted 2 to 10 membered thiol-heteroalkyl; $R^{15B}$ is —C(O)R$^{15C}$, substituted or unsubstituted $C_1$-$C_{10}$ thiol-alkyl or substituted or unsubstituted 2 to 10 membered thiol-heteroalkyl; and $R^{15C}$ is substituted or unsubstituted $C_1$-$C_{10}$ thiol-alkyl or substituted or unsubstituted 2 to 10 membered thiol-heteroalkyl.

Embodiment 81

The use of embodiment 80, wherein $R^1$, $R^3$, $R^5$, $R^8$, $R^{10}$, $R^{13}$, $R^{14}$ and $R^{15}$ are —OH; $R^2$ is —OH or —NR$^{2B}$; $R^{2B}$ is —C(O)R$^{2C}$; $R^{2C}$ is substituted or unsubstituted $C_1$-$C_{10}$ thiol-alkyl or substituted or unsubstituted 2 to 10 membered thiol-heteroalkyl; $R^7$ is —OH or —NH$^{7B}$; $R^{7B}$ is —C(O)R$^{7C}$; $R^{7C}$ is substituted or unsubstituted $C_1$-$C_{10}$ thiol-alkyl or substituted or unsubstituted 2 to 10 membered thiol-heteroalkyl; $R^{12}$ is —OH or —NH$^{12B}$; $R1^{2B}$ is —C(O)R1$^{2C}$; and $R1^2C$ is substituted or unsubstituted $C_1$-$C_{10}$ thiol-alkyl or substituted or unsubstituted 2 to 10 membered thiol-heteroalkyl.

Embodiment 82

The use of embodiment 1, wherein said thiosaccharide mucolytic agent has the formula:

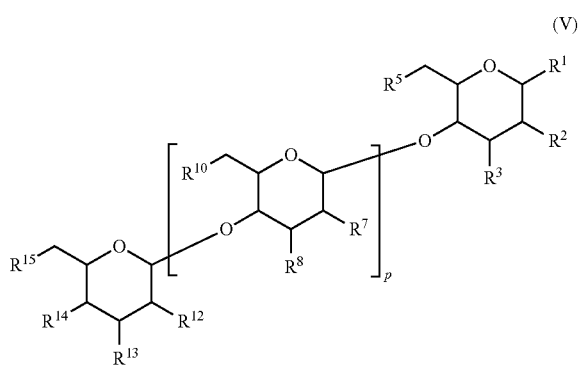

(V)

wherein, $R^1$ is —SH, —OR$^{1A}$ or —NR$^{1B}$, wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —C(O)R$^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —OR$^{2A}$ or —NR$^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —C(O)R$^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$ is —SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —$OR^{5A}$ or —$NR^{5B}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —$C(O)R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ at each occurrence is independently —SH, —$OR^{7A}$ or —$NR^{7B}$, wherein $R^{7A}$ at each occurrence is independently H, substituted or unsubstituted $C_1$-$C_{10}$ thiol-alkyl or substituted or unsubstituted 2 to 10 membered thiol-heteroalkyl; $R^{7B}$ at each occurrence is independently —$C(O)R^{7C}$, substituted or unsubstituted $C_1$-$C_{10}$ thiol-alkyl or substituted or unsubstituted 2 to 10 membered thiol-heteroalkyl; and $R^{7C}$ at each occurrence is independently substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^8$ at each occurrence is independently —SH, —$OR^{8A}$ or —$NR^{8B}$, wherein $R^{8A}$ at each occurrence is independently H, substituted or unsubstituted $C_1$-$C_{10}$ thiol-alkyl or substituted or unsubstituted 2 to 10 membered thiol-heteroalkyl; $R^{8B}$ at each occurrence is independently —$C(O)R^{8C}$, substituted or unsubstituted $C_1$-$C_{10}$ thiol-alkyl or substituted or unsubstituted 2 to 10 membered thiol-heteroalkyl; and $R^{8C}$ at each occurrence is independently substituted or unsubstituted $C_1$-$C_{10}$ thiol-alkyl or substituted or unsubstituted 2 to 10 membered thiol-heteroalkyl; $R^{10}$ at each occurrence is independently H, —SH, —SAc, —$OR^{10A}$ or —$NR^{10B}$, wherein $R^{10A}$ at each occurrence is independently H, substituted or unsubstituted $C_1$-$C_{10}$ thiol-alkyl or substituted or unsubstituted 2 to 10 membered thiol-heteroalkyl; $R^{10B}$ at each occurrence is independently —$C(O)R^{10C}$, substituted or unsubstituted $C_1$-$C_{10}$ thiol-alkyl or substituted or unsubstituted 2 to 10 membered thiol-heteroalkyl; and $R^{10C}$ at each occurrence is independently substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{12}$ is —SH, —$OR^{2A}$ or —$NR^{2B}$, wherein $R^{12A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{12C}$ is substituted or unsubstituted $C_1$-$C_{10}$ thiol-alkyl or substituted or unsubstituted 2 to 10 membered thiol-heteroalkyl; $R^{13}$ is —SH, —$OR^{13A}$ or —$NR^{13B}$, wherein $R^{13A}$ is H, substituted or unsubstituted $C_1$-$C_{10}$ thiol-alkyl or substituted or unsubstituted 2 to 10 membered thiol-heteroalkyl; $R^{13B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^{14}$ is —SH, —$OR^{14A}$ or —$NR^{14B}$, wherein $R^{14A}$ is H, substituted or unsubstituted $C_1$-$C_{10}$ thiol-alkyl or substituted or unsubstituted 2 to 10 membered thiol-heteroalkyl; $R^{4B}$ is —$C(O)R^{4C}$, substituted or unsubstituted $C_1$-$C_{10}$ thiol-alkyl or substituted or unsubstituted 2 to 10 membered thiol-heteroalkyl; and $R^{4C}$ is substituted or unsubstituted $C_1$-$C_{10}$ thiol-alkyl or substituted or unsubstituted 2 to 10 membered thiol-heteroalkyl; and $R^{15}$ is H, —SH, —SAc, —$OR^{5A}$ or —$NR^{15B}$, wherein $R^{15A}$ is H, substituted or unsubstituted $C_1$-$C_{10}$ thiol-alkyl or substituted or unsubstituted 2 to 10 membered thiol-heteroalkyl; $R^{15B}$ is —$C(O)R^{5C}$, substituted or unsubstituted $C_1$-$C_{10}$ thiol-alkyl or substituted or unsubstituted 2 to 10 membered thiol-heteroalkyl; and $R^{15C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; and p is 2-10.

Embodiment 83

A compound with structure of Formula (I):

wherein, $R^1$ is —SH, —$OR^{1A}$, —$NR^{1B}$ or —$R^{1D}$, wherein $R^{1A}$ is H, substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^{1B}$ is —$C(O)R^{1C}$, substituted or unsubstituted $C_1$-$C_{10}$ thiol-alkyl or substituted or unsubstituted 2 to 10 membered thiol-heteroalkyl; $R^{1C}$ is substituted or unsubstituted $C_1$-$C_{10}$ thiol-alkyl or substituted or unsubstituted 2 to 10 membered thiol-heteroalkyl; and $R^{1D}$ is substituted or unsubstituted $C_1$-$C_{10}$ thiol-alkyl or substituted or unsubstituted 2 to 10 membered thiol-heteroalkyl; $R^2$—SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —$C(O)R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$—SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —$C(O)R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^4$ is —SH, —SAc, —$OR^{4A}$ or —$NR^{4B}$, wherein $R^{4A}$ is H, substituted or unsubstituted $C_1$-$C_{10}$ thiol-alkyl or substituted or unsubstituted 2 to 10 membered thiol-heteroalkyl; $R^{4B}$ is —$C(O)R^{4C}$, substituted or unsubstituted $C_1$-$C_{10}$ thiol-alkyl or substituted or unsubstituted 2 to 10 membered thiol-heteroalkyl; and $R^{4C}$ is substituted or unsubstituted $C_1$-$C_{10}$ thiol-alkyl or substituted or unsubstituted 2 to 10 membered thiol-heteroalkyl; and $R^5$ is H, —SH, —SAc, —$OR^{5A}$, —$NR^{5B}$, or —$R^{5D}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —$C(O)R^{5C}$, substituted or unsubstituted $C_1$-$C_{10}$ thiol-alkyl or substituted or unsubstituted 2 to 10 membered thiol-heteroalkyl; $R^{5C}$ is substituted or unsubstituted $C_1$-$C_{10}$ thiol-alkyl or substituted or unsubstituted 2 to 10 membered thiol-heteroalkyl; and $R^{5D}$ is substituted or unsubstituted $C_1$-$C_{10}$ thiol-alkyl; and $R^{5'}$ is H or —OH; provided, however, that said structure is not

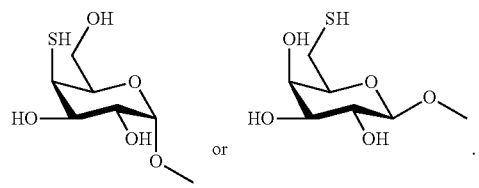

Embodiment 84

The compound of embodiment 83, having the structure

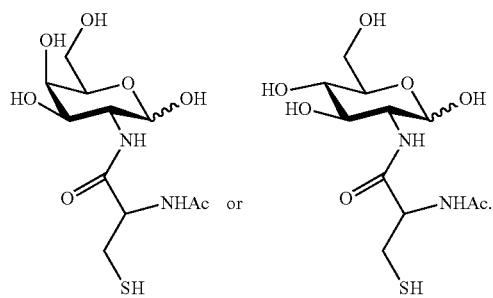

Embodiment 85

The compound of embodiment 85, having the structure

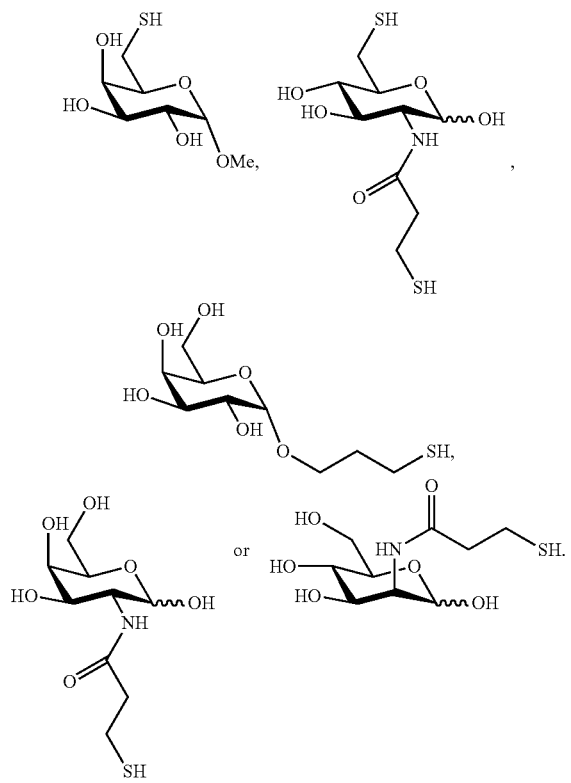

Embodiment 86

The compound of embodiment 85, having the structure

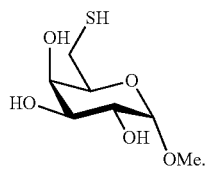

Embodiment 87

The compound of embodiment 83, having the structure

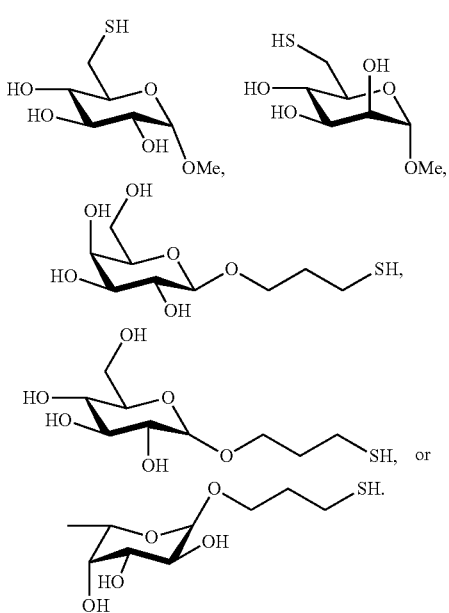

Embodiment 88

The compound of embodiment 83, having the structure

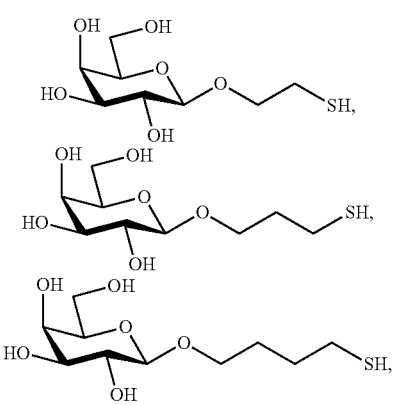

-continued

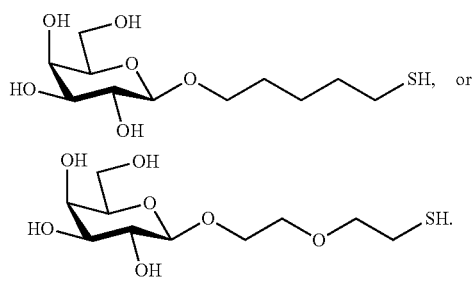

Embodiment 89

The compound of embodiment 83, having the structure

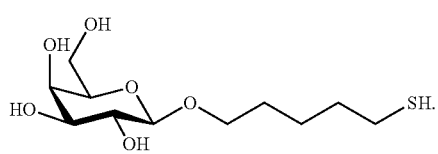

Embodiment 90

The compound of embodiment 83, having the structure

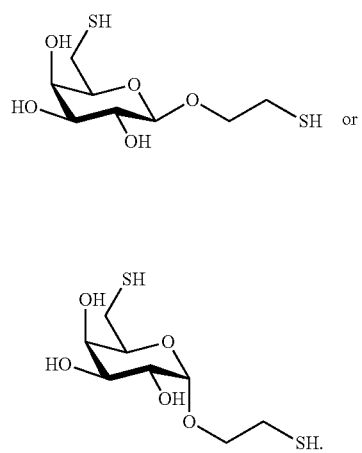

Embodiment 91

The compound of embodiment 83, having the structure

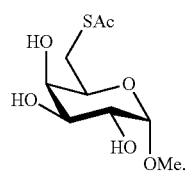

Embodiment 92

A compound with structure of Formula (III):

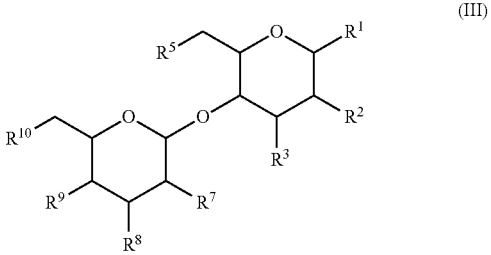

wherein, $R^1$ is —SH, —OR$^{1A}$ or —NR$^{1B}$, wherein R$^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; R$^{1B}$ is —C(O) R$^{1C}$, substituted or unsubstituted $C_1$-$C_{10}$ thiol-alkyl or substituted or unsubstituted 2 to 10 membered thiol-heteroalkyl; and R$^{1C}$ is substituted or unsubstituted $C_1$-$C_{10}$ thiol-alkyl or substituted or unsubstituted 2 to 10 membered thiol-heteroalkyl; $R^2$ is —SH, —OR$^{2A}$ or —NR$^{2B}$, wherein R$^{2A}$ is H, substituted or unsubstituted $C_1$-$C_{10}$ thiol-alkyl or substituted or unsubstituted 2 to 10 membered thiol-heteroalkyl; R$^{2B}$ is —C(O)R$^{2C}$, substituted or unsubstituted $C_1$-$C_{10}$ thiol-alkyl or substituted or unsubstituted 2 to 10 membered thiol-heteroalkyl; and R$^{2C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^3$ is —SH, —OR$^{3A}$ or —NR$^{3B}$, wherein R$^{3A}$ is H, substituted or unsubstituted $C_1$-$C_{10}$ thiol-alkyl or substituted or unsubstituted 2 to 10 membered thiol-heteroalkyl; R$^{3B}$ is —C(O)R$^{3C}$, substituted or unsubstituted $C_1$-$C_{10}$ thiol-alkyl or substituted or unsubstituted 2 to 10 membered thiol-heteroalkyl; and R$^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —OR$^{5A}$ or —NR$^{5B}$, wherein R$^{5A}$ is H, substituted or unsubstituted $C_1$-$C_{10}$ thiol-alkyl or substituted or unsubstituted 2 to 10 membered thiol-heteroalkyl; R$^{5B}$ is —C(O)R$^{5C}$, substituted or unsubstituted $C_1$-$C_{10}$ thiol-alkyl or substituted or unsubstituted 2 to 10 membered thiol-heteroalkyl; and R$^{5C}$ is substituted or unsubstituted $C_1$-$C_{10}$ thiol-alkyl or substituted or unsubstituted 2 to 10 membered thiol-heteroalkyl; $R^7$ is —SH, —OR$^{7A}$ or —NR$^{7B}$, wherein R$^{7A}$ is H, substituted or unsubstituted $C_1$-$C_{10}$ thiol-alkyl or substituted or unsubstituted 2 to 10 membered thiol-heteroalkyl; R$^{7B}$ is —C(O) R$^{7C}$, substituted or unsubstituted $C_1$-$C_{10}$ thiol-alkyl or substituted or unsubstituted 2 to 10 membered thiol-heteroalkyl; and R$^{7C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^8$ is —SH, —OR$^{8A}$ or —NR$^{8B}$, wherein R$^{8A}$ is H, substituted or unsubstituted $C_1$-$C_{10}$ thiol-alkyl or substituted or unsubstituted 2 to 10 membered thiol-heteroalkyl; R$^{8B}$ is —C(O) R$^{8C}$, substituted or unsubstituted $C_1$-$C_{10}$ thiol-alkyl or substituted or unsubstituted 2 to 10 membered thiol-heteroalkyl; and R$^{8C}$ is substituted or unsubstituted $C_1$-$C_{10}$ thiol-alkyl or substituted or unsubstituted 2 to 10 membered thiol-heteroalkyl; $R^9$ is —SH, —OR$^{9A}$ or —NR$^{9B}$ wherein R$^{9A}$ is H, substituted or unsubstituted $C_1$-$C_{10}$ thiol-alkyl or substituted or unsubstituted 2 to 10 membered thiol-heteroalkyl; R$^{9B}$ is —C(O)R$^{9C}$, substituted or unsubstituted $C_1$-$C_{10}$ thiol-alkyl or substituted or unsubstituted 2 to 10 membered thiol-heteroalkyl; and $R^{9C}$ is substituted or unsubstituted $C_1$-$C_{10}$ thiol-alkyl or substituted or unsubstituted 2 to 10 membered thiol-heteroalkyl; and $R^{10}$ is H, —SH, —SAc, —$OR^{10A}$ or —$NR^{10B}$, wherein $R^{10A}$ is H, substituted or unsubstituted $C_1$-$C_{10}$ thiol-alkyl or substituted or unsubstituted 2 to 10 membered thiol-heteroalkyl; $R^{10B}$ is —C(O)$R^{10C}$, substituted or unsubstituted $C_1$-$C_{10}$ thiol-alkyl or substituted or unsubstituted 2 to 10 membered thiol-heteroalkyl; and $R^{10C}$ is substituted or unsubstituted $C_1$-$C_{10}$ thiol-alkyl or substituted or unsubstituted 2 to 10 membered thiol-heteroalkyl.

Embodiment 93

The compound of embodiment 92, having the structure

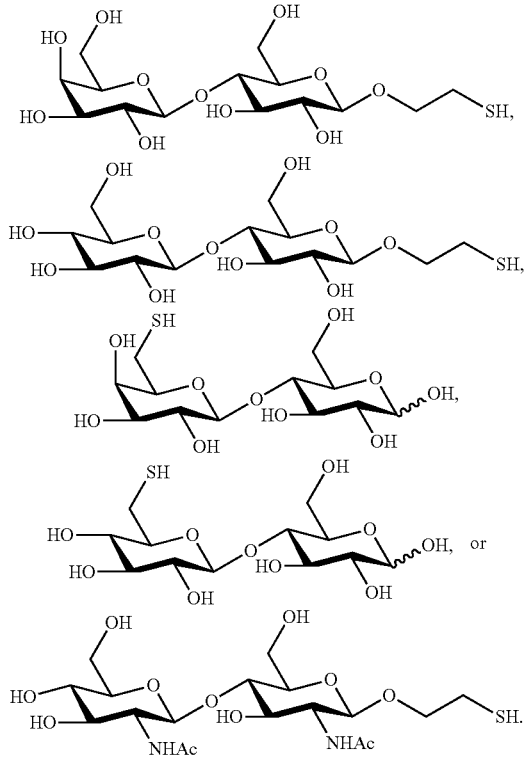

Embodiment 94

The compound of embodiment 92, having the structure

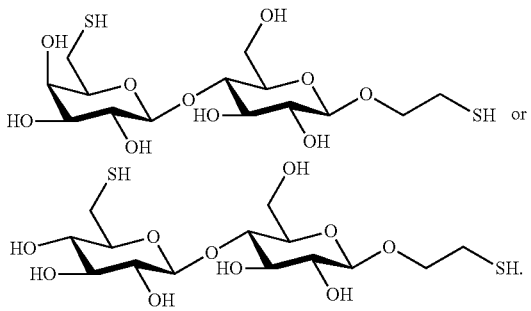

Embodiment 95

A compound with structure of Formula (IV):

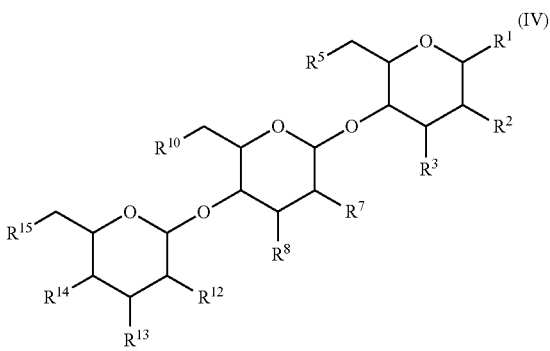

wherein, $R^1$ is —SH, —$OR^{1A}$ or —$NR^{1B}$, wherein $R^{1A}$ is H, substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^{1B}$ is —C(O)$R^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —$OR^{2A}$ or —$NR^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —C(O)$R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$ is —SH, —$OR^{3A}$ or —$NR^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —C(O)$R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —$OR^{5A}$ or —$NR^{5B}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —C(O)$R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ is —SH, —$OR^{7A}$ or —$NR^{7B}$, wherein $R^{7A}$ is H, substituted or unsubstituted $C_1$-$C_{10}$ thiol-alkyl or substituted or unsubstituted 2 to 10 membered thiol-heteroalkyl; $R^{7B}$ is —C(O)$R^{7C}$, substituted or unsubstituted $C_1$-$C_{10}$ thiol-alkyl or substituted or unsubstituted 2 to 10 membered thiol-heteroalkyl; and $R^{7C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^8$ is —SH, —$OR^{8A}$ or —$NR^{8B}$, wherein $R^{8A}$ is H, substituted or unsubstituted $C_1$-$C_{10}$ thiol-alkyl or substituted or unsubstituted 2 to 10 membered thiol-heteroalkyl; $R^{8B}$ is —C(O)$R^{8C}$, substituted or unsubstituted $C_1$-$C_{10}$ thiol-alkyl or substituted or unsubstituted 2 to 10 membered thiol-heteroalkyl; and $R^{8C}$ is substituted or unsubstituted $C_1$-$C_{10}$ thiol-alkyl or substituted or unsubstituted 2 to 10 membered thiol-heteroalkyl; $R^{10}$ is H, —SH, —SAc, —$OR^{1A}$ or —$NR^{10B}$, wherein $R^{10A}$ is H, substituted or unsubstituted $C_1$-$C_{10}$ thiol-alkyl or substituted or unsubstituted 2 to 10 membered thiol-heteroalkyl; $R^{10B}$ is —C(O)$R^{10C}$, substituted or unsubstituted $C_1$-$C_{10}$ thiol-alkyl or substituted or unsubstituted 2 to 10 membered thiol-heteroalkyl; and $R^{10C}$ is substituted or unsubstituted $C_1$-$C_{10}$ thiol-alkyl or substituted or unsubstituted 2 to 10 membered thiol-heteroalkyl; $R^{12}$ is —SH, —OR$^{12A}$ or —NR$^{12B}$, wherein $R^{12A}$ is H, substituted or unsubstituted $C_1$-$C_{10}$ thiol-alkyl or substituted or unsubstituted 2 to 10 membered thiol-heteroalkyl; $R^{2B}$ is —C(O)$R^{12C}$, substituted or unsubstituted $C_1$-$C_{10}$ thiol-alkyl or substituted or unsubstituted 2 to 10 membered thiol-heteroalkyl; and $R^{12C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{13}$ is —SH, —OR$^{13A}$ or —NR$^{13B}$, wherein $R^{13A}$ is H, substituted or unsubstituted $C_1$-$C_{10}$ thiol-alkyl or substituted or unsubstituted 2 to 10 membered thiol-heteroalkyl; $R^{13B}$ is —C(O)$R^{13C}$, substituted or unsubstituted $C_1$-$C_{10}$ thiol-alkyl or substituted or unsubstituted 2 to 10 membered thiol-heteroalkyl; and $R^{13C}$ is substituted or unsubstituted $C_1$-$C_{10}$ thiol-alkyl or substituted or unsubstituted 2 to 10 membered thiol-heteroalkyl; $R^{14}$ is —SH, —OR$^{14A}$ or —NR$^{14B}$, wherein $R^{14A}$ is H, substituted or unsubstituted $C_1$-$C_{10}$ thiol-alkyl or substituted or unsubstituted 2 to 10 membered thiol-heteroalkyl; $R^{14B}$ is —C(O)$R^{14C}$, substituted or unsubstituted $C_1$-$C_{10}$ thiol-alkyl or substituted or unsubstituted 2 to 10 membered thiol-heteroalkyl; and $R^{14C}$ is substituted or unsubstituted $C_1$-$C_{10}$ thiol-alkyl or substituted or unsubstituted 2 to 10 membered thiol-heteroalkyl; and $R^{15}$ is H, —SH, —SAc, —OR$^{15A}$ or —NR$^{15B}$, wherein $R^{15A}$ is H, substituted or unsubstituted $C_1$-$C_{10}$ thiol-alkyl or substituted or unsubstituted 2 to 10 membered thiol-heteroalkyl; $R^{15B}$ is —C(O)$R^{15C}$, substituted or unsubstituted $C_1$-$C_{10}$ thiol-alkyl or substituted or unsubstituted 2 to 10 membered thiol-heteroalkyl; and $R^{15C}$ is substituted or unsubstituted $C_1$-$C_{10}$ thiol-alkyl or substituted or unsubstituted 2 to 10 membered thiol-heteroalkyl.

Embodiment 96

A compound with structure of Formula (V):

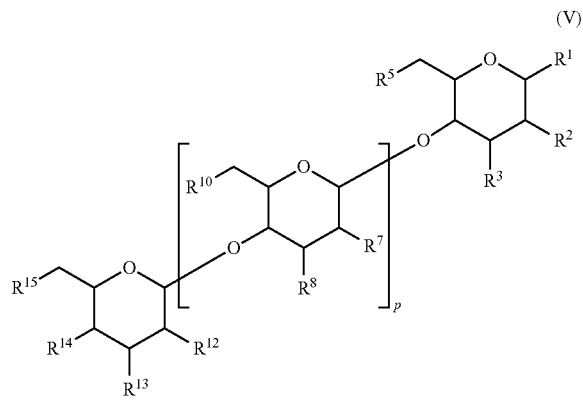

(V)

wherein, $R^1$ is —SH, —OR$^{1A}$ or —NR$^{1B}$ wherein $R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^{1B}$ is —C(O)$R^{1C}$, substituted or unsubstituted $C_1$-$C_{10}$ thiol-alkyl or substituted or unsubstituted 2 to 10 membered thiol-heteroalkyl; and $R^{1C}$ is substituted or unsubstituted $C_1$-$C_{10}$ thiol-alkyl or substituted or unsubstituted 2 to 10 membered thiol-heteroalkyl; $R^2$ is —SH, —OR$^{2A}$ or —NR$^{2B}$, wherein $R^{2A}$ is H, substituted or unsubstituted $C_1$-$C_{10}$ thiol-alkyl or substituted or unsubstituted 2 to 10 membered thiol-heteroalkyl; $R^{2B}$ is —C(O)$R^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^3$ is —SH, —OR$^{3A}$ or —NR$^{3B}$, wherein $R^{3A}$ is H, substituted or unsubstituted $C_1$-$C_{10}$ thiol-alkyl or substituted or unsubstituted 2 to 10 membered thiol-heteroalkyl; $R^{3B}$ is —C(O)$R^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl; $R^5$ is H, —SH, —SAc, —OR$^{5A}$ or —NR$^{5B}$, wherein $R^{5A}$ is H, substituted or unsubstituted $C_1$-$C_{10}$ thiol-alkyl or substituted or unsubstituted 2 to 10 membered thiol-heteroalkyl; $R^{5B}$ is —C(O)$R^{5C}$, substituted or unsubstituted $C_1$-$C_{10}$ thiol-alkyl or substituted or unsubstituted 2 to 10 membered thiol-heteroalkyl; and $R^{5C}$ is substituted or unsubstituted $C_1$-$C_{10}$ thiol-alkyl or substituted or unsubstituted 2 to 10 membered thiol-heteroalkyl; $R^7$ is at each occurrence is independently —SH, —OR$^{7A}$ or —NR$^{7B}$, wherein $R^{7A}$ is H, substituted or unsubstituted $C_1$-$C_{10}$ thiol-alkyl or substituted or unsubstituted 2 to 10 membered thiol-heteroalkyl; $R^{7B}$ is —C(O)$R^{7C}$, substituted or unsubstituted $C_1$-$C_{10}$ thiol-alkyl or substituted or unsubstituted 2 to 10 membered thiol-heteroalkyl; and $R^{7C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl; $R^8$ at each occurrence is independently-SH, —OR$^{8A}$ or —NR$^{8B}$, wherein $R^{8A}$ is H, substituted or unsubstituted $C_1$-$C_{10}$ thiol-alkyl or substituted or unsubstituted 2 to 10 membered thiol-heteroalkyl; $R^{8B}$ is —C(O)$R^{8C}$, substituted or unsubstituted $C_1$-$C_{10}$ thiol-alkyl or substituted or unsubstituted 2 to 10 membered thiol-heteroalkyl; and $R^{8C}$ is substituted or unsubstituted $C_1$-$C_{10}$ thiol-alkyl or substituted or unsubstituted 2 to 10 membered thiol-heteroalkyl; $R^{10}$ at each occurrence is independently H, —SH, —SAc, —OR$^{1A}$ or —NR$^{1B}$, wherein $R^{10A}$ is H, substituted or unsubstituted $C_1$-$C_{10}$ thiol-alkyl or substituted or unsubstituted 2 to 10 membered thiol-heteroalkyl; $R^{10B}$ is —C(O)$R^{10C}$, substituted or unsubstituted $C_1$-$C_{10}$ thiol-alkyl or substituted or unsubstituted 2 to 10 membered thiol-heteroalkyl; and $R^{10C}$ is substituted or unsubstituted $C_1$-$C_{10}$ thiol-alkyl or substituted or unsubstituted 2 to 10 membered thiol-heteroalkyl; $R^{12}$ is —SH, —OR$^{2A}$ or —NR$^{12B}$, wherein $R^{12A}$ is H, substituted or unsubstituted $C_1$-$C_{10}$ thiol-alkyl or substituted or unsubstituted 2 to 10 membered thiol-heteroalkyl; $R^{2B}$ is —C(O)$R^{12C}$, substituted or unsubstituted $C_1$-$C_{10}$ thiol-alkyl or substituted or unsubstituted 2 to 10 membered thiol-heteroalkyl; and $R^{12C}$ is substituted or unsubstituted $C_1$-$C_{10}$alkyl, substituted or unsubstituted $C_1$-$C_{10}$ thiol-alkyl or substituted or unsubstituted 2 to 10 membered thiol-heteroalkyl; $R^{13}$ is —SH, —OR$^{13A}$ or —NR$^{13B}$, wherein $R^{13A}$ is H, substituted or unsubstituted $C_1$-$C_{10}$ thiol-alkyl or substituted or unsubstituted 2 to 10 membered thiol-heteroalkyl; $R^{13B}$ is —C(O)$R^{3C}$, substituted or unsubstituted $C_1$-$C_{10}$ thiol-alkyl or substituted or unsubstituted 2 to 10 membered thiol-heteroalkyl; and $R^{13C}$ is substituted or unsubstituted $C_1$-$C_{10}$ thiol-alkyl or substituted or unsubstituted 2 to 10 membered thiol-heteroalkyl; $R^{14}$ is —SH, —OR$^{14A}$ or —NR$^{14B}$, wherein $R^{14A}$ is H, substituted or unsubstituted $C_1$-$C_{10}$ thiol-alkyl or substituted or unsubstituted 2 to 10 membered thiol-heteroalkyl; $R^{14B}$ is —C(O)$R^{14C}$, substituted or unsubstituted $C_1$-$C_{10}$ thiol-alkyl or substituted or unsubstituted 2 to 10 membered thiol-heteroalkyl; and $R^{14C}$ is substituted or unsubstituted $C_1$-$C_{10}$ thiol-alkyl or substituted or unsubstituted 2 to 10 membered thiol-heteroalkyl; and $R^{15}$ is H, —SH, —SAc, —$OR^{15A}$ or —$NR^{15B}$, wherein $R^{15A}$ is H, substituted or unsubstituted $C_1$-$C_{10}$ thiol-alkyl or substituted or unsubstituted 2 to 10 membered thiol-heteroalkyl; $R^{15B}$ is —C(O)$R^{5C}$, substituted or unsubstituted $C_1$-$C_{10}$ thiol-alkyl or substituted or unsubstituted 2 to 10 membered thiol-heteroalkyl; and $R^{15C}$ is substituted or unsubstituted $C_1$-$C_{10}$ thiol-alkyl or substituted or unsubstituted 2 to 10 membered thiol-heteroalkyl; and p is 2-10.

Embodiment 97

A pulmonary pharmaceutical composition including a pulmonary pharmaceutical carrier and a thiosaccharide mucolytic agent.

Embodiment 98

The pulmonary pharmaceutical composition of embodiment 97, wherein said pulmonary pharmaceutical carrier is a pulmonary pharmaceutical liquid or pulmonary pharmaceutical powder.

Embodiment 99

The pulmonary pharmaceutical composition of embodiment 98, wherein said pulmonary pharmaceutical liquid comprises a polar liquid, and said thiosaccharide mucolytic agent is dissolved or suspended in said polar liquid.

Embodiment 100

The pulmonary pharmaceutical composition of embodiment 99, wherein said polar liquid is water.

Embodiment 101

The pulmonary pharmaceutical composition of embodiment 98, wherein said pulmonary pharmaceutical carrier is lactose, mannitol, a phospholipid or cholesterol.

Embodiment 102

The pulmonary pharmaceutical composition of embodiment 98, wherein said pulmonary pharmaceutical carrier is the parent sugar of said thiosaccharide mucolytic agent, said parent sugar lacking a thiol moiety.

Embodiment 103

The pulmonary pharmaceutical composition of embodiment 97, wherein said pulmonary pharmaceutical composition is within a pulmonary pharmaceutical delivery device.

Embodiment 104

The pulmonary pharmaceutical composition of embodiment 103, wherein said pulmonary pharmaceutical delivery device is a pulmonary pharmaceutical nebulizer, a pulmonary pharmaceutical dry powder inhaler, or a pulmonary pharmaceutical pressurized metered dose inhaler.

What is claimed is:
1. A method for decreasing mucus elasticity or decreasing mucus viscosity in a subject in need thereof, said method comprising administering to said subject in need thereof an effective amount of a thiol saccharide mucolytic agent, wherein said thiol saccharide mucolytic agent has the formula:

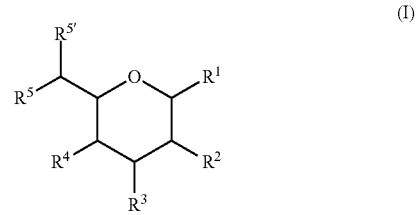

wherein,
$R^1$ is —SH, —$OR^{1A}$, —$NR^{1B}$ or —$R^{1D}$, wherein
$R^{1A}$ is H, substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl;
$R^{1B}$ is —C(O)$R^{1C}$, substituted or unsubstituted $C_1$-$C_{10}$ thiol-alkyl or substituted or unsubstituted 2 to 10 membered thiol-heteroalkyl;
$R^{1C}$ is substituted or unsubstituted $C_1$-$C_{10}$ thiol-alkyl or substituted or unsubstituted 2 to 10 membered thiol-heteroalkyl; and
$R^{1D}$ is substituted or unsubstituted $C_1$-$C_{10}$ thiol-alkyl or substituted or unsubstituted 2 to 10 membered thiol-heteroalkyl;
$R^2$ is —SH, —$OR^{2A}$ or —$NR^{2B}$, wherein
$R^{2A}$ is H, substituted or unsubstituted $C_1$-$C_{10}$ thiol-alkyl or substituted or unsubstituted 2 to 10 membered thiol-heteroalkyl;
$R^{2B}$ is —C(O)$R^{2C}$, substituted or unsubstituted $C_1$-$C_{10}$ thiol-alkyl or substituted or unsubstituted 2 to 10 membered thiol-heteroalkyl; and
$R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl;
$R^3$ is —SH, —$OR^{3A}$ or —$NR^{3B}$, wherein
$R^{3A}$ is H, substituted or unsubstituted $C_1$-$C_{10}$ thiol-alkyl or substituted or unsubstituted 2 to 10 membered thiol-heteroalkyl;
$R^{3B}$ is —C(O)$R^{3C}$, substituted or unsubstituted $C_1$-$C_{10}$ thiol-alkyl or substituted or unsubstituted 2 to 10 membered thiol-heteroalkyl; and
$R^{3C}$ is substituted or unsubstituted $C_1$-$C_{10}$ thiol-alkyl or substituted or unsubstituted 2 to 10 membered thiol-heteroalkyl;
$R^4$ is —SH, —SAc, —$OR^{4A}$ or —$NR^{4B}$, wherein
$R^{4A}$ is H, substituted or unsubstituted $C_1$-$C_{10}$ thiol-alkyl or substituted or unsubstituted 2 to 10 membered thiol-heteroalkyl;
$R^{4B}$ is —C(O)$R^{4C}$, substituted or unsubstituted $C_1$-$C_{10}$ thiol-alkyl or substituted or unsubstituted 2 to 10 membered thiol-heteroalkyl; and
$R^{4C}$ is substituted or unsubstituted $C_1$-$C_{10}$ thiol-alkyl or substituted or unsubstituted 2 to 10 membered thiol-heteroalkyl; and $R^5$ is H, —SH, —SAc, —OR$^{5A}$, —NR$^{5B}$, or —R$^{5D}$, wherein
  $R^{5A}$ is H, substituted or unsubstituted C$_1$-C$_{10}$ thiol-alkyl or substituted or unsubstituted 2 to 10 membered thiol-heteroalkyl;
  $R^{5B}$ is —C(O)R$^{5C}$, substituted or unsubstituted C$_1$-C$_{10}$ thiol-alkyl or substituted or unsubstituted 2 to 10 membered thiol-heteroalkyl;
  $R^{5C}$ is substituted or unsubstituted C$_1$-C$_{10}$ thiol-alkyl or substituted or unsubstituted 2 to 10 membered thiol-heteroalkyl; and
  $R^{5D}$ is substituted or unsubstituted C$_1$-C$_{10}$ thiol-alkyl; and
$R^{5'}$ is H or —OH,
or a pharmaceutically acceptable salt thereof.

2. The method of claim 1, wherein $R^1$ is —OR$^{1A}$ and $R^{1A}$ is substituted or unsubstituted C$_1$-C$_{10}$ alkyl, substituted or unsubstituted C$_1$-C$_{10}$ thiol-alkyl or substituted or unsubstituted 2 to 10 membered thiol-heteroalkyl.

3. The method of claim 1, wherein
  $R^1$, $R^3$, $R^4$ and $R^5$ are —OH;
  $R^{5'}$ is H;
  $R^{2A}$ is an unsubstituted C$_1$-C$_{10}$ thiol-alkyl or unsubstituted 2 to 10 membered thiol-heteroalkyl;
  $R^{2B}$ is —C(O)R$^{2C}$, unsubstituted C$_1$-C$_{10}$ thiol-alkyl or unsubstituted thiol-heteroalkyl; and
  $R^{2C}$ is substituted or unsubstituted C$_1$-C$_{10}$ thiol-alkyl or substituted or unsubstituted 2 to 10 membered thiol-heteroalkyl.

4. The method of claim 1, wherein $R^2$, $R^3$, $R^4$ are —OH.

5. The method of claim 1, wherein
  $R^3$, $R^4$ and $R^5$ are —OH; and
  R5' is H.

6. The method of claim 1, wherein $R^4$ is —SH.

7. The method of claim 1, wherein
  $R^5$ is —SH; and
  $R^{5'}$ is H.

8. The method of claim 1, wherein
  $R^1$ is —OR$^{1A}$;
  $R^2$, $R^3$, and $R^4$ are —OH;
  $R^5$ is H or —OR$^{5A}$; and
  $R^{5'}$ is H.

9. The method of claim 1, wherein
  $R^1$ is —OR$^{1A}$;
  $R^2$, $R^3$, and $R^4$ are —OH;
  $R^{5'}$ is H; and
  $R^5$ is —SH.

10. The method of claim 1, wherein
  $R^1$ is —OR$^{1A}$;
  $R^2$, $R^3$, and $R^4$ are —OH;
  $R^5$ is —SAc; and
  $R^{5'}$ is H.

11. The method of claim 1, wherein
  $R^1$ is —OR$^{1A}$ or —R$^{1D}$;
  $R^2$ is —OH or —NR$^{2B}$;
  $R^{2B}$ is —C(O)R$^{2C}$;
  $R^{2C}$ is substituted or unsubstituted C$_1$-C$_{10}$ alkyl;
  $R^3$ and $R^4$ are —OH; and
  $R^5$ is —OR$^{5A}$ or —R$^{5D}$.

12. A pulmonary pharmaceutical composition comprising a pulmonary pharmaceutical carrier and a thiol saccharide mucolytic agent, wherein said thiol saccharide mucolytic agent has the formula:

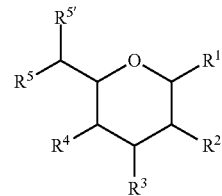

(I)

wherein,
$R^1$ is —SH, —OR$^{1A}$, —NR$^{1B}$ or —R$^{1D}$, wherein
  $R^{1A}$ is H, substituted or unsubstituted C$_1$-C$_{10}$ alkyl, substituted or unsubstituted C$_1$-C$_{10}$ thiol-alkyl or substituted or unsubstituted 2 to 10 membered thiol-heteroalkyl;
  $R^{1B}$ is —C(O)R$^{1C}$, substituted or unsubstituted C$_1$-C$_{10}$ thiol-alkyl or substituted or unsubstituted 2 to 10 membered thiol-heteroalkyl;
  $R^{1C}$ is substituted or unsubstituted C$_1$-C$_{10}$ thiol-alkyl or substituted or unsubstituted 2 to 10 membered thiol-heteroalkyl; and
  $R^{1D}$ is substituted or unsubstituted C$_1$-C$_{10}$ thiol-alkyl or substituted or unsubstituted 2 to 10 membered thiol-heteroalkyl;
$R^2$ is —SH, —OR$^{2A}$ or —NR$^{2B}$, wherein
  $R^{2A}$ is H, substituted or unsubstituted C$_1$-C$_{10}$ thiol-alkyl or substituted or unsubstituted 2 to 10 membered thiol-heteroalkyl;
  $R^{2B}$ is —C(O)R$^{2C}$, substituted or unsubstituted C$_1$-C$_{10}$ thiol-alkyl or substituted or unsubstituted 2 to 10 membered thiol-heteroalkyl; and
  $R^{2C}$ is substituted or unsubstituted C$_1$-C$_{10}$ alkyl, substituted or unsubstituted C$_1$-C$_{10}$ thiol-alkyl or substituted or unsubstituted 2 to 10 membered thiol-heteroalkyl;
$R^3$ is —SH, —OR$^{3A}$ or —NR$^{3B}$, wherein
  $R^{3A}$ is H, substituted or unsubstituted C$_1$-C$_{10}$ thiol-alkyl or substituted or unsubstituted 2 to 10 membered thiol-heteroalkyl;
  $R^{3B}$ is —C(O)R$^{3C}$, substituted or unsubstituted C$_1$-C$_{10}$ thiol-alkyl or substituted or unsubstituted 2 to 10 membered thiol-heteroalkyl; and
  $R^{3C}$ is substituted or unsubstituted C$_1$-C$_{10}$ thiol-alkyl or substituted or unsubstituted 2 to 10 membered thiol-heteroalkyl;
$R^4$ is —SH, —SAc, —OR$^{4A}$ or —NR$^{4B}$, wherein
  $R^{4A}$ is H, substituted or unsubstituted C$_1$-C$_{10}$ thiol-alkyl or substituted or unsubstituted 2 to 10 membered thiol-heteroalkyl;
  $R^{4B}$ is —C(O)R$^{4C}$, substituted or unsubstituted C$_1$-C$_{10}$ thiol-alkyl or substituted or unsubstituted 2 to 10 membered thiol-heteroalkyl; and
  $R^{4C}$ is substituted or unsubstituted C$_1$-C$_{10}$ thiol-alkyl or substituted or unsubstituted 2 to 10 membered thiol-heteroalkyl; and
$R^5$ is H, —SH, —SAc, —OR$^{5A}$, —NR$^{5B}$, or —R$^{5D}$, wherein
  $R^{5A}$ is H, substituted or unsubstituted C$_1$-C$_{10}$ thiol-alkyl or substituted or unsubstituted 2 to 10 membered thiol-heteroalkyl;
  $R^{5B}$ is —C(O)R$^{5C}$, substituted or unsubstituted C$_1$-C$_{10}$ thiol-alkyl or substituted or unsubstituted 2 to 10 membered thiol-heteroalkyl;

$R^{5C}$ is substituted or unsubstituted $C_1$-$C_{10}$ thiol-alkyl or substituted or unsubstituted 2 to 10 membered thiol-heteroalkyl; and $R^{5D}$ is substituted or unsubstituted $C_1$-$C_{10}$ thiol-alkyl; and $R^{5'}$ is H or —OH, or a pharmaceutically acceptable salt thereof.

13. A compound with the structure of Formula (I):

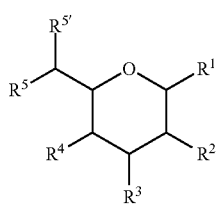

(I)

wherein, $R^1$, $R^3$, $R^4$ and $R^5$ are —OH;

$R^{5'}$ is H; and $R^2$ is —SH, —OR$^{2A}$ or —NR$^{2B}$, wherein $R^{2A}$ is an unsubstituted $C_1$-$C_{10}$ thiol-alkyl or unsubstituted 2 to 10 membered thiol-heteroalkyl;

$R^{2B}$ is —C(O)R$^{2C}$, unsubstituted $C_1$-$C_{10}$ thiol-alkyl or unsubstituted thiol-heteroalkyl; and $R^{2C}$ is substituted or unsubstituted $C_1$-$C_{10}$ thiol-alkyl or substituted or unsubstituted 2 to 10 membered thiol-heteroalkyl, or a pharmaceutically acceptable salt thereof.

14. A compound with the structure of Formula (I):

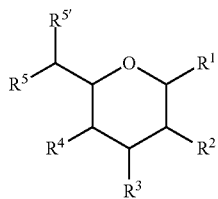

(I)

wherein, $R^1$ is —SH, —OR$^{1A}$, —NR$^{1B}$ or —R$^{1D}$, wherein $R^{1A}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl;

$R^{1B}$ is —C(O)R$^{1C}$, substituted or unsubstituted $C_1$-$C_{10}$ thiol-alkyl or substituted or unsubstituted 2 to 10 membered thiol-heteroalkyl;

$R^{1C}$ is substituted or unsubstituted $C_1$-$C_{10}$ thiol-alkyl or substituted or unsubstituted 2 to 10 membered thiol-heteroalkyl; and $R^{1D}$ is substituted or unsubstituted $C_1$-$C_{10}$ thiol-alkyl or substituted or unsubstituted 2 to 10 membered thiol-heteroalkyl;

$R^2$ is —SH, —OR$^{2A}$ or —NR$^{2B}$, wherein $R^{2A}$ is H, substituted or unsubstituted $C_1$-$C_{10}$ thiol-alkyl or substituted or unsubstituted 2 to 10 membered thiol-heteroalkyl;

$R^{2B}$ is —C(O)R$^{2C}$, substituted or unsubstituted $C_1$-$C_{10}$ thiol-alkyl or substituted or unsubstituted 2 to 10 membered thiol-heteroalkyl; and $R^{2C}$ is substituted or unsubstituted $C_1$-$C_{10}$ alkyl, substituted or unsubstituted $C_1$-$C_{10}$ thiol-alkyl or substituted or unsubstituted 2 to 10 membered thiol-heteroalkyl;

$R^3$ is —SH, —OR$^{3A}$ or —NR$^{3B}$, wherein $R^{3A}$ is H, substituted or unsubstituted $C_1$-$C_{10}$ thiol-alkyl or substituted or unsubstituted 2 to 10 membered thiol-heteroalkyl;

$R^{3B}$ is —C(O)R$^{3C}$, substituted or unsubstituted $C_1$-$C_{10}$ thiol-alkyl or substituted or unsubstituted 2 to 10 membered thiol-heteroalkyl; and $R^{3C}$ is substituted or unsubstituted $C_1$-$C_{10}$ thiol-alkyl or substituted or unsubstituted 2 to 10 membered thiol-heteroalkyl;

$R^4$ is —SH;

$R^5$ is H, —SH, —SAc, —OR$^{5A}$, —NR$^{5B}$, or —R$^{5D}$, wherein $R^{5A}$ is H, substituted or unsubstituted $C_1$-$C_{10}$ thiol-alkyl or substituted or unsubstituted 2 to 10 membered thiol-heteroalkyl;

$R^{5B}$ is —C(O)R$^{5C}$, substituted or unsubstituted $C_1$-$C_{10}$ thiol-alkyl or substituted or unsubstituted 2 to 10 membered thiol-heteroalkyl;

$R^{5C}$ is substituted or unsubstituted $C_1$-$C_{10}$ thiol-alkyl or substituted or unsubstituted 2 to 10 membered thiol-heteroalkyl; and $R^{5D}$ is substituted or unsubstituted $C_1$-$C_{10}$ thiol-alkyl; and $R^{5'}$ is H or —OH, provided, however, that said structure is not

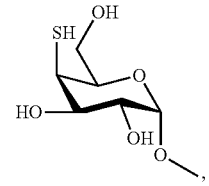

, or a pharmaceutically acceptable salt thereof.

15. The composition of claim 12, wherein $R^1$, $R^3$, $R^4$ and $R^5$ are —OH;

$R^{5'}$ is H;

$R^{2A}$ is an unsubstituted $C_1$-$C_{10}$ thiol-alkyl or unsubstituted 2 to 10 membered thiol-heteroalkyl;

$R^{2B}$ is —C(O)R$^{2C}$, unsubstituted $C_1$-$C_{10}$ thiol-alkyl or unsubstituted thiol-heteroalkyl; and $R^{2C}$ is substituted or unsubstituted $C_1$-$C_{10}$ thiol-alkyl or substituted or unsubstituted 2 to 10 membered thiol-heteroalkyl.

16. The composition of claim 12, wherein $R^2$, $R^3$, $R^4$ are —OH.

17. The composition of claim 12, wherein $R^3$, $R^4$ and $R^5$ are —OH; and

R5' is H.

18. The composition of claim 12, wherein $R^4$ is —SH.

19. The composition of claim 12, wherein $R^5$ is —SH; and $R^{5'}$ is H.

20. The composition of claim 12, wherein $R^1$ is —OR$^{1A}$;

$R^2$, $R^3$, and $R^4$ are —OH;

$R^5$ is H or —OR$^{5A}$; and $R^{5'}$ is H.

21. The composition of claim 12, wherein $R^1$ is —$OR^{1A}$;

$R^2$, $R^3$, and $R^4$ are —OH;

$R^{5'}$ is H; and $R^5$ is —SH.

22. The composition of claim 12, wherein $R^1$ is —$OR^{1A}$;

$R^2$, $R^3$, and $R^4$ are —OH;

$R^5$ is —SAc; and $R^{5'}$ is H.

23. The composition of claim 12, wherein $R^1$ is —$OR^{1A}$ or —$R^{1D}$;

$R^2$ is —OH or —$NR^{2B}$;

$R^{2B}$ is —$C(O)R^{2C}$;

$R^{2C}$ is substituted or unsubstituted $C_1$-$C_{10}$ alkyl;

$R^3$ and $R^4$ are —OH; and $R^5$ is —$OR^{5A}$ or —$R^{5D}$.

24. The composition of claim 12, wherein the thiol saccharide mucolytic agent has the structure:

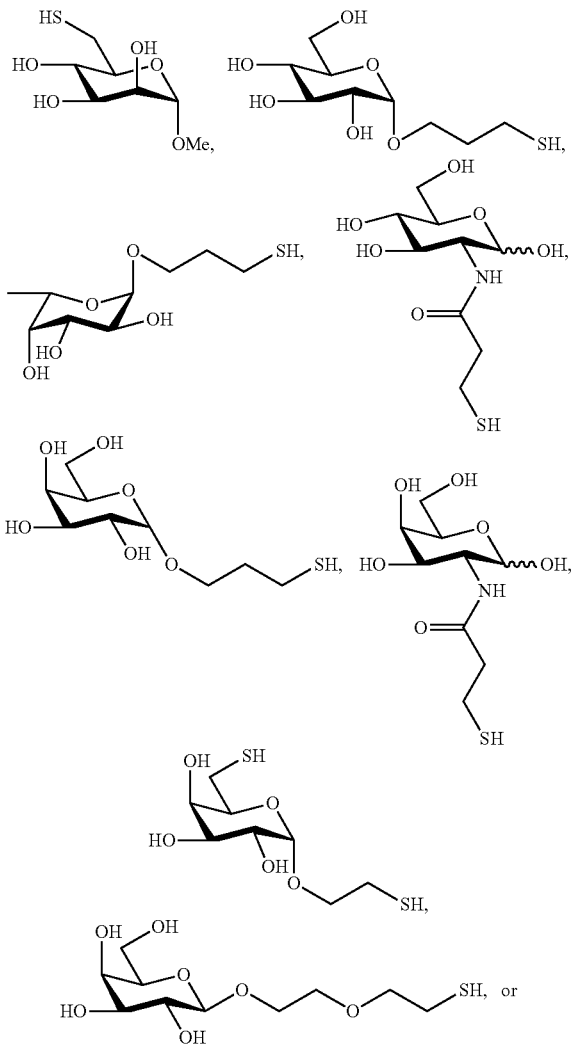

25. The composition of claim 12, wherein the thiol saccharide mucolytic agent has the structure:

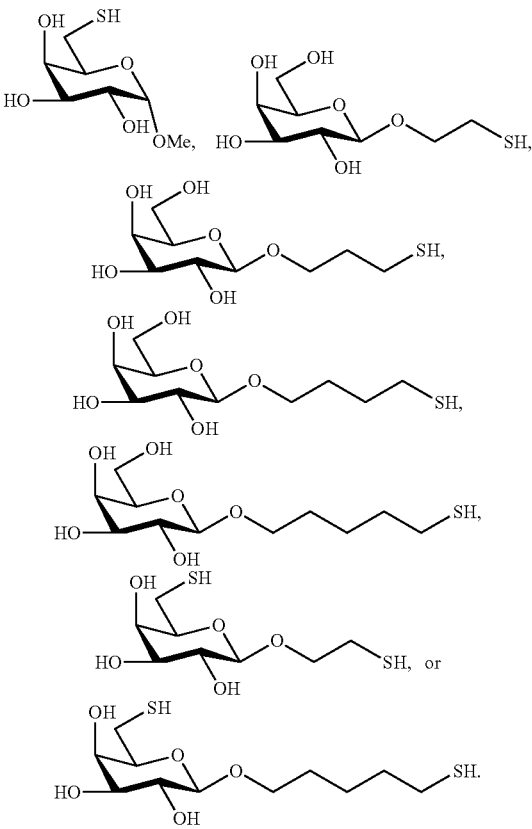

26. The method of claim 1, wherein the thiol saccharide mucolytic agent has the structure:

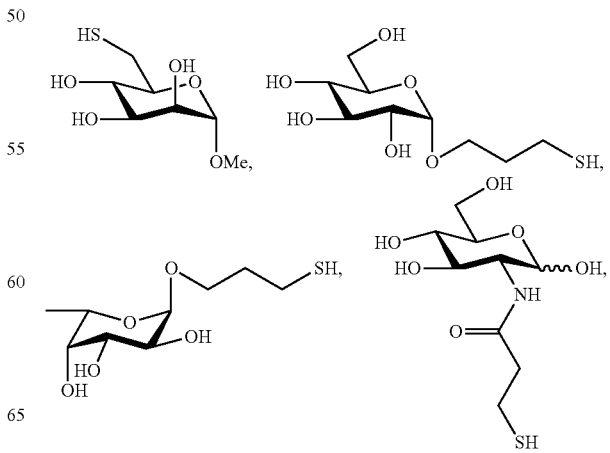

-continued
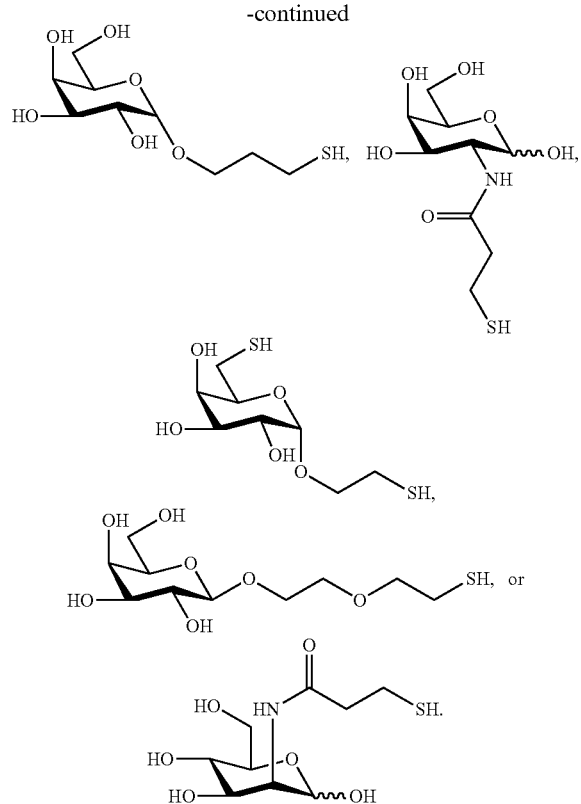
27. The method of claim 1, wherein the thiol saccharide mucolytic agent has the structure:
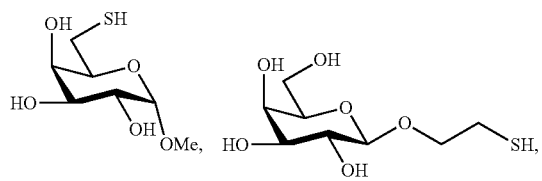
-continued
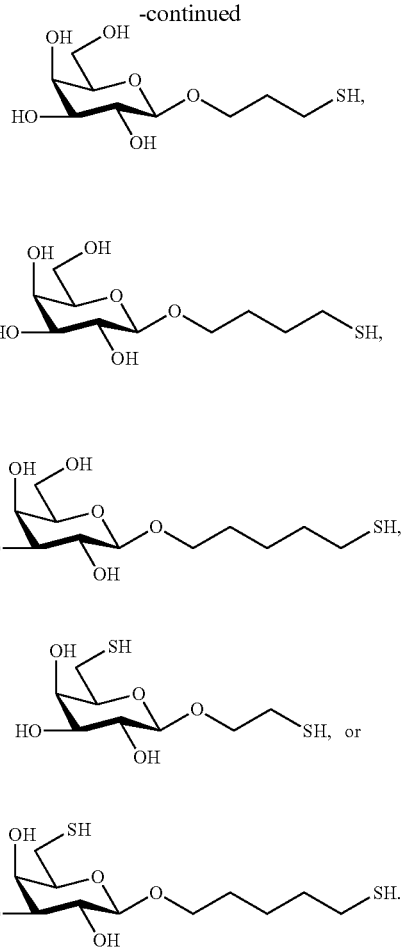
28. The method of claim 1, wherein $R^1$ is —SH.
29. The method of claim 1, wherein $R^5$ is —SH.
30. The composition of claim 12, wherein $R^1$ is —SH.
31. The composition of claim 12, wherein $R^5$ is —SH.
* * * * *